(12) United States Patent
An et al.

(10) Patent No.: US 10,767,231 B2
(45) Date of Patent: Sep. 8, 2020

(54) METHOD FOR DETECTING LUNG CANCER USING LUNG CANCER-SPECIFIC METHYLATION MARKER GENE

(71) Applicant: GENOMICTREE, INC., Daejeon (KR)

(72) Inventors: Sung Whan An, Daejeon (KR); Young Ho Moon, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 0 days.

(21) Appl. No.: 15/814,354

(22) Filed: Nov. 15, 2017

(65) Prior Publication Data

US 2018/0066324 A1   Mar. 8, 2018

Related U.S. Application Data

(63) Continuation-in-part of application No. 12/922,184, filed as application No. PCT/KR2009/000777 on Feb. 18, 2009, now Pat. No. 9,850,540.

(30) Foreign Application Priority Data

Mar. 14, 2008   (KR) .................. 10-2008-0023685

(51) Int. Cl.
  *C12Q 1/6886* (2018.01)
  *C12Q 1/6811* (2018.01)
  *C12P 19/34* (2006.01)

(52) U.S. Cl.
  CPC .......... *C12Q 1/6886* (2013.01); *C12Q 1/6811* (2013.01); *C12Q 2600/112* (2013.01); *C12Q 2600/154* (2013.01); *C12Q 2600/156* (2013.01)

(58) Field of Classification Search
  None
  See application file for complete search history.

(56) References Cited

U.S. PATENT DOCUMENTS

| | | | |
|---|---|---|---|
| 5,541,308 A | 7/1996 | Hogan et al. | |
| 7,871,774 B2 | 1/2011 | Yoon et al. | |
| 2007/0264659 A1 | 11/2007 | An et al. | |
| 2009/0264306 A1 | 10/2009 | Caldwell et al. | |
| 2009/0305256 A1 | 12/2009 | Pfeifer et al. | |
| 2011/0027796 A1 | 2/2011 | An et al. | |

FOREIGN PATENT DOCUMENTS

| | | |
|---|---|---|
| CN | 1820785 A | 8/2006 |
| KR | 10-2006-0027893 A | 3/2006 |

OTHER PUBLICATIONS

Li (MethPrimer, 2002, vol. 18, p. 1427-1431).*
Ahlquist, D., et al., "Colorectal Cancer Screening by Detection of Altered Human DNA in Stool: Feasibility of a Multitarget Assay Panel", "Gastroenterology", Nov. 2000, pp. 1219-1227, vol. 119, No. 5.
An, S., et al., "Abstract #3357: Identification of hypermethylation of PCDHGA12 gene by genome-wide analysis as a novel diagnostic marker of lung cancer", "Proceedings of the American Association for Cancer Research Annual Meeting", Apr. 18-22, 2009.
Brock, M. V., et al., "DNA Methylation Markers and Early Recurrence in Stage I Lung Cancer", "The New England Journal of Medicine", Mar. 13, 2008, pp. 1118-1128, vol. 358.
Buck, G. A., et al, "Design Strategies and Performance of Custom DNA Sequencing Primers", "BioTechniques", Sep. 1999, pp. 528-536, vol. 27, No. 3.
Office Action for Chinese Patent Application No. 2009-80108952.2, dated May 16, 2014.
Cottrell, S. E., "Molecular diagnostic applications of DNA methylation technology", "Clinical Biochemistry", 2004, pp. 595-604, vol. 37.
Supplemental European Search Report in European Patent Application No. EP 09 72 0916, report completed May 24, 2011.
Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.
Feinberg, A. P., et al., "The history of cancer epigenetics", "Nature Reviews", Feb. 2004, pp. 143-153, vol. 4.
Goo, Y., et al., "Stromal mesenchyme cell genes of the human prostate and bladder", "BMC Urology", Dec. 2005, pp. 1-11, vol. 5.
Homo sapiens chromosome 5 genomic contig, GRCh37.p@ reference primary assembly, NCBI Reference Sequence: NT_029289.11.
Jones, P. et al., "The Fundamental Role of Epigenetic Events in Cancer", "Nature Reviews Genetics", Jun. 2002, pp. 415-428, vol. 3.
Kopreski, M., et al., "Detection of Tumor Messenger RNA in the Serum of Patients with Malignant Melanoma", "Clinical Cancer Research", Aug. 1999, pp. 1961-1965, vol. 5.
Lu, Y., et al., "A Gene Expression Signature Predicts Survival of Patients with Stage I Non-Small Cell Lung Cancer", "PLoS Medicine", Dec. 2006, pp. 2229-2242, vol. 3, No. 12.
Miyashiro, I., et al, "Molecular Strategy for Detecting Metastatic Cancers with Use of Multiple Tumor-specific Mage-A Genes", "Clinical Chemistry", Mar. 2001, pp. 505-512, vol. 47, No. 3.
Moon, Y.H., et al., "Methylated DNA Isolation Assay-Medicated Dna Methylation Detection and Whole-Genome Methylation Profiling", "American Biotechnology Laboratory", Oct. 2009, pp. 23-25, vol. 27, No. 10.
Palmisano, W., et al., "Predicting Lung Cancer by Detecting Aberrant Promoter Methylation in Sputum", "Cancer Research", Nov. 1, 2000, pp. 5954-5958, vol. 60.

(Continued)

*Primary Examiner* — Sarae L Bausch
(74) *Attorney, Agent, or Firm* — Hultquist, PLLC; Steven J. Hultquist

(57) ABSTRACT

The present invention relates to a method for detecting lung cancer using a lung cancer-specific biomarker, and more particularly to a biomarker for lung cancer diagnosis, which can detect methylation of PCDHGA12 gene whose 5'UTR or exon 1 region is specifically methylated in lung cancer cells, and to a method of detecting lung cancer and the stage of its progression using the biomarker. The diagnostic kit according to the present invention makes it possible to diagnose lung cancer at an early stage in an accurate and rapid manner compared to conventional methods and can be used for prognosis and monitoring of lung cancer and the stage of its progression.

5 Claims, 5 Drawing Sheets
(2 of 5 Drawing Sheet(s) Filed in Color)

Specification includes a Sequence Listing.

(56) References Cited

OTHER PUBLICATIONS

Sakaguchi, M., et al., "Frequent suppression of protocadherin gene expression in small cell lunch carcinoma cell lines", "Proceedings of the American Association for Cancer Research Annual Meeting", Mar. 1999, p. 133 vol. 40; Note: Reference Not Attached As This Reference Cannot Be Located; See the Supplemental European Search Report for a Brief Description of the Relevance of This Reference.
Sanchez-Cespedes, M., et al., "Gene Promoter Hypermethylation in Tumors and Serum of Head and Neck Cancer Patients", "Cancer Research", Feb. 15, 2000, pp. 892-895, vol. 60.
Schena, Mark, et al., "Quantitative monitoring of gene expression patterns with a complementary DNA microarray", "Science", Oct. 20, 1995, pp. 467-470, vol. 270.
Smiraglia, D. J., et al., "Excessive CpG island hypermethylation in cancer cell lines versus primary human malignancies", "Human Molecular Genetics", 2001, pp. 1413-1419, vol. 10, No. 13.
Sueoka, E., et al., "Heterogeneous Nuclear Ribonucleoprotein B1 as a New Marker of Early Detection for Human Lung Cancers", "Cancer Research", Apr. 1, 1999, pp. 1404-1407, vol. 59.
Taylor, K. H., et al., "Large-Scale CpG Methylation Analysis Identifies Novel Candidate Genes and Reveals Methylation Hotspots in Acute Lymphoblastic Leukemia", "Cancer Research", Mar. 15, 2007, pp. 2617-2625, vol. 67, No. 6.
Verma, M., et al, "Genetic and epigenetic biomarkers in cancer diagnosis and identifying high risk populations", "Critical Reviews in Oncology/Hematology", 2006, pp. 9-18, vol. 60.
Note: For the non-patent literature citations that no month of publication is indicated, the year of publication is more than 1 year prior to the effective filing date of the present application.

\* cited by examiner

○: nonmethylated
●: methylated

☐ Normal tissues from non-patients  ▨ Tumor-adjacent normal issues  ■ Tumor tissues

*PCDHGA12*R3

M: 1kb ladder
1: NHBE
2: A549
3: NHBE Input
4: A549 Iinput

M: 1kb ladder
1: normal-1
2: normal-2
3: normal-3
4: lung cancer-1
5: lung cancer-2
6: lung cancer-3
P: positive control
DW: bank

METHOD FOR DETECTING LUNG CANCER USING LUNG CANCER-SPECIFIC METHYLATION MARKER GENE

CROSS-REFERENCE TO RELATED APPLICATIONS

This is a continuation-in-part application under 35 U.S.C. § 120 of U.S. patent application Ser. No. 12/922,184 filed Sep. 13, 2010, which in turn is a U.S. national phase under the provisions of 35 U.S.C. § 371 of International Patent Application No. PCT/KR2009/000777 filed Feb. 18, 2009, which in turn claims priority of Korean Patent Application No. 10-2008-0023685 filed Mar. 14, 2008. The disclosures of U.S. patent application Ser. No. 12/922,184, International Patent Application No. PCT/KR2009/000777, and Korean Patent Application No. 10-2008-0023685 are hereby incorporated herein by reference in their respective entireties, for all purposes.

TECHNICAL FIELD

The present invention relates to a method for detecting lung cancer using a lung cancer-specific biomarker, and more particularly to a biomarker for lung cancer diagnosis, which can detect methylation of PCDHGA12 gene whose 5' UTR or exon 1 region is specifically methylated in transformed lung cancer cells, and to a method of detecting lung cancer and the stage of its progression using the biomarker.

BACKGROUND ART

Lung cancer was a very rare disease before cigarette smoking became common in the 20$^{th}$ century. The incidence of lung cancer has increased rapidly, and in Western countries, lung cancer is the most frequent cancer in both men and women. In Korea, lung cancer frequently occurs in men, and its incidence in women is also dramatically increasing. This increase in the incidence of lung cancer is attributable to increases in cigarette smoking, air pollution and industrial pollution and so on.

Even at the present time when medical science has advanced, the 5-year survival rate of cancer patients, particularly solid tumor patients (other than blood cancer patients) is less than 50%, and about ⅔ of all cancer patients are diagnosed at an advanced stage and almost all die within 2 years after cancer diagnosis. Such poor results in cancer therapy are not only the problem of therapeutic methods, but also due to the fact that it is not easy to diagnose cancer at an early stage and to accurately diagnose advanced cancer and to carry out the follow-up of cancer patients after cancer therapy.

Recently, genetic testing methods have actively been attempted to diagnose cancer. Among them, a typical method is to use PCR to determine whether or not the ABL:BCR (Abelson Murine Leukemia Viral Oncogene Homolog: Breakpoint cluster region) fusion gene that is a genetic indicator of leukemia is present in blood. Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. Also, it is difficult to standardize detection and reading in this method, and its utility is also (Kopreski, M. S. et al., *Clin. Cancer Res.,* 5:1961, 1999; Miyashiro, I. et al., *Clin. Chem.,* 47:505, 2001). In addition, genetic testing using a DNA in serum or plasma has recently been actively attempted. The use of DNA isolated from cancer to analyze cancer-specific gene abnormalities, such as the mutation, deletion and functional loss of oncogenes and tumor-suppressor genes, allows the diagnosis of cancer.

Meanwhile, a method is being attempted in which the presence of cancer cells or oncogenes in the sputum or bronchoalveolar lavage fluid of lung cancer patients is detected by a gene or antibody test (Palmisano, W. A. et al., *Cancer Res.,* 60:5954, 2000; Sueoka, E. et al., *Cancer Res.,* 59:1404, 1999). However, in order to accurately diagnose cancers that involve a large number of gene abnormalities and show various mutations, a method capable of simultaneously analyzing a large number of genes in an accurate and automatic manner is required, but such a method has not yet been established.

Accordingly, methods of diagnosing cancer by measuring DNA methylation have recently been proposed. DNA methylation occurs mainly at cytosines of CpG islands in the promoter region of a specific gene, and thus the binding of a transcription factor is hindered so that the expression of a specific gene is silenced. Thus, analysis of the methylation of the promoter CpG island of tumor-suppressor genes is very helpful in cancer research. An active attempt has been made to analyze the methylation of the promoter CpG island by methods such as methylation-specific PCR (hereinafter, referred to as "MSP") or automatic base sequencing and to use the analysis results for the diagnosis and screening of cancer.

Although there are disputes about whether the methylation of promoter CpG islands directly induces oncogenesis or causes secondary changes in oncogenesis, it has been confirmed that tumor suppressor genes, DNA repair genes, cell cycle regulator genes and the like in various cancers are hyper-methylationed so that the expression of these genes is silenced. Particularly, it is known that the hypermethylation of the promoter region of a specific gene occurs in the early stage of oncogenesis.

Accordingly, the promoter methylation of tumor-related genes is an important indicator of cancer and can be used in many applications, including the diagnosis and early detection of cancer, the prediction of the risk of oncogenesis, the prediction of the prognosis of cancer, follow-up examination after treatment, and the prediction of a response to anticancer therapy. Indeed, an attempt has recently been actively made to examine the promoter methylation of tumor-related genes in blood, sputum, saliva, feces or urine and to use the examination results for the diagnosis and treatment of various cancers (Esteller, M. et al., *Cancer Res.,* 59:67, 1999; Sanchez-Cespedez, M. et al., *Cancer Res.,* 60:892, 2000; Ahlquist, D. A. et al., *Gastroenterol.,* 119:1219, 2000).

Currently, the diagnosis of lung cancer is possible by various examinations, and if a symptom suspected of lung cancer exists, chest X-ray examination, microscopic examination, video examination, biopsy, examination of metastasis or the like is performed to determine whether the symptom is lung cancer and to determine the degree of progression of lung cancer. However, this detection method requires an expensive system, is costly, has difficulty and is not suitable for the early diagnosis of lung cancer, and in addition, there is difficulty in sampling. Thus, in view of the fact that the 5-year survival rate of stage I lung cancer patients having a tumor size of less than 3 cm reaches about 70%, diagnosing lung cancer at an early stage when the size of the lesion is small is the best method. Accordingly, it is urgently required to develop a detection method which is more efficient than various existing lung cancer detection methods. Namely, it is required to develop a novel lung cancer-specific biomarker which can diagnose lung cancer at an early stage, treat large volumes of samples and has high sensitivity and specificity.

Accordingly, the present inventors filed and received a patent for a microarray and kit for cancer diagnosis including the colon cancer-specific expression-decreased genes LAMA2 (laminin merosin alpha 2), FABP4 (fatty acid binding protein 4), GSTA2 (glutathione S-transferase A2), STMN2 (stathmin-like 2), NR4A2 (nuclear receptor subfamily 4, group A, member 2), DSCR1L1 (down syndrome critical region gene 1-like 1), A2M (alpha-2-macroglobulin) and SEPP1 (selenoprotein P, plasma, 1) (Korean Patent Registration No. 10-0617649).

The present inventors have made many efforts to develop a diagnostic kit capable of effectively diagnosing lung cancer and, as a result, have found that lung cancer and the stage of its progression can be diagnosed by measuring the degree of methylation using the methylated 5'UTR or methylated exon 1 region of PCDHGA12 (GenBank NM_032094) gene, which is specifically methylated in lung cancer cells, as a lung cancer-specific biomarker, thereby completing the present invention.

SUMMARY OF INVENTION

It is an object of the present invention to provide a biomarker for lung cancer diagnosis containing a methylated region of a gene which is specifically methylated in lung cancer.

Another object of the present invention is to provide a method of detecting lung cancer and the stage of its progression using a biomarker for lung cancer diagnosis.

To achieve the above objects, the present invention provides a biomarker for lung cancer diagnosis comprising the methylated 5'UTR or exon 1 region of the lung cancer-specific expression-decreased gene PCDHGA12 (GenBank NM_032094, protocadherin gamma subfamily A, 12).

The present invention also provides a biomarker for lung cancer diagnosis, which contains one or more methylated CpG islands and is represented by any one base sequence of SEQ ID NOs: 437 to 439.

The present invention also provides a method for detecting lung cancer or the stage of its progression, the method comprising the steps of: (a) isolating DNA from a clinical sample; and (b) detecting methylation of the 5'UTR or exon 1 region of the lung cancer-specific gene PCDHGA12 (GenBank NM_032094, protocadherin gamma subfamily A, 12) in the isolated DNA.

Other features and embodiments of the present invention will be more apparent from the following description and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION, AND PREFERRED EMBODIMENTS

Figure 1:
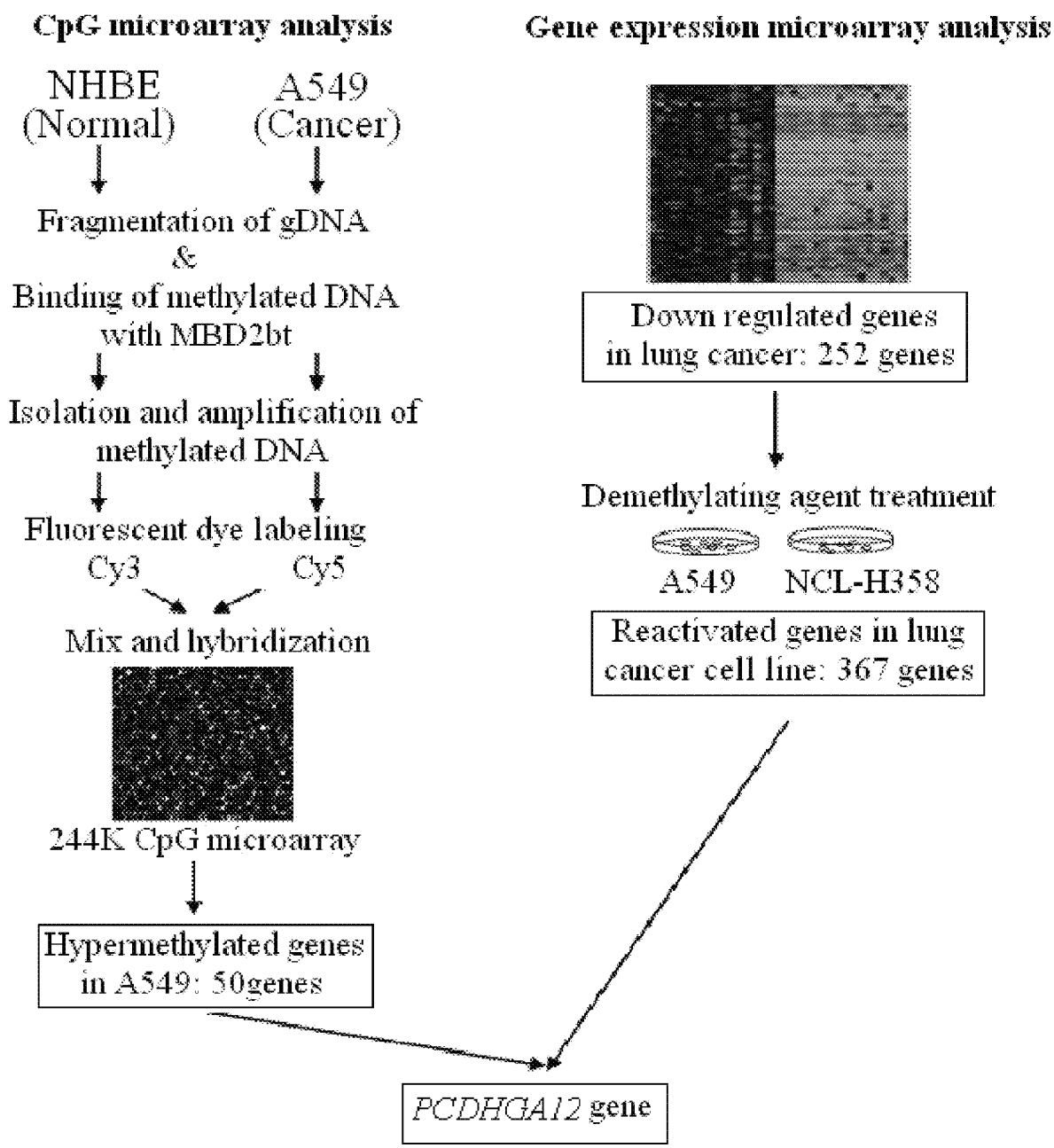
FIG. 1 is a schematic diagram showing a process of discovering the methylation biomarker PCDHGA12 for lung cancer diagnosis.
Figure 2A:
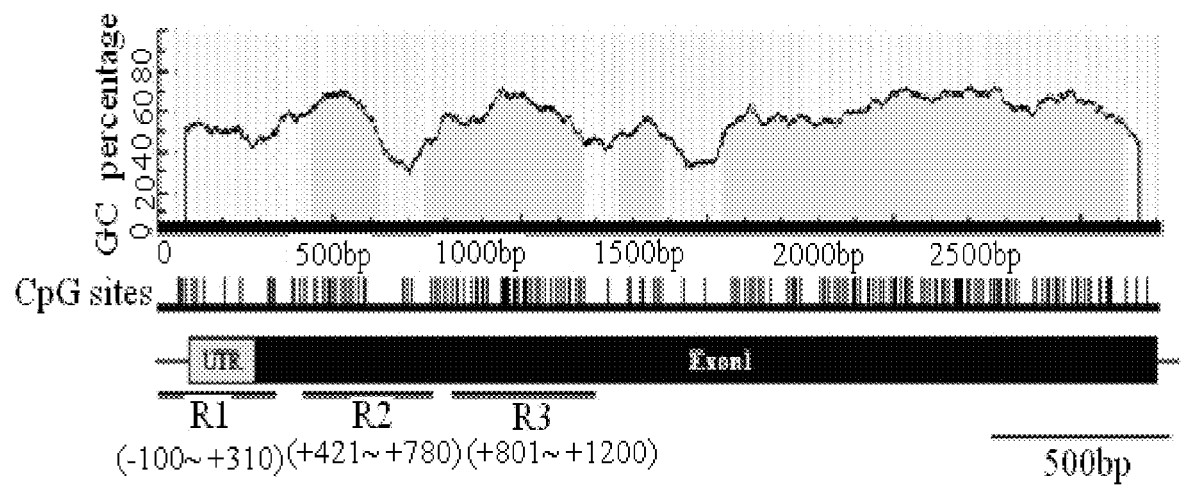
FIGS. 2A-2B show the results of measuring the methylation degree of a gene region (FIG. 2A) and the methylation degree of UTR and exon regions (FIG. 2B) by bisulfite sequencing in order to determine the degree of methylation of PCDHGA12 in normal cell and lung cell lines.
Figure 2B:
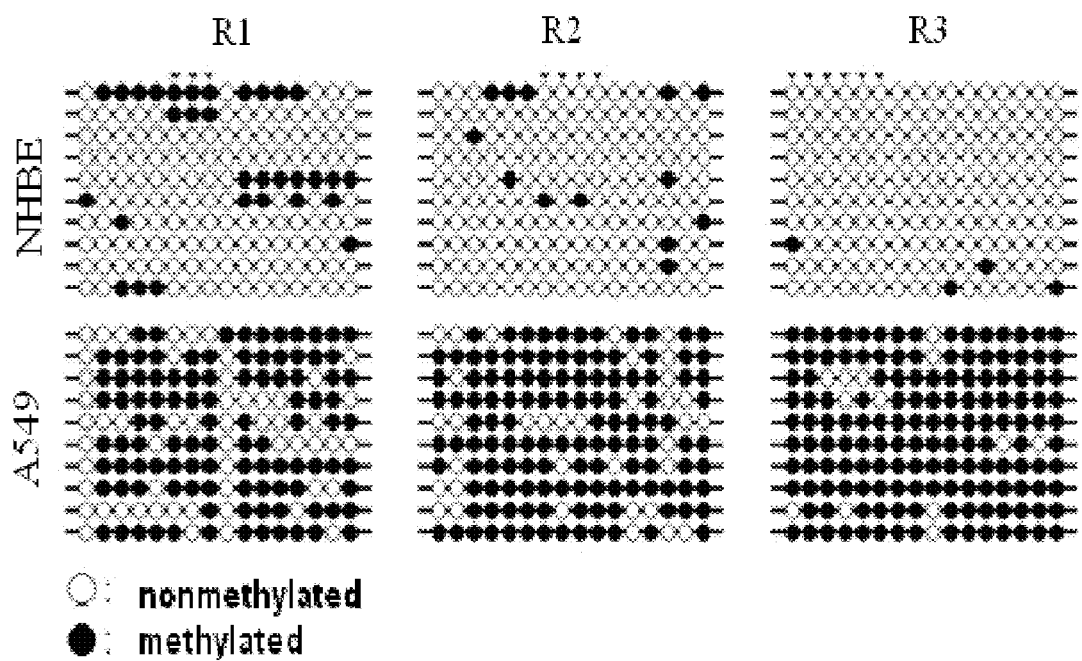
Figure 3:
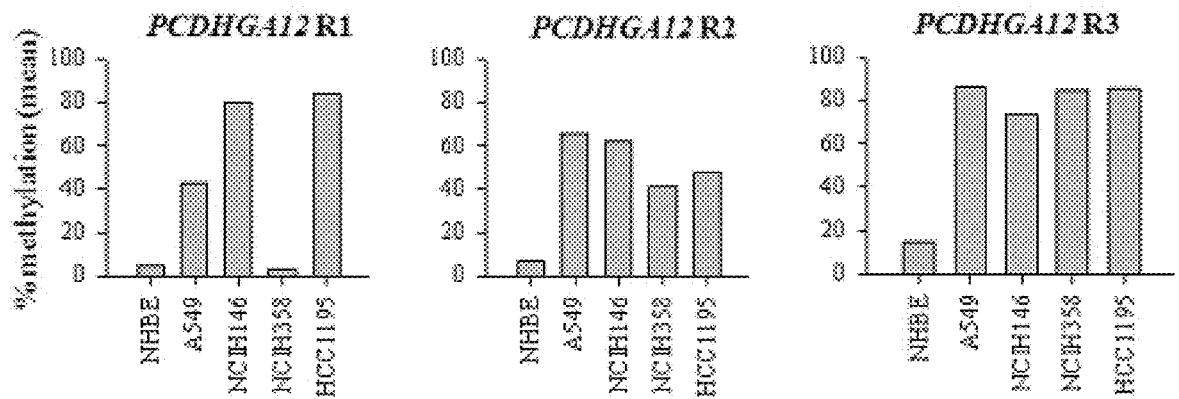
FIG. 3 shows the results of measuring the methylation degree of PCDHGA12 gene in normal cells and four kinds of lung cells by pyrosequencing.
Figure 4:
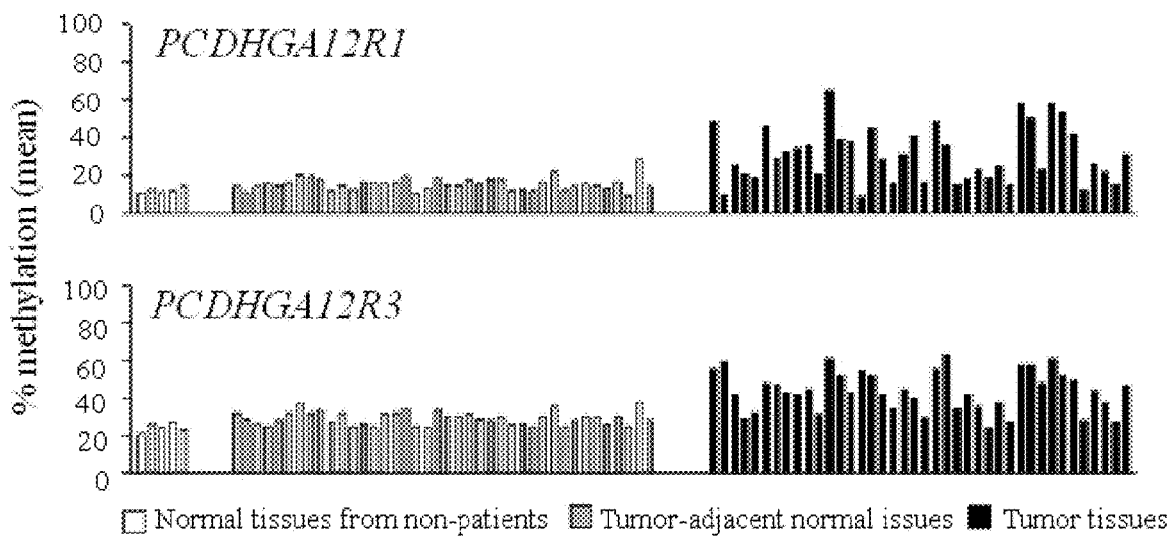
FIG. 4 shows the results of measuring the methylation degree of PCDHGA12 in five normal tissues and forty paired lung cancer tissues by pyrosequencing.
Figure 5:
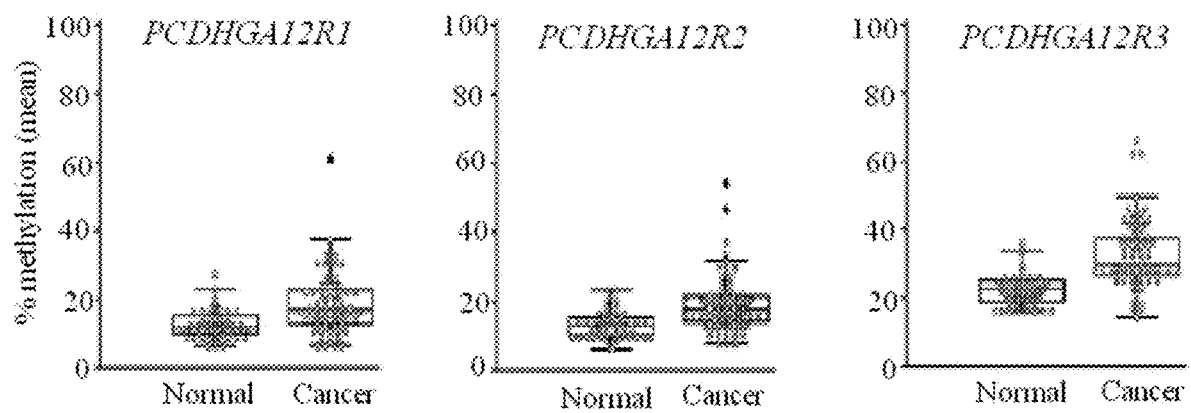
FIG. 5 shows the results of measuring the methylation of the genomic DNA of sputum cells of normal persons (n=51) and lung cancer patients (n=81).
Figure 6A:
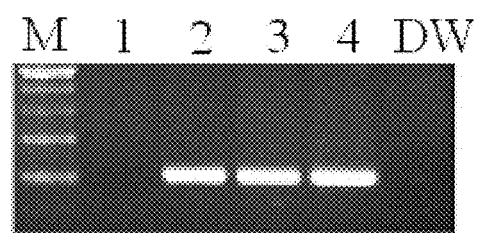
FIGS. 6A-6B show the results of measuring the promoter methylation of PCDHGA12 gene using the sputum DNA of each of normal and lung cancer cell lines and normal and lung cancer patients.
Figure 6B:
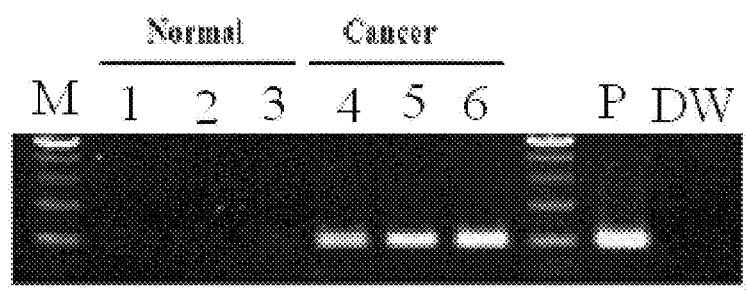

In one aspect, the present invention relates to a biomarker for lung cancer diagnosis comprising the methylated 5' UTR or methylated exon 1 region of the lung cancer-specific expression-decreased gene PCDHGA12 (GenBank NM_032094, protocadherin gamma subfamily A, 12).

In the present invention, the methylated 5' UTR (untranslated region) or methylated exon 1 region preferably contains at least one methylated CpG dinucleotide, and the 5'UTR and exon 1 regions are preferably represented by SEQ ID NO: 436.

An example of a method of screening a methylation marker gene may be a method comprising the steps of: (1) selecting DNA-hypermethylated genes only from a transformed cell line among a transformed cell line and a non-transformed cell line; (2) comparing gene expression profiles of the transformed lung cancer cells and the non-transformed cells adjacent thereto, and generating a list of genes which are more highly expressed in the non-transformed cells; (3) treating the transformed lung cancer line with a methylation inhibitor, and generating a list of genes which are more highly expressed in the transformed lung cancer cell line treated with the methylation inhibitor, compared to non-treated transformed lung cancer cell line; and (4) comparing the gene lists obtained in steps (1), (2) and (3), and regarding a gene, present in all the three lists, as a marker gene which is regulated by methylation in the genome of cells being converted from a non-transformed state to a transformed lung cancer cell form.

In the present invention, the lung cancer-specific expression-decreased gene PCDHGA12 screened from the genomic DNA of lung cancer cell lines by the above screening method has methylated CpG islands in the 5' UTR and exon 1 regions.

In another aspect the present invention relates to a biomarker, which contains one or more methylated CpG islands and is represented by any one base sequence of SEQ ID NOs: 437 and 438.

In the present invention, the DNA fragment is preferably derived from the lung cancer-specific expression-decreased gene PCDHGA12 (GenBank NM_032094, protocadherin gamma subfamily A, 12).

In the present invention, the 5' UTR and exon 1 regions of the lung cancer-specific expression-decreased gene PCDHGA12 has methylation at R1 (SEQ ID NO: 437), R2 (SEQ ID NO: 438) and R3 (SEQ ID NO: 439) regions in the lung cancer cell line.

In one Example of the present invention, the R1, R2 and R3 of PCDHGA12 gene in the lung cancer tissues from lung cancer patients showed very high methylation levels, and the methylation of the R1 region in paired lung cancer tissues and normal tissues adjacent thereto was shown to be high in 34 of 40 clinical samples (i.e., 85% of the clinical samples), and the methylation of the R3 region in these tissues was high in 36 of clinical samples (i.e., 90% of the clinical samples). This suggests that lung cancer can be efficiently diagnosed by measuring the hypermethylation of the R1, R2 and R3 regions of PCDHGA12 gene.

In another aspect, the present invention relates to a method for detecting CpG methylation of PCDHGA12 (protocadherin gamma subfamily A, 12), the method comprising the steps of:
  (a) isolating a genomic DNA from a clinical sample;
  (b) treating the genomic DNA from step (a) with bisulfite; and
  (c) determining hypermethylation of the CpG of the PCDHGA12 gene in the bisulfite-treated genomic DNA from step (b) by using primer(s) to amplify a methylated CpG of the bisulfite-treated PCDHGA12 gene.

In another aspect, the present invention relates to a method for detecting CpG methylation of PCDHGA12 for lung cancer diagnosis, the method comprising the steps of:
  (a) isolating a genomic DNA from a clinical sample;
  (b) treating the genomic DNA from step (a) with bisulfite; and
  (c) determining hypermethylation of the CpG of the PCDHGA12 gene in the bisulfite-treated genomic DNA from step (b) by using primer(s) to amplify a methylated CpG of the bisulfite-treated PCDHGA12 gene, wherein a lung cancer is detected in the human subject based on increased CpG methylation of the PCDHGA12 gene relative to that of a control.

In another aspect, the present invention relates to a method for detecting lung cancer or the stage of its progression, the method comprising the steps of: (a) isolating DNA from a clinical sample; and (b) detecting methylation of the 5'UTR or exon 1 region of PCDHGA12 (GenBank NM_032094, protocadherin gamma subfamily A, 12) gene in the isolated DNA.

In the present invention, the detection of methylation is preferably performed in a DNA region having a sequence selected from the group consisting of SEQ ID NO: 436, SEQ ID NO: 437, SEQ ID NO: 438 and SEQ ID NO: 439.

In the present invention, the detection of methylation is preferably performed using a method selected from the group consisting of PCR, methylation-specific PCR, real-time methylation-specific PCR, PCR using methylated DNA-specific binding proteins, quantitative PCR, a DNA chip-based detection method, pyrosequencing and bisulfite sequencing, and the clinical sample is a tissue, cell, blood or urine from a patient suspected of cancer or a subject to be diagnosed.

In an embodiment of the present disclosure, primer(s) that could amplify a methylated CpG of PCDHGA12 might be used, and such primer(s) comprises at least one or more CpG dinucleotide in a region which hybridizes to the methylated CpG of PCDHGA12 Specifically, the primer(s) for amplifying a methylated CpG of PCDHGA12 comprise sequence(s) having a homology of 50% or more with sequence(s) selected from the group consisting of SEQ ID NOs: 1, 2, 4-61, 63-103, 105-124, 126-139, 141-198, 200-222, 224-239, 241-243, 245-302, 304-361, 363-367, 369-394, and 396-434. Preferably, the primer(s) for amplifying a methylated CpG of PCDHGA12 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 1, 2, 4-61, 63-103, 105-124, 126-139, 141-198, 200-222, 224-239, 241-243, 245-302, 304-361, 363-367, 369-394, and 396-434.

If required, probe(s) capable of hybridizing with a methylated CpG of PCDHGA12 might be used. The probe(s) capable of hybridizing with a methylated CpG of PCDHGA12 comprise at least one or more CpG dinucleotide in a region which hybridizes to the methylated CpG of PCDHGA12. Specifically, probe(s) might comprise sequence(s) having a homology of 50% or more with sequence(s) selected from the group consisting of SEQ ID NOs: 3, 62, 104, 125, 140, 199, 223, 240, 244, 303, 362, 368, 395 and 435. Preferably, the probe(s) capable of hybridizing with a methylated CpG of PCDHGA12 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 3, 62, 104, 125, 140, 199, 223, 240, 244, 303, 362, 368, 395 and 435.

By a method of screening methylation biomarker genes, used in Examples of the present invention, not only lung cancer, but also genes which are differentially methylated at various dysplastic stages of tissue that progresses to lung cancer, can be screened. The screened genes can be used for lung cancer screening, risk-assessment, prognosis, disease identification, the diagnosis of disease stages, and the selection of therapeutic targets.

The identification of genes that are methylated in lung cancer and abnormalities at various stages of lung cancer makes it possible to early diagnose lung cancer in an accurate and effective manner and allows methylation profiling of multiple genes and the identification of new targets for therapeutic intervention. Furthermore, the methylation data according to the present invention may be combined with other non-methylation related biomarker detection methods to obtain a more accurate system for lung cancer diagnosis.

According to the method of the present invention, the progression of lung cancer at various stages or phases can be diagnosed by determining the methylation stage of one or more nucleic acid biomarkers obtained from a sample. By comparing the methylation stage of a nucleic acid isolated from a sample at each stage of lung cancer with the methylation stage of one or more nucleic acids isolated from a sample in which there is no cell proliferative abnormality of lung tissue, a specific stage of lung cancer in the sample can be detected. Herein, the methylation stage may be hypermethylation.

In one embodiment of the present invention, nucleic acid may be methylated in the regulatory region of a gene. In another embodiment, a gene which is involved in cell transformation can be diagnosed by detecting methylation outside of the regulatory region of the gene, because methylation proceeds inwards from the outside of the gene.

In yet another embodiment of the present invention, the abnormal growth (dysplasia) of lung tissue cells in a sample can be diagnosed by detecting the methylation state of the 5'UTR and exon 1 regions of PCDHGA12 (NM_032094, protocadherin gamma subfamily A, 12) gene using a kit.

The use of the diagnostic kit of the present invention can determine the abnormal growth (dysplasia progression) of lung tissue cells in a sample. The diagnostic method of the present invention comprises determining the methylation state of one or more nucleic acids isolated from a sample, wherein the methylation stage of said one or more nucleic acids is compared with the methylation stage of a nucleic acid isolated from a sample in which there is no abnormal growth (dysplasia) of lung tissue cells.

In still another embodiment of the present invention, the use of the methylated gene marker allows early diagnosis of cells that are likely to form lung cancer. When a gene determined to be methylated in cancer cells is methylated in clinically or morphologically normal-appearing cells, this indicates that the normal-appearing cells progress to carcinogenesis. Thus, lung cancer can be diagnosed at an early stage by detecting the methylation of the 5'UTR and exon 1 region of a lung cancer-specific gene in normal-appearing cells.

The use of the methylated marker gene of the present invention allows detection of the abnormal growth (dysplastic progression) of lung tissue cells in a sample. The detection method of the present invention comprises bringing a sample comprising at least one nucleic acid isolated from a clinical sample into contact with at least one agent capable of determining the methylation state of the nucleic acid, wherein the methylation of the nucleic acid differs from the methylation state of the same region of a nucleic acid preset in a sample in which there is no abnormal growth (dysplastic progression) of lung cells.

In yet another embodiment of the present invention, the likelihood of progression of lung cancer can be diagnosed by examining the methylation of the 5'UTR and exon 1 region of the marker gene in a sample showing a normal phenotype using the above-described kit. The sample may be solid or liquid tissue, cells, urine, serum or plasma.

In the present invention, the method of detecting the methylation of the 5' UTR and exon 1 regions of PCDHGA12 gene comprises the steps of: (a) isolating sample DNA from a clinical sample; (b) treating the isolated DNA with bisulfite; (c) amplifying the treated DNA using primers capable of amplifying a fragment comprising the CpG of the 5'UTR and exon 1 regions of PCDHGA12 gene; and (d) subjecting the product amplified in step (c) to pyrosequencing to determine the methylation of the PCDHGA12 gene.

In one embodiment of the present invention, the detection method can be carried out using a kit. The kit that is used in the present invention comprises: carrier means compartmentalized to receive a sample therein; and one or more containers including a first container containing a reagent that sensitively cleaves unmethylated cytosine, a second container containing primers for amplifying a CpG-containing nucleic acid, and a third containing a means for detecting the presence of a cleaved or uncleaved nucleic acid. The primers that are used in the present invention include sequences set forth in SEQ ID NOs: 1, 2, 4-61, 63-103, 105-124, 126-139, 141-198, 200-222, 224-239, 241-243, 245-302, 304-361, 363-367, 369-394, and 396-434, and any functional combination and fragments thereof. The carrier means are suited for containing one or more container means such as vials, tubes, and the like, each of the container means comprising one of the separate elements to be used in the method of the present invention. In view of the description provided herein of the inventive method, those of skill in the art can readily determine the apportionment of the necessary reagents among the container means. For example, one of the container means can comprise a container containing a methylation-sensitive restriction enzyme. One or more container means can also include a primer complementary to the nucleic acid locus of interest. In addition, one or more container means can also contain an isoschizomer of said methylation sensitive restriction enzyme.

In still embodiment of the present invention, the method of detecting lung cancer using the kit comprises the steps of: (1) isolating genomic DNA from a clinical sample; (2) treating the isolated genomic DNA with a methylation-sensitive restriction enzyme; (3) amplifying the treated genomic DNA using primers capable of amplifying the biomarker for lung cancer diagnosis of the present invention; and (4) determining the presence or absence of the biomarker for lung cancer diagnosis in the product amplified. In the method, a sample in which the biomarker fragment is present can be diagnosed as lung cancer or a lung cancer progression stage. In order to determine the presence or absence of a PCR amplification product, the kit may additionally contain a fragment capable of hybridizing with the biomarker for lung cancer diagnosis under strict conditions.

Also, methods of determining the presence or absence of the biomarker for lung cancer diagnosis, which can be used in the present invention, include bisulfite sequencing, pyrosequencing, methylation-specific PCR, MethyLight, PCR using methylated DNA binding proteins, and DNA chip assays.

As used herein, the term "cell transformation" refers to the change in characteristics of a cell from one form to another form such as from normal to abnormal, non-tumorous to tumorous, undifferentiated to differentiated, stem cell to non-stem cell. Furthermore, the transformation may be recognized by the morphology, phenotype, biochemical characteristics and the like of a cell.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island. As used herein, the term "sample" or "clinical sample" is referred to in its broadest sense, and includes any biological sample obtained from an individual, body fluid, a cell line, a tissue culture, depending on the type of assay that is to be performed. Methods for obtaining tissue biopsies and body fluids from mammals are well known in the art. A tissue biopsy of the lungs is a preferred source.

Screening of Methylation Biomarker

In the present invention, there was screened a biomarker gene methylated when a cell or tissue was transformed or when the cell morphology changed. As used herein, the term "transformation" refers to the change in morphology of a cell or tissue from one form to another form such as from normal to abnormal state, non-tumorous to timorous state, or undifferentiated to differentiated state.

Accordingly to the present invention, a biomarker gene methylated in transformation into lung cancer cells was systematically screened. For example, the method of screening the biomarker gene may be a method comprising the steps of: (1) selectively isolating only methylated DNAs from a transformed cell line and a non-transformed cell line using the methylation-specific binding protein MBD2bt; (2) amplifying each of the DNAs and labeling the amplified DNAs with a fluorescent dye; (3) hybridizing each of the labeled DNAs to a microarray capable of measuring methylation; (4) selecting genes hypermethylated in the transformed cells, based on the results of the hybridization; (5) comparing gene expression profiles of transformed lung cancer cells and non-transformed cells adjacent thereto, and generating a list of genes which are more highly expressed in the non-transformed cells; (6) treating the transformed lung cancer line with a methylation inhibitor, and generating a list of genes which are more highly expressed in the treated transformed lung cancer compared to the non-treated transformed lung cancer line; and (7) comparing the gene profiles obtained in steps (5) and (6), and regarding a gene, present in all the three gene lists, as a marker gene which is regulated by methylation in the genome of cells being converted from a non-transformed state to a transformed lung cancer cell form.

The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. It is apparent to those of skill in the art, when the nucleic acid is RNA, the deoxynucleotides A, G, C, and T are replaced by the ribonucleotides A, G, C, and U, respectively.

Any nucleic acid may be used in the present invention, given the presence of differently methylated CpG islands can be detected therein. The CpG island is a CpG-rich region in a nucleic acid sequence.

Methylation

In the present invention, any nucleic acid sample, in purified or nonpurified form, can be used, provided it contains or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

In general, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

A nucleic acid can contain a regulatory region which is a region of DNA that encodes information or controls transcription of the nucleic acid. Regulatory regions include at least one promoter. A "promoter" is a minimal sequence sufficient to direct transcription, and renders promoter-dependent gene expression controllable for cell-type specific, tissue-specific, or inducible by external signals or agents. Promoters may be located in the 5' or 3' region of the gene. The number of nucleic acids in all or part of promoter regions can be used to measure CG-island methylation. Moreover, it is generally recognized that methylation of the target gene promoter proceeds naturally from the outer boundary inward. Therefore, an early stage of cell conversion can be detected by analyzing methylation in these outer areas of the promoter region.

Nucleic acids isolated from a subject are obtained in a biological sample from the subject. If it is desired to detect lung cancer or stages of lung cancer progression, the nucleic acid may be isolated from lung tissue by scraping or biopsy. Such samples may be obtained by various medical procedures known to those of skill in the art.

As used herein, the term "hypermethylation" indicates that the methylation at a specific CpG location of tumor cells or in a specific base sequence region consisting of CpG islands is higher than that in normal cells.

Sample

The present invention describes early detection of lung cancer and employs lung cancer-specific gene methylation. The present inventors have found that lung cancer-specific gene methylation also occurs in tissue adjacent to the tumor region. Therefore, in a method for early detection of lung cancer, any sample, including liquid or solid tissue, may be examined for the presence of methylation of the lung cancer-specific gene. Such samples include, but not limited to, sputum, serum or plasma.

Method for Detection of Methylation

Detection of Differential Methylation—Methylation-Specific PCR

When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Detection of Differential Methylation—Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

Detection of Differential Methylation—Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

Detection of Differential Methylation—PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation—Methylation-Sensitive Restriction Enzyme

Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present invention are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present invention are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

Detection of Differential Methylation—Bisulfite Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Substrates

After the target nucleic acid region has been amplified, the nucleic acid amplification product can be hybridized to a known gene probe attached to a solid support (substrate) to detect the presence of the nucleic acid sequence.

As used herein, the term "substrate", when used in reference to a substance, structure, surface or material, means a composition comprising a nonbiological, synthetic, nonliving, planar or round surface that is not heretofore known to comprise a specific binding, hybridization or catalytic recognition site or a plurality of different recognition sites or a number of different recognition sites which exceeds the number of different molecular species comprising the surface, structure or material. Examples of the substrate include, but are not limited to, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes silicon, silicates, glass, metals and ceramics; and wood, paper, cardboard, cotton, wool, cloth, woven and nonwoven fibers, materials and fabrics; and amphibious surfaces.

It is known in the art that several types of membranes have adhesion to nucleic acid sequences. Specific non-limiting examples of these membranes include nitrocellulose or other membranes used for detection of gene expression such as polyvinylchloride, diazotized paper and other commercially available membranes such as GENE-SCREEN™, ZETAPROBE™ (Biorad), and NYTRAN™. Beads, glass, wafer and metal substrates are also included. Methods for attaching nucleic acids to these objects are well known in the art. Alternatively, screening can be done in a liquid phase.

Hybridization Conditions

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions).

Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

Kit

The present invention relates to a kit useful for the detection of abnormal cell growth in a subject. The kit of the present invention comprises a carrier means compartmentalized to receive a sample therein, one or more containers comprising a first container containing a reagent which sensitively cleaves unmethylated cytosine, a second container containing primers for amplification of a CpG-containing nucleic acid, and a third container containing a means to detect the presence of cleaved or uncleaved nucleic acid.

In an embodiment of the present disclosure, primer(s) contemplated for use in accordance with the present invention that could amplify a methylated CpG of PCDHGA12 might be used, and such primer(s) comprises at least one or more CpG dinucleotide in a region which hybridizes to the methylated CpG of PCDHGA12 Specifically, the primer(s) for amplifying a methylated CpG of PCDHGA12 comprise sequence(s) having a homology of 50% or more with sequence(s) selected from the group consisting of SEQ ID NOs: 1, 2, 4-61, 63-103, 105-124, 126-139, 141-198, 200-222, 224-239, 241-243, 245-302, 304-361, 363-367, 369-394, and 396-434. Preferably, the primer(s) for amplifying a methylated CpG of PCDHGA12 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 1, 2, 4-61, 63-103, 105-124, 126-139, 141-198, 200-222, 224-239, 241-243, 245-302, 304-361, 363-367, 369-394, and 396-434.

If required, probe(s) capable of hybridizing with a methylated CpG of PCDHGA12 might be used. The probe(s) capable of hybridizing with a methylated CpG of PCDHGA12 comprise at least one or more CpG dinucleotide in a region which hybridizes to the methylated CpG of PCDHGA12. Specifically, probe(s) might comprise sequence(s) having a homology of 50% or more with sequence(s) selected from the group consisting of SEQ ID NOs: 3, 62, 104, 125, 140, 199, 223, 240, 244, 303, 362, 368, 395 and 435. Preferably, the probe(s) capable of hybridizing with a methylated CpG of PCDHGA12 comprise sequence(s) having a homology of at least 60%, 70%, 80%, 90%, 91%, 92%, 93%, 94%, 95%, 96%, 97%, 98%, 99% and 100% with sequence(s) selected from the group consisting of SEQ ID NOs: 3, 62, 104, 125, 140, 199, 223, 240, 244, 303, 362, 368, 395 and 435.

Primers contemplated for use in accordance with the present invention include sequences set forth in SEQ ID NOS: 440 to 456, and any functional combination and fragments thereof. Functional combination or fragment is used as a primer to detect whether methylation has occurred on the region of the genome.

Carrier means are suited for containing one or more container means such as vials, tubes, and the like, each of the container means comprising one of the separate elements to be used in the method. In view of the description provided herein of the inventive method, those of skill in the art can readily determine the apportionment of the necessary reagents among the container means. For example, one of the container means can comprise a container containing a methylation-sensitive restriction enzyme. One or more container means can comprise a primer complementary to the nucleic acid locus of interest. In addition, one or more container means can contain an isoschizomer of the methylation sensitive restriction enzyme.

EXAMPLES

Hereinafter, the present invention will be described in further detail with reference to examples. It is to be understood, however, that these examples are for illustrative purposes only and are not to be construed to limit the scope of the present invention.

Example 1: Selection of Genes Hypermethylated in Lung Cancer Cell Line

Genes hypermethylated in lung cancer were selected in the following manner using the lung cancer cell line A549 (Korean Cell Line Bank (KCLB) 10185) and the normal lung cell line NHBE (Cambrex cc-2541).

First, 500 μg of of gDNA of each cell line was sonicated to a size of 300-400 bp (Vibra Cell, SONICS), and methylated DNA was selectively enriched from each cell line using Methylcapture™ (Genomictree, Korea) according to the manufacturer's protocol. The enriched methylated DNAs were amplified using a GenomePlex® Complete Whole Genome Amplification Kit (Sigma), and then each of the amplified methylated DNAs derived from A549 and NHBE was labeled with Cy5-dUTP and Cy3-dUTP, respectively and mixed. Then, the DNAs were hybridized to a CpG microarray (Agilent) containing CpG probes representing about 27,800 CpG islands present in the human genome according to the Agilent' protocol, followed by scanning. Next, candidate genes hypermethylated in A549 were selected by a statistical technique (FIG. 1 and Table 1).

TABLE 1

List of genes hypermethylated in A549 lung cancer cell line

| Gene symbol | Genbank Acc. No. |
|---|---|
| ADAMTS20 | NM_175851 |
| BARHL2 | NM_020063 |
| C14orf39 | NM_174978 |
| CCDC8 | NM_032040 |
| CFL1-MUS81 | NM_005507 |
| CLDN11 | NM_005602 |
| CNIH3 | NM_152495 |
| CORO6 | NM_032854 |
| CPT1C | NM_152359 |
| DBX1 | NM_001029865 |
| DNMT3A | NM_153759 |
| DPP6 | NM_001936 |
| EN1 | NM_001426 |
| EPSTI1 | NM_033255 |
| GLUL | NM_001033056 |
| GNAL | NM_002071 |
| GRHL2 | NM_024915 |
| HKR1 | NM_181786 |
| HLX1 | NM_021958 |
| HOXA11 | NM_005523 |
| HOXA5 | NM_019102 |
| HOXA6 | NM_024014 |
| HOXA7 | NM_006896 |
| HOXA9 | NM_152739 |
| HOXB5 | NM_002147 |
| HOXC11 | NM_014212 |
| HOXD12 | NM_021193 |
| HOXD8 | NM_019558 |
| IRX5 | NM_005853 |
| LHX1 | NM_005568 |
| LMX1A | NM_177398 |
| MEGF10 | NM_032446 |
| MOS | NM_005372 |
| PCDHGA12 | NM_003735 |
| PCDHGA5 | NM_032054 |
| PCDHGC3 | NM_032402 |
| PLCXD3 | NM_001005473 |
| POU4F3 | NM_002700 |
| PRAC | NM_032391 |
| PTGER4 | NM_000958 |
| RGMA | NM_020211 |
| RTKN | NM_033046 |

TABLE 1-continued

List of genes hypermethylated in A549 lung cancer cell line

| Gene symbol | Genbank Acc. No. |
|---|---|
| TAC1 | NM_003182 |
| TBX5 | NM_080718 |
| TGIF2 | NM_021809 |
| TLX3 | NM_021025 |
| WNK3 | NM_020922 |
| WNT3 | NM_030753 |
| ZNF560 | NM_152476 |
| ZNF577 | NM_032679 |

Example 2: Selection of Genes Whose Expression was Repressed by Methylation in Lung Cancer Tissue To select genes whose expression is repressed by methylation in lung cancer tissue, microarray hybridization was performed using a standard protocol (Schena et al., *Science*, 270:467, 1995).

Tumor-adjacent tissue and tumor tissue were isolated from lung cancer patients so as to be paired, and total RNA was isolated from the tissues. In order to indirectly compare the gene expression levels of the paired tumor-adjacent normal tissues and tumor tissues, reference RNA (indirect comparison) was prepared. To construct the reference RNA, total RNA was isolated from the following eleven human cancer cell lines: lung cancer cell line A549 (Korean Cell Line Bank (KCLB) 10185), gastric cancer cell line AGS (KCLB 21739), renal cancer cell line Caki-2 (KCLB 30047), colon cancer cell line HCT116 (KCLB 10247), cervical cancer cell line Hela (KCLB 10002), blood cancer cell lines HK-60 (KCLB 10240) and HT1080 (KCLB 10121), breast cancer cell line MDA-MB231 (KCLB 30026), liver cancer cell line SK-hep1 (KCLB 30052), T-cell-derived cell line Molt-4 (KCLB 21582), and brain cancer cell line U-87MG (KCLB 30014). The total RNAs from the cell lines and lung tissue were isolated using Tri-Reagent (Sigma, USA).

To prepare the reference RNA, the equal amounts of the total RNAs from 11 cell lines were mixed and used as an internal control.

To compare the relative gene expression levels of the paired tumor-adjacent tissue and tumor tissue, the RNAs isolated from the tumor-adjacent normal tissues and the tumor tissues were compared with the reference RNA. For this purpose, 100 μg of each total RNA was labeled with Cy3-dUTP or Cy5-dUTP. The reference RNA was labeled with Cy3, and the RNAs isolated from lung tissues was labeled with Cy5. The Cy3- and Cy5-labeled cDNAs were purified using a PCR purification kit (Qiagen, Germany), mixed, and concentrated to a final volume of 27 μl using Microcon YM-30 (Millipore Corp., USA).

80 μl of a hybridization reaction solution (27 μl of the labeled cDNA target, 20 μl 20×SSC, 1% SDS 8%, 24 μl formamide (Sigma, USA) and 20 μg human Cott DNA (Invitrogen Corp., USA)) was heated at 100° C. for 2 minutes, and immediately hybridized to a human 22K oligonucleotide microarray (GenomicTree, Inc., Korea). The hybridization was carried out in a humidity-controlled Hyb-Chamber X (GenomicTree, Inc., Korea) at 42° C. for 12-16 hours. After completion of the hybridization, the microarray slide was scanned using Axon 4000B (Axon Instrument Inc., USA). The signal and background fluorescence intensities were calculated for each probe spot by averaging the intensities of every pixel inside the target region using GenePix Pro 4.0 software (Axon Instruments Inc., USA). Spots showing obvious abnormalities were excluded from analysis. All data normalization, statistical analysis and cluster analysis were performed using GeneSpring 7.2 (Agilent, USA).

To determine the relative difference in gene expression levels between the tumor-adjacent normal tissues and tumor tissues, statistical analysis (ANOVA (p<0.01) for indirect comparison was performed. From the results of the statistical analysis, 252 genes were down-regulated in the tumor tissues compared to the paired tumor-adjacent tissues.

Example 3: Selection of Genes Up-Regulated by Demethylation

In order to examine whether the expression of the genes identified in Example 1 would be regulated by the promoter methylation of the genes, the lung cancer cell lines A549 (KCLB 10185) and NCI-H358 (KCLB 90358) were treated with 200 nM of the demethylating agent 5-aza-2'-deoxycytidine (DAC, Sigma, USA) for 3 days. Total RNAs were isolated from untreated and treated cell lines by Tri-reagent.

To determine gene expression changes caused by DAC treatment, the transcript level was compared directly between the untreated and treated cell lines. As a result, it was seen that 376 genes showed elevated expression when treated with DAC compared with the control group not treated with DAC. 252 tumor repressor genes obtained in Example 1 were compared with the above 367 genes up-regulated two times or more by demethylation, and as a result, 18 concurrent genes therebetween were identified (FIG. 1).

Example 4: Identification of PCDHGA12 Gene Hypermethylated in Lung Cancer

To confirm the presence of a CpG island in the promoter regions of the above-mentioned 18 genes, MethPrimer (http://itsa.ucsf.edu/~urolab/methprimer/index1.html) was used. Because 13 of the 18 genes had no CpG island, the 13 genes were excluded from the concurrent gene list. Accordingly, among the remaining 5 genes, the PCDHGA12 gene included in the 50 genes selected in the CpG microarray analysis in Example 1 was selected as a final lung cancer-related methylation biomarker. It could be seen that the selected PCDHGA12 gene was hypermethylated in the lung cancer cell line, down-regulated in lung tumor tissue, up-regulated in demethylation conditions, and contained CpG islands in the promoter, the 5'UTR and exon 1 regions (Table 2).

TABLE 2

Expression levels of PCDHGA12 gene in lung cancer tissue and lung cancer cell line

| gene | down-regulated degree in lung cancer tissue | | Re-expression levels in lung cancer cell line | |
|---|---|---|---|---|
| | average fold change | p-value | A549 | NCI-H358 |
| PCDHGA12 | 0.26 | <0.01 | 2.0 | 7.3 |

Example 5: Evaluation of the Ability of PCDHGA12 Gene to Diagnose Lung Cancer by Using qMSP In order to analyze the ability of PCDHGA12 gene to diagnose lung cancer, 407 sets of primers and probes, which could amplify whole CpG island of PCDHGA12 gene and detect methylation specific sites, were designed (Table 1) and methylation specific real time PCR (qMSP) was performed. To achieve the purpose, genomic DNA was isolated from 20 cases of normal lung tissues and lung cancer tissues. Treating bisulfite to the above isolated genome DNA by using EZ DNA methylation-Gold kit (Zymo Research, USA), and the DNA was subjected to methylation specific real time PCR (qMSP) by eluting with 10 µl distilled water. The qMSP was performed with bisulfite treated genome DNA as a template by using methylation specific primers and probes designed according to Table 1. qMSP used Rotor-Gene Q PCR equipment (Qiagen). Total 20 µl PCR reaction solution (template DNA, 2 µl; 5× AptaTaq DNA Master (Roche Diagnostics), 4 µl; PCR primers, 2 µl (2 pmole/µl), TaqMan probe, 2 µl (2 pmole/µl); D. W. 10 µl) was prepared. Total 40 times of PCR, in which the condition is treated at 95° C. for 5 minutes, at 95° C. for 15 seconds and at annealing temperature (58° C.-61° C.) for 1 minute, were performed. The amplification of the PCR product was confirmed by measuring the Ct (cycling threshold) value. Methylated and non-methylated control DNAs were tested with sample DNA by using EpiTect PCR control DNA set (Qiagen, cat. no. 59695). COL2A1 gene (Kristensen et al., 2008) was used as an internal control, and A549 cell strain genomic DNA, in which the PCDHGA12 gene is completely methylated, was used as methylation positive standard substance. The methylation level of each sample was measured by PMR value and the PMR value was calculated as follows:

$$PMR = 2^{-\Delta\Delta Ct} \times 100, \Delta\Delta Ct = [(Ct_{(PCDHGA12)} - Ct_{(COL2A1)sample})] - [(Ct_{(PCDHGA12)} - Ct_{(COL2A1)A549})]$$

Sensitivity and specificity for set of respective primers and probes were calculated with ROC curve analysis (MedCalc program, Belgium). (Table 2).

TABLE 3

Sequences of primer and probes for PCDHGA12 gene qMSP

| Set | Primer | Sequence (5'→3') | Size of amplified product (bp) | Sequence No. |
|---|---|---|---|---|
| 1 | F1-1 | AAAGGTTGTTTATT | 140 | 1 |
| | R1 | CGCTCGCGCGATAC | | 2 |
| | Probe1 | ACGTATTAGCGTTTGTTTAGTTCGA | | 3 |
| 2 | F1-2 | AAGGTTGTTTATTA | 139 | 4 |
| | R1 | CGCTCGCGCGATAC | | 2 |
| | Probe1 | ACGTATTAGCGTTTGTTTAGTTCGA | | 3 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 3 | F1-3 | AGGTTGTTTATTAT | 138 | 5 |
|  | R1 | CGCTCGCGCGATAC |  | 2 |
|  | Probe1 | ACGTATTAGCGTTTGTTTAGTTCGA |  | 3 |
| 4 | F1-4 | GGTTGTTTATTATT | 137 | 6 |
|  | R1 | CGCTCGCGCGATAC |  | 2 |
|  | Probe1 | ACGTATTAGCGTTTGTTTAGTTCGA |  | 3 |
| 5 | F1-5 | GTTGTTTATTATTT | 136 | 7 |
|  | R1 | CGCTCGCGCGATAC |  | 2 |
|  | Probe1 | ACGTATTAGCGTTTGTTTAGTTCGA |  | 3 |
| 6 | F1-6 | TTGTTTATTATTTG | 135 | 8 |
|  | R1 | CGCTCGCGCGATAC |  | 2 |
|  | Probe1 | ACGTATTAGCGTTTGTTTAGTTCGA |  | 3 |
| 7 | F1-7 | TGTTTATTATTTGG | 134 | 9 |
|  | R1 | CGCTCGCGCGATAC |  | 2 |
|  | Probe1 | ACGTATTAGCGTTTGTTTAGTTCGA |  | 3 |
| 8 | F1-8 | GTTTATTATTTGGT | 133 | 10 |
|  | R1 | CGCTCGCGCGATAC |  | 2 |
|  | Probe1 | ACGTATTAGCGTTTGTTTAGTTCGA |  | 3 |
| 9 | F1-9 | TTTATTATTTGGTT | 132 | 11 |
|  | R1 | CGCTCGCGCGATAC |  | 2 |
|  | Probe1 | ACGTATTAGCGTTTGTTTAGTTCGA |  | 3 |
| 10 | F1-10 | TTATTATTTGGTTT | 131 | 12 |
|  | R1 | CGCTCGCGCGATAC |  | 2 |
|  | Probe1 | ACGTATTAGCGTTTGTTTAGTTCGA |  | 3 |
| 11 | F1-11 | TATTATTTGGTTTT | 130 | 13 |
|  | R1 | CGCTCGCGCGATAC |  | 2 |
|  | Probe1 | ACGTATTAGCGTTTGTTTAGTTCGA |  | 3 |
| 12 | F1-12 | ATTATTTGGTTTTT | 129 | 14 |
|  | R1 | CGCTCGCGCGATAC |  | 2 |
|  | Probe1 | ACGTATTAGCGTTTGTTTAGTTCGA |  | 3 |
| 13 | F1-13 | TTATTTGGTTTTTA | 128 | 15 |
|  | R1 | CGCTCGCGCGATAC |  | 2 |
|  | Probe1 | ACGTATTAGCGTTTGTTTAGTTCGA |  | 3 |
| 14 | F1-14 | TATTTGGTTTTTAC | 127 | 16 |
|  | R1 | CGCTCGCGCGATAC |  | 2 |
|  | Probe1 | ACGTATTAGCGTTTGTTTAGTTCGA |  | 3 |
| 15 | F1-15 | ATTTGGTTTTTACG | 126 | 17 |
|  | R1 | CGCTCGCGCGATAC |  | 2 |
|  | Probe1 | ACGTATTAGCGTTTGTTTAGTTCGA |  | 3 |
| 16 | F1-16 | TTTGGTTTTTACGG | 125 | 18 |
|  | R1 | CGCTCGCGCGATAC |  | 2 |
|  | Probe1 | ACGTATTAGCGTTTGTTTAGTTCGA |  | 3 |
| 17 | F1-17 | TTGGTTTTTACGGT | 124 | 19 |
|  | R1 | CGCTCGCGCGATAC |  | 2 |
|  | Probe1 | ACGTATTAGCGTTTGTTTAGTTCGA |  | 3 |
| 18 | F1-18 | TGGTTTTTACGGTT | 123 | 20 |
|  | R1 | CGCTCGCGCGATAC |  | 2 |
|  | Probe1 | ACGTATTAGCGTTTGTTTAGTTCGA |  | 3 |
| 19 | F1-19 | GGTTTTTACGGTTT | 122 | 21 |
|  | R1 | CGCTCGCGCGATAC |  | 2 |
|  | Probe1 | ACGTATTAGCGTTTGTTTAGTTCGA |  | 3 |
| 20 | F1-20 | GTTTTTACGGTTTT | 121 | 22 |
|  | R1 | CGCTCGCGCGATAC |  | 2 |
|  | Probe1 | ACGTATTAGCGTTTGTTTAGTTCGA |  | 3 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 21 | F1-21 | TTTTTACGGTTTTC | 120 | 23 |
|  | R1 | CGCTCGCGCGATAC |  | 2 |
|  | Probe1 | ACGTATTAGCGTTTGTTTAGTTCGA |  | 3 |
| 22 | F1-22 | TTTTACGGTTTTCG | 119 | 24 |
|  | R1 | CGCTCGCGCGATAC |  | 2 |
|  | Probe1 | ACGTATTAGCGTTTGTTTAGTTCGA |  | 3 |
| 23 | F1-23 | TTTACGGTTTTCGA | 118 | 25 |
|  | R1 | CGCTCGCGCGATAC |  | 2 |
|  | Probe1 | ACGTATTAGCGTTTGTTTAGTTCGA |  | 3 |
| 24 | F1-24 | TTACGGTTTTCGAC | 117 | 26 |
|  | R1 | CGCTCGCGCGATAC |  | 2 |
|  | Probe1 | ACGTATTAGCGTTTGTTTAGTTCGA |  | 3 |
| 25 | F1-25 | TACGGTTTTCGACG | 116 | 27 |
|  | R1 | CGCTCGCGCGATAC |  | 2 |
|  | Probe1 | ACGTATTAGCGTTTGTTTAGTTCGA |  | 3 |
| 26 | F1-26 | ACGGTTTTCGACGG | 115 | 28 |
|  | R1 | CGCTCGCGCGATAC |  | 2 |
|  | Probe1 | ACGTATTAGCGTTTGTTTAGTTCGA |  | 3 |
| 27 | F1-27 | CGGTTTTCGACGGG | 114 | 29 |
|  | R1 | CGCTCGCGCGATAC |  | 2 |
|  | Probe1 | ACGTATTAGCGTTTGTTTAGTTCGA |  | 3 |
| 28 | F1-28 | GGTTTTCGACGGGG | 113 | 30 |
|  | R1 | CGCTCGCGCGATAC |  | 2 |
|  | Probe1 | ACGTATTAGCGTTTGTTTAGTTCGA |  | 3 |
| 29 | F1-29 | GTTTTCGACGGGGG | 112 | 31 |
|  | R1 | CGCTCGCGCGATAC |  | 2 |
|  | Probe1 | ACGTATTAGCGTTTGTTTAGTTCGA |  | 3 |
| 30 | F1-30 | TTTTCGACGGGGGC | 111 | 32 |
|  | R1 | CGCTCGCGCGATAC |  | 2 |
|  | Probe1 | ACGTATTAGCGTTTGTTTAGTTCGA |  | 3 |
| 31 | F1-31 | TTTCGACGGGGGCG | 110 | 33 |
|  | R1 | CGCTCGCGCGATAC |  | 2 |
|  | Probe1 | ACGTATTAGCGTTTGTTTAGTTCGA |  | 3 |
| 32 | F1-32 | TTCGACGGGGGCGA | 109 | 34 |
|  | R1 | CGCTCGCGCGATAC |  | 2 |
|  | Probe1 | ACGTATTAGCGTTTGTTTAGTTCGA |  | 3 |
| 33 | F1-33 | TCGACGGGGGCGAT | 108 | 35 |
|  | R1 | CGCTCGCGCGATAC |  | 2 |
|  | Probe1 | ACGTATTAGCGTTTGTTTAGTTCGA |  | 3 |
| 34 | F1-34 | CGACGGGGGCGATT | 107 | 36 |
|  | R1 | CGCTCGCGCGATAC |  | 2 |
|  | Probe1 | ACGTATTAGCGTTTGTTTAGTTCGA |  | 3 |
| 35 | F1-35 | GACGGGGGCGATTC | 106 | 37 |
|  | R1 | CGCTCGCGCGATAC |  | 2 |
|  | Probe1 | ACGTATTAGCGTTTGTTTAGTTCGA |  | 3 |
| 36 | F1-36 | ACGGGGGCGATTCG | 105 | 38 |
|  | R1 | CGCTCGCGCGATAC |  | 2 |
|  | Probe1 | ACGTATTAGCGTTTGTTTAGTTCGA |  | 3 |
| 37 | F1-37 | CGGGGGCGATTCGG | 104 | 39 |
|  | R1 | CGCTCGCGCGATAC |  | 2 |
|  | Probe1 | ACGTATTAGCGTTTGTTTAGTTCGA |  | 3 |
| 38 | F1-38 | GGGGGCGATTCGGT | 103 | 40 |
|  | R1 | CGCTCGCGCGATAC |  | 2 |
|  | Probe1 | ACGTATTAGCGTTTGTTTAGTTCGA |  | 3 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 39 | F1-39 | GGGGCGATTCGGTG | 102 | 41 |
|  | R1 | CGCTCGCGCGATAC |  | 2 |
|  | Probe1 | ACGTATTAGCGTTTGTTTAGTTCGA |  | 3 |
| 40 | F1-40 | GGGCGATTCGGTGC | 101 | 42 |
|  | R1 | CGCTCGCGCGATAC |  | 2 |
|  | Probe1 | ACGTATTAGCGTTTGTTTAGTTCGA |  | 3 |
| 41 | F1-41 | GGCGATTCGGTGCG | 100 | 43 |
|  | R1 | CGCTCGCGCGATAC |  | 2 |
|  | Probe1 | ACGTATTAGCGTTTGTTTAGTTCGA |  | 3 |
| 42 | F1-42 | GCGATTCGGTGCGT | 99 | 44 |
|  | R1 | CGCTCGCGCGATAC |  | 2 |
|  | Probe1 | ACGTATTAGCGTTTGTTTAGTTCGA |  | 3 |
| 43 | F1-43 | CGATTCGGTGCGTA | 98 | 45 |
|  | R1 | CGCTCGCGCGATAC |  | 2 |
|  | Probe1 | ACGTATTAGCGTTTGTTTAGTTCGA |  | 3 |
| 44 | F1-44 | GATTCGGTGCGTAT | 97 | 46 |
|  | R1 | CGCTCGCGCGATAC |  | 2 |
|  | Probe1 | ACGTATTAGCGTTTGTTTAGTTCGA |  | 3 |
| 45 | F1-45 | ATTCGGTGCGTATA | 96 | 47 |
|  | R1 | CGCTCGCGCGATAC |  | 2 |
|  | Probe1 | ACGTATTAGCGTTTGTTTAGTTCGA |  | 3 |
| 46 | F1-46 | TTCGGTGCGTATAG | 95 | 48 |
|  | R1 | CGCTCGCGCGATAC |  | 2 |
|  | Probe1 | ACGTATTAGCGTTTGTTTAGTTCGA |  | 3 |
| 47 | F1-47 | TCGGTGCGTATAGG | 94 | 49 |
|  | R1 | CGCTCGCGCGATAC |  | 2 |
|  | Probe1 | ACGTATTAGCGTTTGTTTAGTTCGA |  | 3 |
| 48 | F1-48 | CGGTGCGTATAGGT | 93 | 50 |
|  | R1 | CGCTCGCGCGATAC |  | 2 |
|  | Probe1 | ACGTATTAGCGTTTGTTTAGTTCGA |  | 3 |
| 49 | F1-49 | GGTGCGTATAGGTA | 92 | 51 |
|  | R1 | CGCTCGCGCGATAC |  | 2 |
|  | Probe1 | ACGTATTAGCGTTTGTTTAGTTCGA |  | 3 |
| 50 | F1-50 | GTGCGTATAGGTAT | 91 | 52 |
|  | R1 | CGCTCGCGCGATAC |  | 2 |
|  | Probe1 | ACGTATTAGCGTTTGTTTAGTTCGA |  | 3 |
| 51 | F1-51 | TGCGTATAGGTATC | 90 | 53 |
|  | R1 | CGCTCGCGCGATAC |  | 2 |
|  | Probe1 | ACGTATTAGCGTTTGTTTAGTTCGA |  | 3 |
| 52 | F1-52 | GCGTATAGGTATCG | 89 | 54 |
|  | R1 | CGCTCGCGCGATAC |  | 2 |
|  | Probe1 | ACGTATTAGCGTTTGTTTAGTTCGA |  | 3 |
| 53 | F1-53 | CGTATAGGTATCGC | 88 | 55 |
|  | R1 | CGCTCGCGCGATAC |  | 2 |
|  | Probe1 | ACGTATTAGCGTTTGTTTAGTTCGA |  | 3 |
| 54 | F1-54 | GTATAGGTATCGCG | 87 | 56 |
|  | R1 | CGCTCGCGCGATAC |  | 2 |
|  | Probe1 | ACGTATTAGCGTTTGTTTAGTTCGA |  | 3 |
| 55 | F1-55 | TATAGGTATCGCGC | 86 | 57 |
|  | R1 | CGCTCGCGCGATAC |  | 2 |
|  | Probe1 | ACGTATTAGCGTTTGTTTAGTTCGA |  | 3 |
| 56 | F1-56 | ATAGGTATCGCGCG | 85 | 58 |
|  | R1 | CGCTCGCGCGATAC |  | 2 |
|  | Probe1 | ACGTATTAGCGTTTGTTTAGTTCGA |  | 3 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 57 | F1-57 | TAGGTATCGCGCGT | 84 | 59 |
|  | R1 | CGCTCGCGCGATAC |  | 2 |
|  | Probe1 | ACGTATTAGCGTTTGTTTAGTTCGA |  | 3 |
| 58 | F2-1 | ATTCGCGTGATGGT | 140 | 60 |
|  | R2 | TTAACTCCTTCGTC |  | 61 |
|  | Probe2 | GTTTGTAGTTAACGTTATCGATTTT |  | 62 |
| 59 | F2-2 | TTCGCGTGATGGTT | 139 | 63 |
|  | R2 | TTAACTCCTTCGTC |  | 61 |
|  | Probe2 | GTTTGTAGTTAACGTTATCGATTTT |  | 62 |
| 60 | F2-3 | TCGCGTGATGGTTT | 138 | 64 |
|  | R2 | TTAACTCCTTCGTC |  | 61 |
|  | Probe2 | GTTTGTAGTTAACGTTATCGATTTT |  | 62 |
| 61 | F2-4 | CGCGTGATGGTTTT | 137 | 65 |
|  | R2 | TTAACTCCTTCGTC |  | 61 |
|  | Probe2 | GTTTGTAGTTAACGTTATCGATTTT |  | 62 |
| 62 | F2-5 | GCGTGATGGTTTTG | 136 | 66 |
|  | R2 | TTAACTCCTTCGTC |  | 61 |
|  | Probe2 | GTTTGTAGTTAACGTTATCGATTTT |  | 62 |
| 63 | F2-6 | CGTGATGGTTTTGGATGC | 135 | 67 |
|  | R2 | TTAACTCCTTCGTC |  | 61 |
|  | Probe2 | GTTTGTAGTTAACGTTATCGATTTT |  | 62 |
| 64 | F2-7 | GTGATGGTTTTGGATGC | 134 | 68 |
|  | R2 | TTAACTCCTTCGTC |  | 61 |
|  | Probe2 | GTTTGTAGTTAACGTTATCGATTTT |  | 62 |
| 65 | F2-8 | TTTTGGATGCGAAC | 127 | 69 |
|  | R2 | TTAACTCCTTCGTC |  | 61 |
|  | Probe2 | GTTTGTAGTTAACGTTATCGATTTT |  | 62 |
| 66 | F2-9 | TTTGGATGCGAACG | 126 | 70 |
|  | R2 | TTAACTCCTTCGTC |  | 61 |
|  | Probe2 | GTTTGTAGTTAACGTTATCGATTTT |  | 62 |
| 67 | F2-10 | TTGGATGCGAACGA | 125 | 71 |
|  | R2 | TTAACTCCTTCGTC |  | 61 |
|  | Probe2 | GTTTGTAGTTAACGTTATCGATTTT |  | 62 |
| 68 | F2-11 | TGGATGCGAACGAT | 124 | 72 |
|  | R2 | TTAACTCCTTCGTC |  | 61 |
|  | Probe2 | GTTTGTAGTTAACGTTATCGATTTT |  | 62 |
| 69 | F2-12 | GGATGCGAACGATA | 123 | 73 |
|  | R2 | TTAACTCCTTCGTC |  | 61 |
|  | Probe2 | GTTTGTAGTTAACGTTATCGATTTT |  | 62 |
| 70 | F2-13 | GATGCGAACGATAA | 122 | 74 |
|  | R2 | TTAACTCCTTCGTC |  | 61 |
|  | Probe2 | GTTTGTAGTTAACGTTATCGATTTT |  | 62 |
| 71 | F2-14 | ATGCGAACGATAAC | 121 | 75 |
|  | R2 | TTAACTCCTTCGTC |  | 61 |
|  | Probe2 | GTTTGTAGTTAACGTTATCGATTTT |  | 62 |
| 72 | F2-15 | TGCGAACGATAACG | 120 | 76 |
|  | R2 | TTAACTCCTTCGTC |  | 61 |
|  | Probe2 | GTTTGTAGTTAACGTTATCGATTTT |  | 62 |
| 73 | F2-16 | GCGAACGATAACGT | 119 | 77 |
|  | R2 | TTAACTCCTTCGTC |  | 61 |
|  | Probe2 | GTTTGTAGTTAACGTTATCGATTTT |  | 62 |
| 74 | F2-17 | CGAACGATAACGTA | 118 | 78 |
|  | R2 | TTAACTCCTTCGTC |  | 61 |
|  | Probe2 | GTTTGTAGTTAACGTTATCGATTTT |  | 62 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 75 | F2-18 | GAACGATAACGTAT | 117 | 79 |
|  | R2 | TTAACTCCTTCGTC |  | 61 |
|  | Probe2 | GTTTGTAGTTAACGTTATCGATTTT |  | 62 |
| 76 | F2-19 | AACGATAACGTATT | 116 | 80 |
|  | R2 | TTAACTCCTTCGTC |  | 61 |
|  | Probe2 | GTTTGTAGTTAACGTTATCGATTTT |  | 62 |
| 77 | F2-20 | ACGATAACGTATTA | 115 | 81 |
|  | R2 | TTAACTCCTTCGTC |  | 61 |
|  | Probe2 | GTTTGTAGTTAACGTTATCGATTTT |  | 62 |
| 78 | F2-21 | CGATAACGTATTAG | 114 | 82 |
|  | R2 | TTAACTCCTTCGTC |  | 61 |
|  | Probe2 | GTTTGTAGTTAACGTTATCGATTTT |  | 62 |
| 79 | F2-22 | GATAACGTATTAGC | 113 | 83 |
|  | R2 | TTAACTCCTTCGTC |  | 61 |
|  | Probe2 | GTTTGTAGTTAACGTTATCGATTTT |  | 62 |
| 80 | F2-23 | ATAACGTATTAGCG | 112 | 84 |
|  | R2 | TTAACTCCTTCGTC |  | 61 |
|  | Probe2 | GTTTGTAGTTAACGTTATCGATTTT |  | 62 |
| 81 | F2-24 | TAACGTATTAGCGT | 111 | 85 |
|  | R2 | TTAACTCCTTCGTC |  | 61 |
|  | Probe2 | GTTTGTAGTTAACGTTATCGATTTT |  | 62 |
| 82 | F2-25 | AACGTATTAGCGTT | 110 | 86 |
|  | R2 | TTAACTCCTTCGTC |  | 61 |
|  | Probe2 | GTTTGTAGTTAACGTTATCGATTTT |  | 62 |
| 83 | F2-26 | ACGTATTAGCGTTT | 109 | 87 |
|  | R2 | TTAACTCCTTCGTC |  | 61 |
|  | Probe2 | GTTTGTAGTTAACGTTATCGATTTT |  | 62 |
| 84 | F2-27 | CGTATTAGCGTTTG | 108 | 88 |
|  | R2 | TTAACTCCTTCGTC |  | 61 |
|  | Probe2 | GTTTGTAGTTAACGTTATCGATTTT |  | 62 |
| 85 | F2-28 | GTATTAGCGTTTGT | 107 | 89 |
|  | R2 | TTAACTCCTTCGTC |  | 61 |
|  | Probe2 | GTTTGTAGTTAACGTTATCGATTTT |  | 62 |
| 86 | F2-29 | CGTTTGTTTAGTTC | 100 | 90 |
|  | R2 | TTAACTCCTTCGTC |  | 61 |
|  | Probe2 | GTTTGTAGTTAACGTTATCGATTTT |  | 62 |
| 87 | F2-30 | GTTTGTTTAGTTCG | 99 | 91 |
|  | R2 | TTAACTCCTTCGTC |  | 61 |
|  | Probe2 | GTTTGTAGTTAACGTTATCGATTTT |  | 62 |
| 88 | F2-31 | TTAGTTCGAGTATC | 93 | 92 |
|  | R2 | TTAACTCCTTCGTC |  | 61 |
|  | Probe2 | GTTTGTAGTTAACGTTATCGATTTT |  | 62 |
| 89 | F2-32 | TAGTTCGAGTATCG | 92 | 93 |
|  | R2 | TTAACTCCTTCGTC |  | 61 |
|  | Probe2 | GTTTGTAGTTAACGTTATCGATTTT |  | 62 |
| 90 | F2-33 | AGTTCGAGTATCGC | 91 | 94 |
|  | R2 | TTAACTCCTTCGTC |  | 61 |
|  | Probe2 | GTTTGTAGTTAACGTTATCGATTTT |  | 62 |
| 91 | F2-34 | GTTCGAGTATCGCG | 90 | 95 |
|  | R2 | TTAACTCCTTCGTC |  | 61 |
|  | Probe2 | GTTTGTAGTTAACGTTATCGATTTT |  | 62 |
| 92 | F2-35 | TTCGAGTATCGCGC | 89 | 96 |
|  | R2 | TTAACTCCTTCGTC |  | 61 |
|  | Probe2 | GTTTGTAGTTAACGTTATCGATTTT |  | 62 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 93 | F2-36 | TCGAGTATCGCGCG | 88 | 97 |
|  | R2 | TTAACTCCTTCGTC |  | 61 |
|  | Probe2 | GTTTGTAGTTAACGTTATCGATTTT |  | 62 |
| 94 | F2-37 | CGAGTATCGCGCGA | 87 | 98 |
|  | R2 | TTAACTCCTTCGTC |  | 61 |
|  | Probe2 | GTTTGTAGTTAACGTTATCGATTTT |  | 62 |
| 95 | F2-38 | GAGTATCGCGCGAG | 86 | 99 |
|  | R2 | TTAACTCCTTCGTC |  | 61 |
|  | Probe2 | GTTTGTAGTTAACGTTATCGATTTT |  | 62 |
| 96 | F2-39 | AGTATCGCGCGAGC | 85 | 100 |
|  | R2 | TTAACTCCTTCGTC |  | 61 |
|  | Probe2 | GTTTGTAGTTAACGTTATCGATTTT |  | 62 |
| 97 | F2-40 | GTATCGCGCGAGCG | 84 | 101 |
|  | R2 | TTAACTCCTTCGTC |  | 61 |
|  | Probe2 | GTTTGTAGTTAACGTTATCGATTTT |  | 62 |
| 98 | F3-1 | CGGAGAATTTGGTTTTGGGTAC | 122 | 102 |
|  | R3 | AAAAACTTAAACCG |  | 103 |
|  | Probe3 | TTTTTTCGGTATGTGGACGATAAGG |  | 104 |
| 99 | F3-2 | GGAGAATTTGGTTTTGGGTAC | 121 | 105 |
|  | R3 | AAAAACTTAAACCG |  | 103 |
|  | Probe3 | TTTTTTCGGTATGTGGACGATAAGG |  | 104 |
| 100 | F3-3 | TAGTTAACGTTATC | 89 | 106 |
|  | R3 | AAAAACTTAAACCG |  | 103 |
|  | Probe3 | TTTTTTCGGTATGTGGACGATAAGG |  | 104 |
| 101 | F3-4 | AGTTAACGTTATCG | 88 | 107 |
|  | R3 | AAAAACTTAAACCG |  | 103 |
|  | Probe3 | TTTTTTCGGTATGTGGACGATAAGG |  | 104 |
| 102 | F3-5 | GTTAACGTTATCGA | 87 | 108 |
|  | R3 | AAAAACTTAAACCG |  | 103 |
|  | Probe3 | TTTTTTCGGTATGTGGACGATAAGG |  | 104 |
| 103 | F3-6 | TTAACGTTATCGAT | 86 | 109 |
|  | R3 | AAAAACTTAAACCG |  | 103 |
|  | Probe3 | TTTTTTCGGTATGTGGACGATAAGG |  | 104 |
| 104 | F3-7 | TAACGTTATCGATT | 85 | 110 |
|  | R3 | AAAAACTTAAACCG |  | 103 |
|  | Probe3 | TTTTTTCGGTATGTGGACGATAAGG |  | 104 |
| 105 | F3-8 | AACGTTATCGATTT | 84 | 111 |
|  | R3 | AAAAACTTAAACCG |  | 103 |
|  | Probe3 | TTTTTTCGGTATGTGGACGATAAGG |  | 104 |
| 106 | F3-9 | ACGTTATCGATTTT | 83 | 112 |
|  | R3 | AAAAACTTAAACCG |  | 103 |
|  | Probe3 | TTTTTTCGGTATGTGGACGATAAGG |  | 104 |
| 107 | F3-10 | CGTTATCGATTTTG | 82 | 113 |
|  | R3 | AAAAACTTAAACCG |  | 103 |
|  | Probe3 | TTTTTTCGGTATGTGGACGATAAGG |  | 104 |
| 108 | F3-11 | GTTATCGATTTTGA | 81 | 114 |
|  | R3 | AAAAACTTAAACCG |  | 103 |
|  | Probe3 | TTTTTTCGGTATGTGGACGATAAGG |  | 104 |
| 109 | F3-12 | TTATCGATTTTGAC | 80 | 115 |
|  | R3 | AAAAACTTAAACCG |  | 103 |
|  | Probe3 | TTTTTTCGGTATGTGGACGATAAGG |  | 104 |
| 110 | F3-13 | TATCGATTTTGACG | 79 | 116 |
|  | R3 | AAAAACTTAAACCG |  | 103 |
|  | Probe3 | TTTTTTCGGTATGTGGACGATAAGG |  | 104 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 111 | F3-14 | ATCGATTTTGACGA | 78 | 117 |
| | R3 | AAAAACTTAAACCG | | 103 |
| | Probe3 | TTTTTTCGGTATGTGGACGATAAGG | | 104 |
| 112 | F3-15 | TCGATTTTGACGAA | 77 | 118 |
| | R3 | AAAAACTTAAACCG | | 103 |
| | Probe3 | TTTTTTCGGTATGTGGACGATAAGG | | 104 |
| 113 | F3-16 | CGATTTTGACGAAG | 76 | 119 |
| | R3 | AAAAACTTAAACCG | | 103 |
| | Probe3 | TTTTTTCGGTATGTGGACGATAAGG | | 104 |
| 114 | F3-17 | GATTTTGACGAAGG | 75 | 120 |
| | R3 | AAAAACTTAAACCG | | 103 |
| | Probe3 | TTTTTTCGGTATGTGGACGATAAGG | | 104 |
| 115 | F3-18 | CGATTTTGACGAAGGAGTTAATGC | 76 | 121 |
| | R3 | AAAAACTTAAACCG | | 103 |
| | Probe3 | TTTTTTCGGTATGTGGACGATAAGG | | 104 |
| 116 | F3-19 | GATTTTGACGAAGGAGTTAATGC | 75 | 122 |
| | R3 | AAAAACTTAAACCG | | 103 |
| | Probe3 | TTTTTTCGGTATGTGGACGATAAGG | | 104 |
| 117 | F4-1 | CGGAAGTGAGGTATTTTTTC | 138 | 123 |
| | R4 | ATTACAATCTAATT | | 124 |
| | Probe4 | ATTACGAGGAGTTAGGATTTTATTA | | 125 |
| 118 | F4-2 | GGAAGTGAGGTATTTTTTC | 137 | 126 |
| | R4 | ATTACAATCTAATT | | 124 |
| | Probe4 | ATTACGAGGAGTTAGGATTTTATTA | | 125 |
| 119 | F4-3 | TTCGGTATGTGGAC | 120 | 127 |
| | R4 | ATTACAATCTAATT | | 124 |
| | Probe4 | ATTACGAGGAGTTAGGATTTTATTA | | 125 |
| 120 | F4-4 | TCGGTATGTGGACG | 119 | 128 |
| | R4 | ATTACAATCTAATT | | 124 |
| | Probe4 | ATTACGAGGAGTTAGGATTTTATTA | | 125 |
| 121 | F4-5 | CGGTATGTGGACGA | 118 | 129 |
| | R4 | ATTACAATCTAATT | | 124 |
| | Probe4 | ATTACGAGGAGTTAGGATTTTATTA | | 125 |
| 122 | F4-6 | GGTATGTGGACGAT | 117 | 130 |
| | R4 | ATTACAATCTAATT | | 124 |
| | Probe4 | ATTACGAGGAGTTAGGATTTTATTA | | 125 |
| 123 | F4-7 | GTGGACGATAAGGC | 112 | 131 |
| | R4 | ATTACAATCTAATT | | 124 |
| | Probe4 | ATTACGAGGAGTTAGGATTTTATTA | | 125 |
| 124 | F4-8 | TGGACGATAAGGCG | 111 | 132 |
| | R4 | ATTACAATCTAATT | | 124 |
| | Probe4 | ATTACGAGGAGTTAGGATTTTATTA | | 125 |
| 125 | F4-9 | GGACGATAAGGCGG | 110 | 133 |
| | R4 | ATTACAATCTAATT | | 124 |
| | Probe4 | ATTACGAGGAGTTAGGATTTTATTA | | 125 |
| 126 | F4-10 | GACGATAAGGCGGT | 109 | 134 |
| | R4 | ATTACAATCTAATT | | 124 |
| | Probe4 | ATTACGAGGAGTTAGGATTTTATTA | | 125 |
| 127 | F4-11 | ACGATAAGGCGGTT | 108 | 135 |
| | R4 | ATTACAATCTAATT | | 124 |
| | Probe4 | ATTACGAGGAGTTAGGATTTTATTA | | 125 |
| 128 | F4-12 | CGATAAGGCGGTTT | 107 | 136 |
| | R4 | ATTACAATCTAATT | | 124 |
| | Probe4 | ATTACGAGGAGTTAGGATTTTATTA | | 125 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 129 | F4-13 | GATAAGGCGGTTTA | 106 | 137 |
|  | R4 | ATTACAATCTAATT |  | 124 |
|  | Probe4 | ATTACGAGGAGTTAGGATTTTATTA |  | 125 |
| 130 | F5-1 | TTAGGGATAATATT | 140 | 138 |
|  | R5 | CATTATCGTTCACG |  | 139 |
|  | Probe5 | CGCGAGTTAAAGTTTTGATTATTGT |  | 140 |
| 131 | F5-2 | TAGGGATAATATTA | 139 | 141 |
|  | R5 | CATTATCGTTCACG |  | 139 |
|  | Probe5 | CGCGAGTTAAAGTTTTGATTATTGT |  | 140 |
| 132 | F5-3 | AGGGATAATATTAA | 138 | 142 |
|  | R5 | CATTATCGTTCACG |  | 139 |
|  | Probe5 | CGCGAGTTAAAGTTTTGATTATTGT |  | 140 |
| 133 | F5-4 | GGGATAATATTAAT | 137 | 143 |
|  | R5 | CATTATCGTTCACG |  | 139 |
|  | Probe5 | CGCGAGTTAAAGTTTTGATTATTGT |  | 140 |
| 134 | F5-5 | GGATAATATTAATA | 136 | 144 |
|  | R5 | CATTATCGTTCACG |  | 139 |
|  | Probe5 | CGCGAGTTAAAGTTTTGATTATTGT |  | 140 |
| 135 | F5-6 | GATAATATTAATAA | 135 | 145 |
|  | R5 | CATTATCGTTCACG |  | 139 |
|  | Probe5 | CGCGAGTTAAAGTTTTGATTATTGT |  | 140 |
| 136 | F5-7 | ATAATATTAATAAT | 134 | 146 |
|  | R5 | CATTATCGTTCACG |  | 139 |
|  | Probe5 | CGCGAGTTAAAGTTTTGATTATTGT |  | 140 |
| 137 | F5-8 | TAATATTAATAATA | 133 | 147 |
|  | R5 | CATTATCGTTCACG |  | 139 |
|  | Probe5 | CGCGAGTTAAAGTTTTGATTATTGT |  | 140 |
| 138 | F5-9 | AATATTAATAATAG | 132 | 148 |
|  | R5 | CATTATCGTTCACG |  | 139 |
|  | Probe5 | CGCGAGTTAAAGTTTTGATTATTGT |  | 140 |
| 139 | F5-10 | ATATTAATAATAGG | 131 | 149 |
|  | R5 | CATTATCGTTCACG |  | 139 |
|  | Probe5 | CGCGAGTTAAAGTTTTGATTATTGT |  | 140 |
| 140 | F5-11 | TATTAATAATAGGG | 130 | 150 |
|  | R5 | CATTATCGTTCACG |  | 139 |
|  | Probe5 | CGCGAGTTAAAGTTTTGATTATTGT |  | 140 |
| 141 | F5-12 | ATTAATAATAGGGG | 129 | 151 |
|  | R5 | CATTATCGTTCACG |  | 139 |
|  | Probe5 | CGCGAGTTAAAGTTTTGATTATTGT |  | 140 |
| 142 | F5-13 | TTAATAATAGGGGA | 128 | 152 |
|  | R5 | CATTATCGTTCACG |  | 139 |
|  | Probe5 | CGCGAGTTAAAGTTTTGATTATTGT |  | 140 |
| 143 | F5-14 | TAATAATAGGGGAG | 127 | 153 |
|  | R5 | CATTATCGTTCACG |  | 139 |
|  | Probe5 | CGCGAGTTAAAGTTTTGATTATTGT |  | 140 |
| 144 | F5-15 | AATAATAGGGGAGT | 126 | 154 |
|  | R5 | CATTATCGTTCACG |  | 139 |
|  | Probe5 | CGCGAGTTAAAGTTTTGATTATTGT |  | 140 |
| 145 | F5-16 | ATAATAGGGGAGTT | 125 | 155 |
|  | R5 | CATTATCGTTCACG |  | 139 |
|  | Probe5 | CGCGAGTTAAAGTTTTGATTATTGT |  | 140 |
| 146 | F5-17 | TAATAGGGGAGTTG | 124 | 156 |
|  | R5 | CATTATCGTTCACG |  | 139 |
|  | Probe5 | CGCGAGTTAAAGTTTTGATTATTGT |  | 140 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 147 | F5-18 | AATAGGGGAGTTGG | 123 | 157 |
|  | R5 | CATTATCGTTCACG |  | 139 |
|  | Probe5 | CGCGAGTTAAAGTTTTGATTATTGT |  | 140 |
| 148 | F5-19 | ATAGGGGAGTTGGA | 122 | 158 |
|  | R5 | CATTATCGTTCACG |  | 139 |
|  | Probe5 | CGCGAGTTAAAGTTTTGATTATTGT |  | 140 |
| 149 | F5-20 | TAGGGGAGTTGGAT | 121 | 159 |
|  | R5 | CATTATCGTTCACG |  | 139 |
|  | Probe5 | CGCGAGTTAAAGTTTTGATTATTGT |  | 140 |
| 150 | F5-21 | AGGGGAGTTGGATT | 120 | 160 |
|  | R5 | CATTATCGTTCACG |  | 139 |
|  | Probe5 | CGCGAGTTAAAGTTTTGATTATTGT |  | 140 |
| 151 | F5-22 | GGGGAGTTGGATTA | 119 | 161 |
|  | R5 | CATTATCGTTCACG |  | 139 |
|  | Probe5 | CGCGAGTTAAAGTTTTGATTATTGT |  | 140 |
| 152 | F5-23 | GGGAGTTGGATTAC | 118 | 162 |
|  | R5 | CATTATCGTTCACG |  | 139 |
|  | Probe5 | CGCGAGTTAAAGTTTTGATTATTGT |  | 140 |
| 153 | F5-24 | GGAGTTGGATTACG | 117 | 163 |
|  | R5 | CATTATCGTTCACG |  | 139 |
|  | Probe5 | CGCGAGTTAAAGTTTTGATTATTGT |  | 140 |
| 154 | F5-25 | GAGTTGGATTACGA | 116 | 164 |
|  | R5 | CATTATCGTTCACG |  | 139 |
|  | Probe5 | CGCGAGTTAAAGTTTTGATTATTGT |  | 140 |
| 155 | F5-26 | AGTTGGATTACGAG | 115 | 165 |
|  | R5 | CATTATCGTTCACG |  | 139 |
|  | Probe5 | CGCGAGTTAAAGTTTTGATTATTGT |  | 140 |
| 156 | F5-27 | GTTGGATTACGAGG | 114 | 166 |
|  | R5 | CATTATCGTTCACG |  | 139 |
|  | Probe5 | CGCGAGTTAAAGTTTTGATTATTGT |  | 140 |
| 157 | F5-28 | TTGGATTACGAGGA | 113 | 167 |
|  | R5 | CATTATCGTTCACG |  | 139 |
|  | Probe5 | CGCGAGTTAAAGTTTTGATTATTGT |  | 140 |
| 158 | F5-29 | TGGATTACGAGGAG | 112 | 168 |
|  | R5 | CATTATCGTTCACG |  | 139 |
|  | Probe5 | CGCGAGTTAAAGTTTTGATTATTGT |  | 140 |
| 159 | F5-30 | GGATTACGAGGAGT | 111 | 169 |
|  | R5 | CATTATCGTTCACG |  | 139 |
|  | Probe5 | CGCGAGTTAAAGTTTTGATTATTGT |  | 140 |
| 160 | F5-31 | GATTACGAGGAGTT | 110 | 170 |
|  | R5 | CATTATCGTTCACG |  | 139 |
|  | Probe5 | CGCGAGTTAAAGTTTTGATTATTGT |  | 140 |
| 161 | F5-32 | ATTACGAGGAGTTA | 109 | 171 |
|  | R5 | CATTATCGTTCACG |  | 139 |
|  | Probe5 | CGCGAGTTAAAGTTTTGATTATTGT |  | 140 |
| 162 | F5-33 | TTACGAGGAGTTAG | 108 | 172 |
|  | R5 | CATTATCGTTCACG |  | 139 |
|  | Probe5 | CGCGAGTTAAAGTTTTGATTATTGT |  | 140 |
| 163 | F5-34 | TACGAGGAGTTAGG | 107 | 173 |
|  | R5 | CATTATCGTTCACG |  | 139 |
|  | Probe5 | CGCGAGTTAAAGTTTTGATTATTGT |  | 140 |
| 164 | F5-35 | ACGAGGAGTTAGGA | 106 | 174 |
|  | R5 | CATTATCGTTCACG |  | 139 |
|  | Probe5 | CGCGAGTTAAAGTTTTGATTATTGT |  | 140 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 165 | F5-36 | CGAGGAGTTAGGAT | 105 | 175 |
|  | R5 | CATTATCGTTCACG |  | 139 |
|  | Probe5 | CGCGAGTTAAAGTTTTGATTATTGT |  | 140 |
| 166 | F5-37 | GAGGAGTTAGGATT | 104 | 176 |
|  | R5 | CATTATCGTTCACG |  | 139 |
|  | Probe5 | CGCGAGTTAAAGTTTTGATTATTGT |  | 140 |
| 167 | F5-38 | AGGAGTTAGGATTT | 103 | 177 |
|  | R5 | CATTATCGTTCACG |  | 139 |
|  | Probe5 | CGCGAGTTAAAGTTTTGATTATTGT |  | 140 |
| 168 | F5-39 | GGAGTTAGGATTTT | 102 | 178 |
|  | R5 | CATTATCGTTCACG |  | 139 |
|  | Probe5 | CGCGAGTTAAAGTTTTGATTATTGT |  | 140 |
| 169 | F5-40 | GAGTTAGGATTTTA | 101 | 179 |
|  | R5 | CATTATCGTTCACG |  | 139 |
|  | Probe5 | CGCGAGTTAAAGTTTTGATTATTGT |  | 140 |
| 170 | F5-41 | AGTTAGGATTTTAT | 100 | 180 |
|  | R5 | CATTATCGTTCACG |  | 139 |
|  | Probe5 | CGCGAGTTAAAGTTTTGATTATTGT |  | 140 |
| 171 | F5-42 | GTTAGGATTTTATT | 99 | 181 |
|  | R5 | CATTATCGTTCACG |  | 139 |
|  | Probe5 | CGCGAGTTAAAGTTTTGATTATTGT |  | 140 |
| 172 | F5-43 | TTAGGATTTTATTA | 98 | 182 |
|  | R5 | CATTATCGTTCACG |  | 139 |
|  | Probe5 | CGCGAGTTAAAGTTTTGATTATTGT |  | 140 |
| 173 | F5-44 | TAGGATTTTATTAG | 97 | 183 |
|  | R5 | CATTATCGTTCACG |  | 139 |
|  | Probe5 | CGCGAGTTAAAGTTTTGATTATTGT |  | 140 |
| 174 | F5-45 | AGGATTTTATTAGA | 96 | 184 |
|  | R5 | CATTATCGTTCACG |  | 139 |
|  | Probe5 | CGCGAGTTAAAGTTTTGATTATTGT |  | 140 |
| 175 | F5-46 | GGATTTTATTAGAT | 95 | 185 |
|  | R5 | CATTATCGTTCACG |  | 139 |
|  | Probe5 | CGCGAGTTAAAGTTTTGATTATTGT |  | 140 |
| 176 | F5-47 | GATTTTATTAGATG | 94 | 186 |
|  | R5 | CATTATCGTTCACG |  | 139 |
|  | Probe5 | CGCGAGTTAAAGTTTTGATTATTGT |  | 140 |
| 177 | F5-48 | ATTTTATTAGATGG | 93 | 187 |
|  | R5 | CATTATCGTTCACG |  | 139 |
|  | Probe5 | CGCGAGTTAAAGTTTTGATTATTGT |  | 140 |
| 178 | F5-49 | TTTTATTAGATGGA | 92 | 188 |
|  | R5 | CATTATCGTTCACG |  | 139 |
|  | Probe5 | CGCGAGTTAAAGTTTTGATTATTGT |  | 140 |
| 179 | F5-50 | TTTATTAGATGGAA | 91 | 189 |
|  | R5 | CATTATCGTTCACG |  | 139 |
|  | Probe5 | CGCGAGTTAAAGTTTTGATTATTGT |  | 140 |
| 180 | F5-51 | TTATTAGATGGAAG | 90 | 190 |
|  | R5 | CATTATCGTTCACG |  | 139 |
|  | Probe5 | CGCGAGTTAAAGTTTTGATTATTGT |  | 140 |
| 181 | F5-52 | TATTAGATGGAAGT | 89 | 191 |
|  | R5 | CATTATCGTTCACG |  | 139 |
|  | Probe5 | CGCGAGTTAAAGTTTTGATTATTGT |  | 140 |
| 182 | F5-53 | ATTAGATGGAAGTG | 88 | 192 |
|  | R5 | CATTATCGTTCACG |  | 139 |
|  | Probe5 | CGCGAGTTAAAGTTTTGATTATTGT |  | 140 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 183 | F5-54 | TTAGATGGAAGTGT | 87 | 193 |
| | R5 | CATTATCGTTCACG | | 139 |
| | Probe5 | CGCGAGTTAAAGTTTTGATTATTGT | | 140 |
| 184 | F5-55 | TAGATGGAAGTGTA | 86 | 194 |
| | R5 | CATTATCGTTCACG | | 139 |
| | Probe5 | CGCGAGTTAAAGTTTTGATTATTGT | | 140 |
| 185 | F5-56 | AGATGGAAGTGTAA | 85 | 195 |
| | R5 | CATTATCGTTCACG | | 139 |
| | Probe5 | CGCGAGTTAAAGTTTTGATTATTGT | | 140 |
| 186 | F5-57 | GATGGAAGTGTAAG | 84 | 196 |
| | R5 | CATTATCGTTCACG | | 139 |
| | Probe5 | CGCGAGTTAAAGTTTTGATTATTGT | | 140 |
| 187 | F6-14 | AGGATATTTTGCGC | 127 | 197 |
| | R6 | AACAATTAATATCC | | 198 |
| | Probe6 | AGAAGTGGTTTTTATTTTTTCGT | | 199 |
| 188 | F6-15 | GGATATTTTGCGCG | 126 | 200 |
| | R6 | AACAATTAATATCC | | 198 |
| | Probe6 | AGAAGTGGTTTTTATTTTTTCGT | | 199 |
| 189 | F6-16 | GATATTTTGCGCGA | 125 | 201 |
| | R6 | AACAATTAATATCC | | 198 |
| | Probe6 | AGAAGTGGTTTTTATTTTTTCGT | | 199 |
| 190 | F6-17 | ATATTTTGCGCGAG | 124 | 202 |
| | R6 | AACAATTAATATCC | | 198 |
| | Probe6 | AGAAGTGGTTTTTATTTTTTCGT | | 199 |
| 191 | F6-18 | TATTTTGCGCGAGT | 123 | 203 |
| | R6 | AACAATTAATATCC | | 198 |
| | Probe6 | AGAAGTGGTTTTTATTTTTTCGT | | 199 |
| 192 | F6-19 | ATTTTGCGCGAGTT | 122 | 204 |
| | R6 | AACAATTAATATCC | | 198 |
| | Probe6 | AGAAGTGGTTTTTATTTTTTCGT | | 199 |
| 193 | F6-20 | TTTTGCGCGAGTTA | 121 | 205 |
| | R6 | AACAATTAATATCC | | 198 |
| | Probe6 | AGAAGTGGTTTTTATTTTTTCGT | | 199 |
| 194 | F6-21 | TTTGCGCGAGTTAA | 120 | 206 |
| | R6 | AACAATTAATATCC | | 198 |
| | Probe6 | AGAAGTGGTTTTTATTTTTTCGT | | 199 |
| 195 | F6-22 | TTGCGCGAGTTAAA | 119 | 207 |
| | R6 | AACAATTAATATCC | | 198 |
| | Probe6 | AGAAGTGGTTTTTATTTTTTCGT | | 199 |
| 196 | F6-23 | TGCGCGAGTTAAAG | 118 | 208 |
| | R6 | AACAATTAATATCC | | 198 |
| | Probe6 | AGAAGTGGTTTTTATTTTTTCGT | | 199 |
| 197 | F6-24 | GCGCGAGTTAAAGT | 117 | 209 |
| | R6 | AACAATTAATATCC | | 198 |
| | Probe6 | AGAAGTGGTTTTTATTTTTTCGT | | 199 |
| 198 | F6-25 | CGCGAGTTAAAGTT | 116 | 210 |
| | R6 | AACAATTAATATCC | | 198 |
| | Probe6 | AGAAGTGGTTTTTATTTTTTCGT | | 199 |
| 199 | F6-26 | GCGAGTTAAAGTTT | 115 | 211 |
| | R6 | AACAATTAATATCC | | 198 |
| | Probe6 | AGAAGTGGTTTTTATTTTTTCGT | | 199 |
| 200 | F6-49 | TTTTGGACGTGAAC | 92 | 212 |
| | R6 | AACAATTAATATCC | | 198 |
| | Probe6 | AGAAGTGGTTTTTATTTTTTCGT | | 199 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 201 | F6-50 | TTTGGACGTGAACG | 91 | 213 |
| | R6 | AACAATTAATATCC | | 198 |
| | Probe6 | AGAAGTGGTTTTATTTTTTTCGT | | 199 |
| 202 | F6-51 | TTGGACGTGAACGA | 90 | 214 |
| | R6 | AACAATTAATATCC | | 198 |
| | Probe6 | AGAAGTGGTTTTATTTTTTTCGT | | 199 |
| 203 | F6-52 | TGGACGTGAACGAT | 89 | 215 |
| | R6 | AACAATTAATATCC | | 198 |
| | Probe6 | AGAAGTGGTTTTATTTTTTTCGT | | 199 |
| 204 | F6-53 | GGACGTGAACGATA | 88 | 216 |
| | R6 | AACAATTAATATCC | | 198 |
| | Probe6 | AGAAGTGGTTTTATTTTTTTCGT | | 199 |
| 205 | F6-54 | GACGTGAACGATAA | 87 | 217 |
| | R6 | AACAATTAATATCC | | 198 |
| | Probe6 | AGAAGTGGTTTTATTTTTTTCGT | | 199 |
| 206 | F6-55 | ACGTGAACGATAAT | 86 | 218 |
| | R6 | AACAATTAATATCC | | 198 |
| | Probe6 | AGAAGTGGTTTTATTTTTTTCGT | | 199 |
| 207 | F6-56 | CGTGAACGATAATG | 85 | 219 |
| | R6 | AACAATTAATATCC | | 198 |
| | Probe6 | AGAAGTGGTTTTATTTTTTTCGT | | 199 |
| 208 | F6-57 | GTGAACGATAATGT | 84 | 220 |
| | R6 | AACAATTAATATCC | | 198 |
| | Probe6 | AGAAGTGGTTTTATTTTTTTCGT | | 199 |
| 209 | F7-1 | TTTTTCGTTAGTTC | 100 | 221 |
| | R7 | AAATCACCTATCCG | | 222 |
| | Probe7 | TAAATGATTAAGATTTTGAGGAAAA | | 223 |
| 210 | F7-2 | TTTTCGTTAGTTCG | 99 | 224 |
| | R7 | AAATCACCTATCCG | | 222 |
| | Probe7 | TAAATGATTAAGATTTTGAGGAAAA | | 223 |
| 211 | F7-3 | TTTCGTTAGTTCGG | 98 | 225 |
| | R7 | AAATCACCTATCCG | | 222 |
| | Probe7 | TAAATGATTAAGATTTTGAGGAAAA | | 223 |
| 212 | F7-4 | TTCGTTAGTTCGGT | 97 | 226 |
| | R7 | AAATCACCTATCCG | | 222 |
| | Probe7 | TAAATGATTAAGATTTTGAGGAAAA | | 223 |
| 213 | F7-5 | TCGTTAGTTCGGTT | 96 | 227 |
| | R7 | AAATCACCTATCCG | | 222 |
| | Probe7 | TAAATGATTAAGATTTTGAGGAAAA | | 223 |
| 214 | F7-6 | CGTTAGTTCGGTTT | 95 | 228 |
| | R7 | AAATCACCTATCCG | | 222 |
| | Probe7 | TAAATGATTAAGATTTTGAGGAAAA | | 223 |
| 215 | F7-7 | GTTAGTTCGGTTTT | 94 | 229 |
| | R7 | AAATCACCTATCCG | | 222 |
| | Probe7 | TAAATGATTAAGATTTTGAGGAAAA | | 223 |
| 216 | F7-8 | TTAGTTCGGTTTTC | 93 | 230 |
| | R7 | AAATCACCTATCCG | | 222 |
| | Probe7 | TAAATGATTAAGATTTTGAGGAAAA | | 223 |
| 217 | F7-9 | TAGTTCGGTTTTCG | 92 | 231 |
| | R7 | AAATCACCTATCCG | | 222 |
| | Probe7 | TAAATGATTAAGATTTTGAGGAAAA | | 223 |
| 218 | F7-10 | AGTTCGGTTTTCGA | 91 | 232 |
| | R7 | AAATCACCTATCCG | | 222 |
| | Probe7 | TAAATGATTAAGATTTTGAGGAAAA | | 223 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 219 | F7-11 | GTTCGGTTTTCGAAA | 90 | 233 |
|  | R7 | AAATCACCTATCCG |  | 222 |
|  | Probe7 | TAAATGATTAAGATTTTGAGGAAAA |  | 223 |
| 220 | F7-12 | TTCGGTTTTCGAAA | 89 | 234 |
|  | R7 | AAATCACCTATCCG |  | 222 |
|  | Probe7 | TAAATGATTAAGATTTTGAGGAAAA |  | 223 |
| 221 | F7-13 | TCGGTTTTCGAAAA | 88 | 235 |
|  | R7 | AAATCACCTATCCG |  | 222 |
|  | Probe7 | TAAATGATTAAGATTTTGAGGAAAA |  | 223 |
| 222 | F7-14 | CGGTTTTCGAAAAT | 87 | 236 |
|  | R7 | AAATCACCTATCCG |  | 222 |
|  | Probe7 | TAAATGATTAAGATTTTGAGGAAAA |  | 223 |
| 223 | F7-15 | GGTTTTCGAAAATT | 86 | 237 |
|  | R7 | AAATCACCTATCCG |  | 222 |
|  | Probe7 | TAAATGATTAAGATTTTGAGGAAAA |  | 223 |
| 224 | F8-1 | CGGTTTTTTTATTTTACG | 91 | 238 |
|  | R8 | TAAAAAAAAAATAA |  | 239 |
|  | Probe8 | AGAGTTACGAGTTTAGTTCGAATAT |  | 240 |
| 225 | F8-2 | GGTTTTTTTATTTTACG | 90 | 241 |
|  | R8 | TAAAAAAAAAATAA |  | 239 |
|  | Probe8 | AGAGTTACGAGTTTAGTTCGAATAT |  | 240 |
| 226 | F9-1 | TGGGATTCGGATAT | 140 | 242 |
|  | R9 | TCTTCGCGATCCAA |  | 243 |
|  | Probe9 | TTTCGAATTGGTGTTGAAACGCGTT |  | 244 |
| 227 | F9-2 | GGGATTCGGATATC | 139 | 245 |
|  | R9 | TCTTCGCGATCCAA |  | 243 |
|  | Probe9 | TTTCGAATTGGTGTTGAAACGCGTT |  | 244 |
| 228 | F9-3 | GGATTCGGATATCG | 138 | 246 |
|  | R9 | TCTTCGCGATCCAA |  | 243 |
|  | Probe9 | TTTCGAATTGGTGTTGAAACGCGTT |  | 244 |
| 229 | F9-4 | GATTCGGATATCGG | 137 | 247 |
|  | R9 | TCTTCGCGATCCAA |  | 243 |
|  | Probe9 | TTTCGAATTGGTGTTGAAACGCGTT |  | 244 |
| 230 | F9-5 | ATTCGGATATCGGG | 136 | 248 |
|  | R9 | TCTTCGCGATCCAA |  | 243 |
|  | Probe9 | TTTCGAATTGGTGTTGAAACGCGTT |  | 244 |
| 231 | F9-6 | TTCGGATATCGGGA | 135 | 249 |
|  | R9 | TCTTCGCGATCCAA |  | 243 |
|  | Probe9 | TTTCGAATTGGTGTTGAAACGCGTT |  | 244 |
| 232 | F9-7 | TCGGATATCGGGAA | 134 | 250 |
|  | R9 | TCTTCGCGATCCAA |  | 243 |
|  | Probe9 | TTTCGAATTGGTGTTGAAACGCGTT |  | 244 |
| 233 | F9-8 | CGGATATCGGGAAG | 133 | 251 |
|  | R9 | TCTTCGCGATCCAA |  | 243 |
|  | Probe9 | TTTCGAATTGGTGTTGAAACGCGTT |  | 244 |
| 234 | F9-9 | GGATATCGGGAAGA | 132 | 252 |
|  | R9 | TCTTCGCGATCCAA |  | 243 |
|  | Probe9 | TTTCGAATTGGTGTTGAAACGCGTT |  | 244 |
| 235 | F9-10 | GATATCGGGAAGAA | 131 | 253 |
|  | R9 | TCTTCGCGATCCAA |  | 243 |
|  | Probe9 | TTTCGAATTGGTGTTGAAACGCGTT |  | 244 |
| 236 | F9-11 | ATATCGGGAAGAAT | 130 | 254 |
|  | R9 | TCTTCGCGATCCAA |  | 243 |
|  | Probe9 | TTTCGAATTGGTGTTGAAACGCGTT |  | 244 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 237 | F9-12 | TATCGGGAAGAATT | 129 | 255 |
|  | R9 | TCTTCGCGATCCAA |  | 243 |
|  | Probe9 | TTTCGAATTGGTGTTGAAACGCGTT |  | 244 |
| 238 | F9-13 | ATCGGGAAGAATTT | 128 | 256 |
|  | R9 | TCTTCGCGATCCAA |  | 243 |
|  | Probe9 | TTTCGAATTGGTGTTGAAACGCGTT |  | 244 |
| 239 | F9-14 | TCGGGAAGAATTTT | 127 | 257 |
|  | R9 | TCTTCGCGATCCAA |  | 243 |
|  | Probe9 | TTTCGAATTGGTGTTGAAACGCGTT |  | 244 |
| 240 | F9-15 | CGGGAAGAATTTTT | 126 | 258 |
|  | R9 | TCTTCGCGATCCAA |  | 243 |
|  | Probe9 | TTTCGAATTGGTGTTGAAACGCGTT |  | 244 |
| 241 | F9-16 | GGGAAGAATTTTTT | 125 | 259 |
|  | R9 | TCTTCGCGATCCAA |  | 243 |
|  | Probe9 | TTTCGAATTGGTGTTGAAACGCGTT |  | 244 |
| 242 | F9-17 | GGAAGAATTTTTTG | 124 | 260 |
|  | R9 | TCTTCGCGATCCAA |  | 243 |
|  | Probe9 | TTTCGAATTGGTGTTGAAACGCGTT |  | 244 |
| 243 | F9-18 | GAAGAATTTTTTGT | 123 | 261 |
|  | R9 | TCTTCGCGATCCAA |  | 243 |
|  | Probe9 | TTTCGAATTGGTGTTGAAACGCGTT |  | 244 |
| 244 | F9-19 | AAGAATTTTTTGTA | 122 | 262 |
|  | R9 | TCTTCGCGATCCAA |  | 243 |
|  | Probe9 | TTTCGAATTGGTGTTGAAACGCGTT |  | 244 |
| 245 | F9-20 | AGAATTTTTTGTAG | 121 | 263 |
|  | R9 | TCTTCGCGATCCAA |  | 243 |
|  | Probe9 | TTTCGAATTGGTGTTGAAACGCGTT |  | 244 |
| 246 | F9-21 | GAATTTTTTGTAGA | 120 | 264 |
|  | R9 | TCTTCGCGATCCAA |  | 243 |
|  | Probe9 | TTTCGAATTGGTGTTGAAACGCGTT |  | 244 |
| 247 | F9-22 | AATTTTTTGTAGAG | 119 | 265 |
|  | R9 | TCTTCGCGATCCAA |  | 243 |
|  | Probe9 | TTTCGAATTGGTGTTGAAACGCGTT |  | 244 |
| 248 | F9-23 | ATTTTTTGTAGAGT | 118 | 266 |
|  | R9 | TCTTCGCGATCCAA |  | 243 |
|  | Probe9 | TTTCGAATTGGTGTTGAAACGCGTT |  | 244 |
| 249 | F9-24 | TTTTTTGTAGAGTT | 117 | 267 |
|  | R9 | TCTTCGCGATCCAA |  | 243 |
|  | Probe9 | TTTCGAATTGGTGTTGAAACGCGTT |  | 244 |
| 250 | F9-25 | TTTTTGTAGAGTTA | 116 | 268 |
|  | R9 | TCTTCGCGATCCAA |  | 243 |
|  | Probe9 | TTTCGAATTGGTGTTGAAACGCGTT |  | 244 |
| 251 | F9-26 | TTTTGTAGAGTTAC | 115 | 269 |
|  | R9 | TCTTCGCGATCCAA |  | 243 |
|  | Probe9 | TTTCGAATTGGTGTTGAAACGCGTT |  | 244 |
| 252 | F9-27 | TTTGTAGAGTTACG | 114 | 270 |
|  | R9 | TCTTCGCGATCCAA |  | 243 |
|  | Probe9 | TTTCGAATTGGTGTTGAAACGCGTT |  | 244 |
| 253 | F9-28 | TTGTAGAGTTACGA | 113 | 271 |
|  | R9 | TCTTCGCGATCCAA |  | 243 |
|  | Probe9 | TTTCGAATTGGTGTTGAAACGCGTT |  | 244 |
| 254 | F9-29 | TGTAGAGTTACGAG | 112 | 272 |
|  | R9 | TCTTCGCGATCCAA |  | 243 |
|  | Probe9 | TTTCGAATTGGTGTTGAAACGCGTT |  | 244 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 255 | F9-30 | GTAGAGTTACGAGT | 111 | 273 |
|  | R9 | TCTTCGCGATCCAA |  | 243 |
|  | Probe9 | TTTCGAATTGGTGTTGAAACGCGTT |  | 244 |
| 256 | F9-31 | TAGAGTTACGAGTT | 110 | 274 |
|  | R9 | TCTTCGCGATCCAA |  | 243 |
|  | Probe9 | TTTCGAATTGGTGTTGAAACGCGTT |  | 244 |
| 257 | F9-32 | AGAGTTACGAGTTT | 109 | 275 |
|  | R9 | TCTTCGCGATCCAA |  | 243 |
|  | Probe9 | TTTCGAATTGGTGTTGAAACGCGTT |  | 244 |
| 258 | F9-33 | GAGTTACGAGTTTA | 108 | 276 |
|  | R9 | TCTTCGCGATCCAA |  | 243 |
|  | Probe9 | TTTCGAATTGGTGTTGAAACGCGTT |  | 244 |
| 259 | F9-34 | AGTTACGAGTTTAG | 107 | 277 |
|  | R9 | TCTTCGCGATCCAA |  | 243 |
|  | Probe9 | TTTCGAATTGGTGTTGAAACGCGTT |  | 244 |
| 260 | F9-35 | GTTACGAGTTTAGT | 106 | 278 |
|  | R9 | TCTTCGCGATCCAA |  | 243 |
|  | Probe9 | TTTCGAATTGGTGTTGAAACGCGTT |  | 244 |
| 261 | F9-36 | TTACGAGTTTAGTT | 105 | 279 |
|  | R9 | TCTTCGCGATCCAA |  | 243 |
|  | Probe9 | TTTCGAATTGGTGTTGAAACGCGTT |  | 244 |
| 262 | F9-37 | TACGAGTTTAGTTC | 104 | 280 |
|  | R9 | TCTTCGCGATCCAA |  | 243 |
|  | Probe9 | TTTCGAATTGGTGTTGAAACGCGTT |  | 244 |
| 263 | F9-38 | ACGAGTTTAGTTCG | 103 | 281 |
|  | R9 | TCTTCGCGATCCAA |  | 243 |
|  | Probe9 | TTTCGAATTGGTGTTGAAACGCGTT |  | 244 |
| 264 | F9-39 | CGAGTTTAGTTCGA | 102 | 282 |
|  | R9 | TCTTCGCGATCCAA |  | 243 |
|  | Probe9 | TTTCGAATTGGTGTTGAAACGCGTT |  | 244 |
| 265 | F9-40 | GAGTTTAGTTCGAA | 101 | 283 |
|  | R9 | TCTTCGCGATCCAA |  | 243 |
|  | Probe9 | TTTCGAATTGGTGTTGAAACGCGTT |  | 244 |
| 266 | F9-41 | AGTTTAGTTCGAAT | 100 | 284 |
|  | R9 | TCTTCGCGATCCAA |  | 243 |
|  | Probe9 | TTTCGAATTGGTGTTGAAACGCGTT |  | 244 |
| 267 | F9-42 | GTTTAGTTCGAATA | 99 | 285 |
|  | R9 | TCTTCGCGATCCAA |  | 243 |
|  | Probe9 | TTTCGAATTGGTGTTGAAACGCGTT |  | 244 |
| 268 | F9-43 | TTTAGTTCGAATAT | 98 | 286 |
|  | R9 | TCTTCGCGATCCAA |  | 243 |
|  | Probe9 | TTTCGAATTGGTGTTGAAACGCGTT |  | 244 |
| 269 | F9-44 | TTAGTTCGAATATT | 97 | 287 |
|  | R9 | TCTTCGCGATCCAA |  | 243 |
|  | Probe9 | TTTCGAATTGGTGTTGAAACGCGTT |  | 244 |
| 270 | F9-45 | TAGTTCGAATATTT | 96 | 288 |
|  | R9 | TCTTCGCGATCCAA |  | 243 |
|  | Probe9 | TTTCGAATTGGTGTTGAAACGCGTT |  | 244 |
| 271 | F9-46 | AGTTCGAATATTTA | 95 | 289 |
|  | R9 | TCTTCGCGATCCAA |  | 243 |
|  | Probe9 | TTTCGAATTGGTGTTGAAACGCGTT |  | 244 |
| 272 | F9-47 | GTTCGAATATTTAT | 94 | 290 |
|  | R9 | TCTTCGCGATCCAA |  | 243 |
|  | Probe9 | TTTCGAATTGGTGTTGAAACGCGTT |  | 244 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 273 | F9-48 | TTCGAATATTTATT | 93 | 291 |
| | R9 | TCTTCGCGATCCAA | | 243 |
| | Probe9 | TTTCGAATTGGTGTTGAAACGCGTT | | 244 |
| 274 | F9-49 | TCGAATATTTATTT | 92 | 292 |
| | R9 | TCTTCGCGATCCAA | | 243 |
| | Probe9 | TTTCGAATTGGTGTTGAAACGCGTT | | 244 |
| 275 | F9-50 | CGAATATTTATTTT | 91 | 293 |
| | R9 | TCTTCGCGATCCAA | | 243 |
| | Probe9 | TTTCGAATTGGTGTTGAAACGCGTT | | 244 |
| 276 | F9-51 | GAATATTTATTTTT | 90 | 294 |
| | R9 | TCTTCGCGATCCAA | | 243 |
| | Probe9 | TTTCGAATTGGTGTTGAAACGCGTT | | 244 |
| 277 | F9-52 | AATATTTATTTTTT | 89 | 295 |
| | R9 | TCTTCGCGATCCAA | | 243 |
| | Probe9 | TTTCGAATTGGTGTTGAAACGCGTT | | 244 |
| 278 | F9-53 | ATATTTATTTTTTT | 88 | 296 |
| | R9 | TCTTCGCGATCCAA | | 243 |
| | Probe9 | TTTCGAATTGGTGTTGAAACGCGTT | | 244 |
| 279 | F9-54 | TATTTATTTTTTTT | 87 | 297 |
| | R9 | TCTTCGCGATCCAA | | 243 |
| | Probe9 | TTTCGAATTGGTGTTGAAACGCGTT | | 244 |
| 280 | F9-55 | ATTTATTTTTTTTT | 86 | 298 |
| | R9 | TCTTCGCGATCCAA | | 243 |
| | Probe9 | TTTCGAATTGGTGTTGAAACGCGTT | | 244 |
| 281 | F9-56 | TTTATTTTTTTTTT | 85 | 299 |
| | R9 | TCTTCGCGATCCAA | | 243 |
| | Probe9 | TTTCGAATTGGTGTTGAAACGCGTT | | 244 |
| 282 | F9-57 | TTATTTTTTTTTTA | 84 | 300 |
| | R9 | TCTTCGCGATCCAA | | 243 |
| | Probe9 | TTTCGAATTGGTGTTGAAACGCGTT | | 244 |
| 283 | F10-1 | TCGTGTAAAATGGA | 140 | 301 |
| | R10 | ACGCGCGATACCTA | | 302 |
| | Probe10 | TTCGACGGGGGCGATTCGGTGCGTA | | 303 |
| 284 | F10-2 | CGTGTAAAATGGAG | 139 | 304 |
| | R10 | ACGCGCGATACCTA | | 302 |
| | Probe10 | TTCGACGGGGGCGATTCGGTGCGTA | | 303 |
| 285 | F10-3 | GTGTAAAATGGAGT | 138 | 305 |
| | R10 | ACGCGCGATACCTA | | 302 |
| | Probe10 | TTCGACGGGGGCGATTCGGTGCGTA | | 303 |
| 286 | F10-4 | TGTAAAATGGAGTC | 137 | 306 |
| | R10 | ACGCGCGATACCTA | | 302 |
| | Probe10 | TTCGACGGGGGCGATTCGGTGCGTA | | 303 |
| 287 | F10-5 | GTAAAATGGAGTCG | 136 | 307 |
| | R10 | ACGCGCGATACCTA | | 302 |
| | Probe10 | TTCGACGGGGGCGATTCGGTGCGTA | | 303 |
| 288 | F10-6 | TAAAATGGAGTCGA | 135 | 308 |
| | R10 | ACGCGCGATACCTA | | 302 |
| | Probe10 | TTCGACGGGGGCGATTCGGTGCGTA | | 303 |
| 289 | F10-7 | AAAATGGAGTCGAC | 134 | 309 |
| | R10 | ACGCGCGATACCTA | | 302 |
| | Probe10 | TTCGACGGGGGCGATTCGGTGCGTA | | 303 |
| 290 | F10-8 | AAATGGAGTCGACG | 133 | 310 |
| | R10 | ACGCGCGATACCTA | | 302 |
| | Probe10 | TTCGACGGGGGCGATTCGGTGCGTA | | 303 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 291 | F10-9 | AATGGAGTCGACGG | 132 | 311 |
|  | R10 | ACGCGCGATACCTA |  | 302 |
|  | Probe10 | TTCGACGGGGGCGATTCGGTGCGTA |  | 303 |
| 292 | F10-10 | ATGGAGTCGACGGT | 131 | 312 |
|  | R10 | ACGCGCGATACCTA |  | 302 |
|  | Probe10 | TTCGACGGGGGCGATTCGGTGCGTA |  | 303 |
| 293 | F10-11 | TGGAGTCGACGGTA | 130 | 313 |
|  | R10 | ACGCGCGATACCTA |  | 302 |
|  | Probe10 | TTCGACGGGGGCGATTCGGTGCGTA |  | 303 |
| 294 | F10-12 | GGAGTCGACGGTAG | 129 | 314 |
|  | R10 | ACGCGCGATACCTA |  | 302 |
|  | Probe10 | TTCGACGGGGGCGATTCGGTGCGTA |  | 303 |
| 295 | F10-13 | GAGTCGACGGTAGT | 128 | 315 |
|  | R10 | ACGCGCGATACCTA |  | 302 |
|  | Probe10 | TTCGACGGGGGCGATTCGGTGCGTA |  | 303 |
| 296 | F10-14 | AGTCGACGGTAGTA | 127 | 316 |
|  | R10 | ACGCGCGATACCTA |  | 302 |
|  | Probe10 | TTCGACGGGGGCGATTCGGTGCGTA |  | 303 |
| 297 | F10-15 | GTCGACGGTAGTAA | 126 | 317 |
|  | R10 | ACGCGCGATACCTA |  | 302 |
|  | Probe10 | TTCGACGGGGGCGATTCGGTGCGTA |  | 303 |
| 298 | F10-16 | TCGACGGTAGTAAG | 125 | 318 |
|  | R10 | ACGCGCGATACCTA |  | 302 |
|  | Probe10 | TTCGACGGGGGCGATTCGGTGCGTA |  | 303 |
| 299 | F10-17 | CGACGGTAGTAAGT | 124 | 319 |
|  | R10 | ACGCGCGATACCTA |  | 302 |
|  | Probe10 | TTCGACGGGGGCGATTCGGTGCGTA |  | 303 |
| 300 | F10-18 | GACGGTAGTAAGTA | 123 | 320 |
|  | R10 | ACGCGCGATACCTA |  | 302 |
|  | Probe10 | TTCGACGGGGGCGATTCGGTGCGTA |  | 303 |
| 301 | F10-19 | ACGGTAGTAAGTAT | 122 | 321 |
|  | R10 | ACGCGCGATACCTA |  | 302 |
|  | Probe10 | TTCGACGGGGGCGATTCGGTGCGTA |  | 303 |
| 302 | F10-20 | CGGTAGTAAGTATT | 121 | 322 |
|  | R10 | ACGCGCGATACCTA |  | 302 |
|  | Probe10 | TTCGACGGGGGCGATTCGGTGCGTA |  | 303 |
| 303 | F10-21 | GGTAGTAAGTATTT | 120 | 323 |
|  | R10 | ACGCGCGATACCTA |  | 302 |
|  | Probe10 | TTCGACGGGGGCGATTCGGTGCGTA |  | 303 |
| 304 | F10-22 | GTAGTAAGTATTTC | 119 | 324 |
|  | R10 | ACGCGCGATACCTA |  | 302 |
|  | Probe10 | TTCGACGGGGGCGATTCGGTGCGTA |  | 303 |
| 305 | F10-23 | TAGTAAGTATTTCG | 118 | 325 |
|  | R10 | ACGCGCGATACCTA |  | 302 |
|  | Probe10 | TTCGACGGGGGCGATTCGGTGCGTA |  | 303 |
| 306 | F10-24 | AGTAAGTATTTCGA | 117 | 326 |
|  | R10 | ACGCGCGATACCTA |  | 302 |
|  | Probe10 | TTCGACGGGGGCGATTCGGTGCGTA |  | 303 |
| 307 | F10-25 | GTAAGTATTTCGAA | 116 | 327 |
|  | R10 | ACGCGCGATACCTA |  | 302 |
|  | Probe10 | TTCGACGGGGGCGATTCGGTGCGTA |  | 303 |
| 308 | F10-26 | TAAGTATTTCGAAT | 115 | 328 |
|  | R10 | ACGCGCGATACCTA |  | 302 |
|  | Probe10 | TTCGACGGGGGCGATTCGGTGCGTA |  | 303 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 309 | F10-27 | AAGTATTTCGAATT | 114 | 329 |
|  | R10 | ACGCGCGATACCTA |  | 302 |
|  | Probe10 | TTCGACGGGGGCGATTCGGTGCGTA |  | 303 |
| 310 | F10-28 | AGTATTTCGAATTG | 113 | 330 |
|  | R10 | ACGCGCGATACCTA |  | 302 |
|  | Probe10 | TTCGACGGGGGCGATTCGGTGCGTA |  | 303 |
| 311 | F10-29 | GTATTTCGAATTGG | 112 | 331 |
|  | R10 | ACGCGCGATACCTA |  | 302 |
|  | Probe10 | TTCGACGGGGGCGATTCGGTGCGTA |  | 303 |
| 312 | F10-30 | TATTTCGAATTGGT | 111 | 332 |
|  | R10 | ACGCGCGATACCTA |  | 302 |
|  | Probe10 | TTCGACGGGGGCGATTCGGTGCGTA |  | 303 |
| 313 | F10-31 | ATTTCGAATTGGTG | 110 | 333 |
|  | R10 | ACGCGCGATACCTA |  | 302 |
|  | Probe10 | TTCGACGGGGGCGATTCGGTGCGTA |  | 303 |
| 314 | F10-32 | TTTCGAATTGGTGT | 109 | 334 |
|  | R10 | ACGCGCGATACCTA |  | 302 |
|  | Probe10 | TTCGACGGGGGCGATTCGGTGCGTA |  | 303 |
| 315 | F10-33 | TTCGAATTGGTGTT | 108 | 335 |
|  | R10 | ACGCGCGATACCTA |  | 302 |
|  | Probe10 | TTCGACGGGGGCGATTCGGTGCGTA |  | 303 |
| 316 | F10-34 | TCGAATTGGTGTTG | 107 | 336 |
|  | R10 | ACGCGCGATACCTA |  | 302 |
|  | Probe10 | TTCGACGGGGGCGATTCGGTGCGTA |  | 303 |
| 317 | F10-35 | CGAATTGGTGTTGA | 106 | 337 |
|  | R10 | ACGCGCGATACCTA |  | 302 |
|  | Probe10 | TTCGACGGGGGCGATTCGGTGCGTA |  | 303 |
| 318 | F10-36 | GAATTGGTGTTGAA | 105 | 338 |
|  | R10 | ACGCGCGATACCTA |  | 302 |
|  | Probe10 | TTCGACGGGGGCGATTCGGTGCGTA |  | 303 |
| 319 | F10-37 | AATTGGTGTTGAAA | 104 | 339 |
|  | R10 | ACGCGCGATACCTA |  | 302 |
|  | Probe10 | TTCGACGGGGGCGATTCGGTGCGTA |  | 303 |
| 320 | F10-38 | ATTGGTGTTGAAAC | 103 | 340 |
|  | R10 | ACGCGCGATACCTA |  | 302 |
|  | Probe10 | TTCGACGGGGGCGATTCGGTGCGTA |  | 303 |
| 321 | F10-39 | TTGGTGTTGAAACG | 102 | 341 |
|  | R10 | ACGCGCGATACCTA |  | 302 |
|  | Probe10 | TTCGACGGGGGCGATTCGGTGCGTA |  | 303 |
| 322 | F10-40 | TGGTGTTGAAACGC | 101 | 342 |
|  | R10 | ACGCGCGATACCTA |  | 302 |
|  | Probe10 | TTCGACGGGGGCGATTCGGTGCGTA |  | 303 |
| 323 | F10-41 | GGTGTTGAAACGCG | 100 | 343 |
|  | R10 | ACGCGCGATACCTA |  | 302 |
|  | Probe10 | TTCGACGGGGGCGATTCGGTGCGTA |  | 303 |
| 324 | F10-42 | GTGTTGAAACGCGT | 99 | 344 |
|  | R10 | ACGCGCGATACCTA |  | 302 |
|  | Probe10 | TTCGACGGGGGCGATTCGGTGCGTA |  | 303 |
| 325 | F10-43 | TGTTGAAACGCGTT | 98 | 345 |
|  | R10 | ACGCGCGATACCTA |  | 302 |
|  | Probe10 | TTCGACGGGGGCGATTCGGTGCGTA |  | 303 |
| 326 | F10-44 | GTTGAAACGCGTTT | 97 | 346 |
|  | R10 | ACGCGCGATACCTA |  | 302 |
|  | Probe10 | TTCGACGGGGGCGATTCGGTGCGTA |  | 303 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 327 | F10-45 | TTGAAACGCGTTTT | 96 | 347 |
|  | R10 | ACGCGCGATACCTA |  | 302 |
|  | Probe10 | TTCGACGGGGGCGATTCGGTGCGTA |  | 303 |
| 328 | F10-46 | TGAAACGCGTTTTG | 95 | 348 |
|  | R10 | ACGCGCGATACCTA |  | 302 |
|  | Probe10 | TTCGACGGGGGCGATTCGGTGCGTA |  | 303 |
| 329 | F10-47 | GAAACGCGTTTTGG | 94 | 349 |
|  | R10 | ACGCGCGATACCTA |  | 302 |
|  | Probe10 | TTCGACGGGGGCGATTCGGTGCGTA |  | 303 |
| 330 | F10-48 | AAACGCGTTTTGGA | 93 | 350 |
|  | R10 | ACGCGCGATACCTA |  | 302 |
|  | Probe10 | TTCGACGGGGGCGATTCGGTGCGTA |  | 303 |
| 331 | F10-49 | AACGCGTTTTGGAT | 92 | 351 |
|  | R10 | ACGCGCGATACCTA |  | 302 |
|  | Probe10 | TTCGACGGGGGCGATTCGGTGCGTA |  | 303 |
| 332 | F10-50 | ACGCGTTTTGGATC | 91 | 352 |
|  | R10 | ACGCGCGATACCTA |  | 302 |
|  | Probe10 | TTCGACGGGGGCGATTCGGTGCGTA |  | 303 |
| 333 | F10-51 | CGCGTTTTGGATCG | 90 | 353 |
|  | R10 | ACGCGCGATACCTA |  | 302 |
|  | Probe10 | TTCGACGGGGGCGATTCGGTGCGTA |  | 303 |
| 334 | F10-52 | GCGTTTTGGATCGC | 89 | 354 |
|  | R10 | ACGCGCGATACCTA |  | 302 |
|  | Probe10 | TTCGACGGGGGCGATTCGGTGCGTA |  | 303 |
| 335 | F10-53 | CGTTTTGGATCGCG | 88 | 355 |
|  | R10 | ACGCGCGATACCTA |  | 302 |
|  | Probe10 | TTCGACGGGGGCGATTCGGTGCGTA |  | 303 |
| 336 | F10-54 | GTTTTGGATCGCGA | 87 | 356 |
|  | R10 | ACGCGCGATACCTA |  | 302 |
|  | Probe10 | TTCGACGGGGGCGATTCGGTGCGTA |  | 303 |
| 337 | F10-55 | TTTTGGATCGCGAA | 86 | 357 |
|  | R10 | ACGCGCGATACCTA |  | 302 |
|  | Probe10 | TTCGACGGGGGCGATTCGGTGCGTA |  | 303 |
| 338 | F10-56 | TTTGGATCGCGAAG | 85 | 358 |
|  | R10 | ACGCGCGATACCTA |  | 302 |
|  | Probe10 | TTCGACGGGGGCGATTCGGTGCGTA |  | 303 |
| 339 | F10-57 | TTGGATCGCGAAGA | 84 | 359 |
|  | R10 | ACGCGCGATACCTA |  | 302 |
|  | Probe10 | TTCGACGGGGGCGATTCGGTGCGTA |  | 303 |
| 340 | F11-1 | CGGATGTATTTAGATAC | 134 | 360 |
|  | R11 | TACCTCTAAAAATA |  | 361 |
|  | Probe11 | CGCGGAGCGCGGAGTTCGTA |  | 362 |
| 341 | F11-2 | GGATGTATTTAGATAC | 133 | 363 |
|  | R11 | TACCTCTAAAAATA |  | 361 |
|  | Probe11 | CGCGGAGCGCGGAGTTCGTA |  | 362 |
| 342 | F11-3 | CGTTATTTAGTTTC | 118 | 364 |
|  | R11 | TACCTCTAAAAATA |  | 361 |
|  | Probe11 | CGCGGAGCGCGGAGTTCGTA |  | 362 |
| 343 | F11-4 | GTTATTTAGTTTCG | 117 | 365 |
|  | R11 | TACCTCTAAAAATA |  | 361 |
|  | Probe11 | CGCGGAGCGCGGAGTTCGTA |  | 362 |
| 344 | F12-1 | AGTTTCGGGAGTTC | 118 | 366 |
|  | R12 | TCCTCCCGATCTAT |  | 367 |
|  | Probe12 | CGGTAGTTTGGTTACGGCGGGTAGG |  | 368 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 345 | F12-2 | GTTTCGGGAGTTCG | 117 | 369 |
|  | R12 | TCCTCCCGATCTAT |  | 367 |
|  | Probe12 | CGGTAGTTTGGTTACGGCGGGTAGG |  | 368 |
| 346 | F12-3 | TTTCGGGAGTTCGC | 116 | 370 |
|  | R12 | TCCTCCCGATCTAT |  | 367 |
|  | Probe12 | CGGTAGTTTGGTTACGGCGGGTAGG |  | 368 |
| 347 | F12-4 | TTCGGGAGTTCGCG | 115 | 371 |
|  | R12 | TCCTCCCGATCTAT |  | 367 |
|  | Probe12 | CGGTAGTTTGGTTACGGCGGGTAGG |  | 368 |
| 348 | F12-5 | TCGGGAGTTCGCGG | 114 | 372 |
|  | R12 | TCCTCCCGATCTAT |  | 367 |
|  | Probe12 | CGGTAGTTTGGTTACGGCGGGTAGG |  | 368 |
| 349 | F12-6 | CGGGAGTTCGCGGA | 113 | 373 |
|  | R12 | TCCTCCCGATCTAT |  | 367 |
|  | Probe12 | CGGTAGTTTGGTTACGGCGGGTAGG |  | 368 |
| 350 | F12-7 | GGGAGTTCGCGGAG | 112 | 374 |
|  | R12 | TCCTCCCGATCTAT |  | 367 |
|  | Probe12 | CGGTAGTTTGGTTACGGCGGGTAGG |  | 368 |
| 351 | F12-8 | GGAGTTCGCGGAGC | 111 | 375 |
|  | R12 | TCCTCCCGATCTAT |  | 367 |
|  | Probe12 | CGGTAGTTTGGTTACGGCGGGTAGG |  | 368 |
| 352 | F12-9 | GAGTTCGCGGAGCG | 110 | 376 |
|  | R12 | TCCTCCCGATCTAT |  | 367 |
|  | Probe12 | CGGTAGTTTGGTTACGGCGGGTAGG |  | 368 |
| 353 | F12-10 | AGTTCGCGGAGCGC | 109 | 377 |
|  | R12 | TCCTCCCGATCTAT |  | 367 |
|  | Probe12 | CGGTAGTTTGGTTACGGCGGGTAGG |  | 368 |
| 354 | F12-11 | GTTCGCGGAGCGCG | 108 | 378 |
|  | R12 | TCCTCCCGATCTAT |  | 367 |
|  | Probe12 | CGGTAGTTTGGTTACGGCGGGTAGG |  | 368 |
| 355 | F12-12 | TTCGCGGAGCGCGG | 107 | 379 |
|  | R12 | TCCTCCCGATCTAT |  | 367 |
|  | Probe12 | CGGTAGTTTGGTTACGGCGGGTAGG |  | 368 |
| 356 | F12-13 | TCGCGGAGCGCGGA | 106 | 380 |
|  | R12 | TCCTCCCGATCTAT |  | 367 |
|  | Probe12 | CGGTAGTTTGGTTACGGCGGGTAGG |  | 368 |
| 357 | F12-14 | CGCGGAGCGCGGAG | 105 | 381 |
|  | R12 | TCCTCCCGATCTAT |  | 367 |
|  | Probe12 | CGGTAGTTTGGTTACGGCGGGTAGG |  | 368 |
| 358 | F12-15 | GCGGAGCGCGGAGT | 104 | 382 |
|  | R12 | TCCTCCCGATCTAT |  | 367 |
|  | Probe12 | CGGTAGTTTGGTTACGGCGGGTAGG |  | 368 |
| 359 | F12-16 | CGGAGCGCGGAGTT | 103 | 383 |
|  | R12 | TCCTCCCGATCTAT |  | 367 |
|  | Probe12 | CGGTAGTTTGGTTACGGCGGGTAGG |  | 368 |
| 360 | F12-17 | GGAGCGCGGAGTTC | 102 | 384 |
|  | R12 | TCCTCCCGATCTAT |  | 367 |
|  | Probe12 | CGGTAGTTTGGTTACGGCGGGTAGG |  | 368 |
| 361 | F12-18 | GAGCGCGGAGTTCG | 101 | 385 |
|  | R12 | TCCTCCCGATCTAT |  | 367 |
|  | Probe12 | CGGTAGTTTGGTTACGGCGGGTAGG |  | 368 |
| 362 | F12-19 | AGCGCGGAGTTCGT | 100 | 386 |
|  | R12 | TCCTCCCGATCTAT |  | 367 |
|  | Probe12 | CGGTAGTTTGGTTACGGCGGGTAGG |  | 368 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 363 | F12-20 | GCGCGGAGTTCGTA | 99 | 387 |
|  | R12 | TCCTCCCGATCTAT |  | 367 |
|  | Probe12 | CGGTAGTTTGGTTACGGCGGGTAGG |  | 368 |
| 364 | F12-21 | CGCGGAGTTCGTAT | 98 | 388 |
|  | R12 | TCCTCCCGATCTAT |  | 367 |
|  | Probe12 | CGGTAGTTTGGTTACGGCGGGTAGG |  | 368 |
| 365 | F12-22 | GCGGAGTTCGTATT | 97 | 389 |
|  | R12 | TCCTCCCGATCTAT |  | 367 |
|  | Probe12 | CGGTAGTTTGGTTACGGCGGGTAGG |  | 368 |
| 366 | F12-23 | CGGAGTTCGTATTA | 96 | 390 |
|  | R12 | TCCTCCCGATCTAT |  | 367 |
|  | Probe12 | CGGTAGTTTGGTTACGGCGGGTAGG |  | 368 |
| 367 | F12-24 | GGAGTTCGTATTAT | 95 | 391 |
|  | R12 | TCCTCCCGATCTAT |  | 367 |
|  | Probe12 | CGGTAGTTTGGTTACGGCGGGTAGG |  | 368 |
| 368 | F12-30 | CGTATTATTTTAGAGGTAGGAC | 89 | 392 |
|  | R12 | TCCTCCCGATCTAT |  | 367 |
|  | Probe12 | CGGTAGTTTGGTTACGGCGGGTAGG |  | 368 |
| 369 | F13-1 | GGACGTAGTTTTTC | 140 | 393 |
|  | R13 | ATATATTTTCACTT |  | 394 |
|  | Probe13 | AATTTAGATATTTTGATGGAGGATA |  | 395 |
| 370 | F13-2 | GACGTAGTTTTTCG | 139 | 396 |
|  | R13 | ATATATTTTCACTT |  | 394 |
|  | Probe13 | AATTTAGATATTTTGATGGAGGATA |  | 395 |
| 371 | F13-3 | ACGTAGTTTTTCGT | 138 | 397 |
|  | R13 | ATATATTTTCACTT |  | 394 |
|  | Probe13 | AATTTAGATATTTTGATGGAGGATA |  | 395 |
| 372 | F13-4 | CGTAGTTTTTCGTT | 137 | 398 |
|  | R13 | ATATATTTTCACTT |  | 394 |
|  | Probe13 | AATTTAGATATTTTGATGGAGGATA |  | 395 |
| 373 | F13-5 | CGTAGTTTTTCGTTTTGAATTC | 137 | 399 |
|  | R13 | ATATATTTTCACTT |  | 394 |
|  | Probe13 | AATTTAGATATTTTGATGGAGGATA |  | 395 |
| 374 | F13-6 | TTCGTTTTGAATTC | 129 | 400 |
|  | R13 | ATATATTTTCACTT |  | 394 |
|  | Probe13 | AATTTAGATATTTTGATGGAGGATA |  | 395 |
| 375 | F13-7 | TCGTTTTGAATTCG | 128 | 401 |
|  | R13 | ATATATTTTCACTT |  | 394 |
|  | Probe13 | AATTTAGATATTTTGATGGAGGATA |  | 395 |
| 376 | F13-8 | CGTTTTGAATTCGC | 127 | 402 |
|  | R13 | ATATATTTTCACTT |  | 394 |
|  | Probe13 | AATTTAGATATTTTGATGGAGGATA |  | 395 |
| 377 | F13-9 | GTTTTGAATTCGCG | 126 | 403 |
|  | R13 | ATATATTTTCACTT |  | 394 |
|  | Probe13 | AATTTAGATATTTTGATGGAGGATA |  | 395 |
| 378 | F13-10 | TTTTGAATTCGCGT | 125 | 404 |
|  | R13 | ATATATTTTCACTT |  | 394 |
|  | Probe13 | AATTTAGATATTTTGATGGAGGATA |  | 395 |
| 379 | F13-11 | TTTGAATTCGCGTA | 124 | 405 |
|  | R13 | ATATATTTTCACTT |  | 394 |
|  | Probe13 | AATTTAGATATTTTGATGGAGGATA |  | 395 |
| 380 | F13-12 | TTGAATTCGCGTAG | 123 | 406 |
|  | R13 | ATATATTTTCACTT |  | 394 |
|  | Probe13 | AATTTAGATATTTTGATGGAGGATA |  | 395 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 381 | F13-13 | TGAATTCGCGTAGC | 122 | 407 |
|  | R13 | ATATATTTTCACTT |  | 394 |
|  | Probe13 | AATTTAGATATTTTGATGGAGGATA |  | 395 |
| 382 | F13-14 | GAATTCGCGTAGCG | 121 | 408 |
|  | R13 | ATATATTTTCACTT |  | 394 |
|  | Probe13 | AATTTAGATATTTTGATGGAGGATA |  | 395 |
| 383 | F13-15 | AATTCGCGTAGCGG | 120 | 409 |
|  | R13 | ATATATTTTCACTT |  | 394 |
|  | Probe13 | AATTTAGATATTTTGATGGAGGATA |  | 395 |
| 384 | F13-16 | ATTCGCGTAGCGGT | 119 | 410 |
|  | R13 | ATATATTTTCACTT |  | 394 |
|  | Probe13 | AATTTAGATATTTTGATGGAGGATA |  | 395 |
| 385 | F13-17 | TTCGCGTAGCGGTA | 118 | 411 |
|  | R13 | ATATATTTTCACTT |  | 394 |
|  | Probe13 | AATTTAGATATTTTGATGGAGGATA |  | 395 |
| 386 | F13-18 | TCGCGTAGCGGTAG | 117 | 412 |
|  | R13 | ATATATTTTCACTT |  | 394 |
|  | Probe13 | AATTTAGATATTTTGATGGAGGATA |  | 395 |
| 387 | F13-19 | CGCGTAGCGGTAGT | 116 | 413 |
|  | R13 | ATATATTTTCACTT |  | 394 |
|  | Probe13 | AATTTAGATATTTTGATGGAGGATA |  | 395 |
| 388 | F13-20 | GCGTAGCGGTAGTT | 115 | 414 |
|  | R13 | ATATATTTTCACTT |  | 394 |
|  | Probe13 | AATTTAGATATTTTGATGGAGGATA |  | 395 |
| 389 | F13-21 | CGTAGCGGTAGTTT | 114 | 415 |
|  | R13 | ATATATTTTCACTT |  | 394 |
|  | Probe13 | AATTTAGATATTTTGATGGAGGATA |  | 395 |
| 390 | F13-22 | GTAGCGGTAGTTTG | 113 | 416 |
|  | R13 | ATATATTTTCACTT |  | 394 |
|  | Probe13 | AATTTAGATATTTTGATGGAGGATA |  | 395 |
| 391 | F13-23 | CGGTAGTTTGGTTAC | 109 | 417 |
|  | R13 | ATATATTTTCACTT |  | 394 |
|  | Probe13 | AATTTAGATATTTTGATGGAGGATA |  | 395 |
| 392 | F13-24 | GGTAGTTTGGTTAC | 108 | 418 |
|  | R13 | ATATATTTTCACTT |  | 394 |
|  | Probe13 | AATTTAGATATTTTGATGGAGGATA |  | 395 |
| 393 | F13-25 | AGTTTGGTTACGGC | 105 | 419 |
|  | R13 | ATATATTTTCACTT |  | 394 |
|  | Probe13 | AATTTAGATATTTTGATGGAGGATA |  | 395 |
| 394 | F13-26 | GTTTGGTTACGGCG | 104 | 420 |
|  | R13 | ATATATTTTCACTT |  | 394 |
|  | Probe13 | AATTTAGATATTTTGATGGAGGATA |  | 395 |
| 395 | F13-27 | TTTGGTTACGGCGG | 103 | 421 |
|  | R13 | ATATATTTTCACTT |  | 394 |
|  | Probe13 | AATTTAGATATTTTGATGGAGGATA |  | 395 |
| 396 | F13-28 | TTGGTTACGGCGGG | 102 | 422 |
|  | R13 | ATATATTTTCACTT |  | 394 |
|  | Probe13 | AATTTAGATATTTTGATGGAGGATA |  | 395 |
| 397 | F13-29 | TGGTTACGGCGGGT | 101 | 423 |
|  | R13 | ATATATTTTCACTT |  | 394 |
|  | Probe13 | AATTTAGATATTTTGATGGAGGATA |  | 395 |
| 398 | F13-30 | GGTTACGGCGGGTA | 100 | 424 |
|  | R13 | ATATATTTTCACTT |  | 394 |
|  | Probe13 | AATTTAGATATTTTGATGGAGGATA |  | 395 |

TABLE 3-continued

Sequences of primer and probes for PCDHGA12 gene qMSP

| Set | Primer | Sequence (5'→3') | Size of amplified product (bp) | Sequence No. |
|---|---|---|---|---|
| 399 | F13-31 | GTTACGGCGGGTAG | 99 | 425 |
|  | R13 | ATATATTTTCACTT |  | 394 |
|  | Probe13 | AATTTAGATATTTTGATGGAGGATA |  | 395 |
| 400 | F13-32 | TTACGGCGGGTAGG | 98 | 426 |
|  | R13 | ATATATTTTCACTT |  | 394 |
|  | Probe13 | AATTTAGATATTTTGATGGAGGATA |  | 395 |
| 401 | F13-33 | TACGGCGGGTAGGA | 97 | 427 |
|  | R13 | ATATATTTTCACTT |  | 394 |
|  | Probe13 | AATTTAGATATTTTGATGGAGGATA |  | 395 |
| 402 | F13-34 | ACGGCGGGTAGGAT | 96 | 428 |
|  | R13 | ATATATTTTCACTT |  | 394 |
|  | Probe13 | AATTTAGATATTTTGATGGAGGATA |  | 395 |
| 403 | F13-35 | CGGCGGGTAGGATA | 95 | 429 |
|  | R13 | ATATATTTTCACTT |  | 394 |
|  | Probe13 | AATTTAGATATTTTGATGGAGGATA |  | 395 |
| 404 | F13-36 | GGCGGGTAGGATAG | 94 | 430 |
|  | R13 | ATATATTTTCACTT |  | 394 |
|  | Probe13 | AATTTAGATATTTTGATGGAGGATA |  | 395 |
| 405 | F13-37 | CGGGTAGGATAGATC | 92 | 431 |
|  | R13 | ATATATTTTCACTT |  | 394 |
|  | Probe13 | AATTTAGATATTTTGATGGAGGATA |  | 395 |
| 406 | F13-38 | GGGTAGGATAGATC | 91 | 432 |
|  | R13 | ATATATTTTCACTT |  | 394 |
|  | Probe13 | AATTTAGATATTTTGATGGAGGATA |  | 395 |
| 407 | F14-1 | ATTCGGTICGTATAGGTATCGC | 110 | 433 |
|  | R14 | CAAATTCTCCGAAACGITCGCG |  | 434 |
|  | Probe14 | CGTATTCGCGTGATGGTTTTGGATGC |  | 435 |

As a result of evaluating methylation of PCDHGA12 gene using blood serum DNA from normal person and lung cancer patient, it was found that the sensitivity of PCDHGA12 gene for lung cancer diagnosis was 75% (15/20) ~90.0% (18/20) and the specificity of the PCDHGA12 gene was 85% (3/20)~95% (1/20). Such results suggest that the PCDHGA12 methylation is useful for diagnosis of lung cancer.

TABLE 4

Evaluation of ability to diagnose lung cancer using PCDHGA12 gene

| Set of primers and probes | Cut-off (PMR) | Sensitivity (%), n = 20 | Specificity (%), n = 20 |
|---|---|---|---|
| 1 | >0.4 | 85 | 85 |
| 2 | >4.2 | 75 | 95 |
| 3 | >3.3 | 85 | 90 |
| 4 | >3.2 | 90 | 85 |
| 5 | >2.3 | 90 | 85 |
| 6 | >5.7 | 80 | 95 |
| 7 | >2.3 | 85 | 90 |
| 8 | >3.0 | 85 | 90 |
| 9 | >2.0 | 85 | 85 |
| 10 | >2.1 | 90 | 85 |
| 11 | >0.5 | 80 | 90 |
| 12 | >2.2 | 85 | 90 |
| 13 | >3.5 | 75 | 95 |
| 14 | >3.6 | 75 | 95 |
| 15 | >2.3 | 80 | 90 |
| 16 | >2.4 | 85 | 90 |
| 17 | >1.2 | 80 | 90 |
| 18 | >4.3 | 80 | 95 |
| 19 | >2.9 | 85 | 90 |
| 20 | >2.1 | 85 | 90 |
| 21 | >2.7 | 80 | 90 |
| 22 | >0.4 | 85 | 90 |
| 23 | >1.2 | 85 | 85 |
| 24 | >2.7 | 90 | 85 |
| 25 | >4.5 | 80 | 85 |
| 26 | >2.1 | 75 | 90 |
| 27 | >0.7 | 85 | 85 |
| 28 | >0.4 | 90 | 85 |
| 29 | >4.2 | 90 | 85 |
| 30 | >3.3 | 80 | 90 |
| 31 | >3.2 | 85 | 90 |
| 32 | >2.3 | 80 | 90 |
| 33 | >5.7 | 75 | 95 |
| 34 | >2.3 | 75 | 95 |
| 35 | >3.0 | 85 | 90 |
| 36 | >2.0 | 80 | 90 |
| 37 | >2.1 | 85 | 85 |
| 38 | >0.5 | 80 | 90 |
| 39 | >2.2 | 85 | 90 |
| 40 | >3.5 | 75 | 90 |
| 41 | >3.6 | 85 | 90 |
| 42 | >2.3 | 85 | 90 |
| 43 | >2.4 | 85 | 90 |
| 44 | >1.2 | 90 | 80 |

TABLE 4-continued

Evaluation of ability to diagnose lung cancer using PCDHGA12 gene

| Set of primers and probes | Cut-off (PMR) | Sensitivity (%), n = 20 | Specificity (%), n = 20 |
| --- | --- | --- | --- |
| 45 | >4.3 | 75 | 90 |
| 46 | >2.9 | 85 | 90 |
| 47 | >2.1 | 75 | 90 |
| 48 | >2.7 | 85 | 85 |
| 49 | >0.4 | 80 | 90 |
| 50 | >1.2 | 75 | 90 |
| 51 | >2.7 | 80 | 90 |
| 52 | >4.5 | 75 | 95 |
| 53 | >2.1 | 80 | 95 |
| 54 | >0.7 | 90 | 85 |
| 55 | >0.4 | 85 | 85 |
| 56 | >4.2 | 75 | 90 |
| 57 | >3.3 | 80 | 90 |
| 58 | >3.2 | 85 | 90 |
| 59 | >2.3 | 85 | 85 |
| 60 | >5.7 | 75 | 90 |
| 61 | >2.3 | 80 | 90 |
| 62 | >3.0 | 75 | 95 |
| 63 | >2.0 | 80 | 95 |
| 64 | >2.1 | 80 | 90 |
| 65 | >0.5 | 85 | 85 |
| 66 | >2.2 | 85 | 85 |
| 67 | >3.5 | 85 | 90 |
| 68 | >3.6 | 75 | 85 |
| 69 | >2.3 | 85 | 90 |
| 70 | >2.4 | 80 | 90 |
| 71 | >1.2 | 80 | 85 |
| 72 | >4.3 | 80 | 85 |
| 73 | >2.9 | 75 | 95 |
| 74 | >2.1 | 80 | 90 |
| 75 | >2.7 | 85 | 90 |
| 76 | >0.4 | 90 | 85 |
| 77 | >1.2 | 90 | 85 |
| 78 | >2.7 | 85 | 90 |
| 79 | >4.5 | 80 | 90 |
| 80 | >2.1 | 75 | 85 |
| 81 | >0.4 | 85 | 90 |
| 82 | >2.3 | 75 | 95 |
| 83 | >2.7 | 85 | 85 |
| 84 | >4.5 | 90 | 80 |
| 85 | >2.4 | 85 | 90 |
| 86 | >2.7 | 90 | 80 |
| 87 | >3.5 | 85 | 85 |
| 88 | >2.9 | 80 | 90 |
| 89 | >2.7 | 90 | 80 |
| 90 | >3.3 | 90 | 85 |
| 91 | >3.2 | 80 | 85 |
| 92 | >2.3 | 75 | 90 |
| 93 | >2.4 | 80 | 90 |
| 94 | >0.4 | 85 | 90 |
| 95 | >1.2 | 75 | 85 |
| 96 | >4.3 | 85 | 90 |
| 97 | >2.9 | 75 | 95 |
| 98 | >4.5 | 75 | 95 |
| 99 | >2.3 | 75 | 90 |
| 100 | >0.4 | 80 | 85 |
| 101 | >2.2 | 80 | 90 |
| 102 | >4.2 | 80 | 90 |
| 103 | >2.0 | 75 | 90 |
| 104 | >2.1 | 80 | 90 |
| 105 | >0.4 | 85 | 85 |
| 106 | >5.7 | 80 | 85 |
| 107 | >2.9 | 90 | 85 |
| 108 | >3.6 | 85 | 85 |
| 109 | >2.7 | 85 | 90 |
| 110 | >2.9 | 85 | 85 |
| 111 | >4.5 | 85 | 90 |
| 112 | >0.5 | 85 | 90 |
| 113 | >1.2 | 85 | 90 |
| 114 | >3.3 | 85 | 90 |
| 115 | >2.1 | 85 | 85 |
| 116 | >2.3 | 80 | 95 |
| 117 | >4.3 | 90 | 85 |
| 118 | >2.1 | 85 | 90 |
| 119 | >0.4 | 85 | 85 |
| 120 | >3.0 | 75 | 90 |
| 121 | >3.6 | 75 | 95 |
| 122 | >0.7 | 75 | 90 |
| 123 | >5.7 | 85 | 95 |
| 124 | >3.2 | 85 | 90 |
| 125 | >2.1 | 80 | 95 |
| 126 | >1.2 | 80 | 95 |
| 127 | >4.3 | 80 | 90 |
| 128 | >2.3 | 90 | 85 |
| 129 | >0.4 | 75 | 90 |
| 130 | >2.9 | 85 | 90 |
| 131 | >3.6 | 75 | 90 |
| 132 | >0.7 | 90 | 90 |
| 133 | >5.7 | 80 | 90 |
| 134 | >3.2 | 85 | 90 |
| 135 | >2.1 | 85 | 85 |
| 136 | >1.2 | 85 | 90 |
| 137 | >4.2 | 80 | 90 |
| 138 | >2.3 | 90 | 85 |
| 139 | >0.5 | 85 | 85 |
| 140 | >2.9 | 85 | 95 |
| 141 | >3.3 | 80 | 95 |
| 142 | >0.5 | 90 | 90 |
| 143 | >5.7 | 80 | 90 |
| 144 | >3.5 | 75 | 90 |
| 145 | >3.6 | 85 | 85 |
| 146 | >2.1 | 80 | 90 |
| 147 | >0.5 | 80 | 90 |
| 148 | >1.2 | 80 | 90 |
| 149 | >4.3 | 85 | 90 |
| 150 | >3.6 | 85 | 85 |
| 151 | >2.7 | 85 | 95 |
| 152 | >0.7 | 80 | 90 |
| 153 | >4.2 | 75 | 95 |
| 154 | >2.7 | 75 | 85 |
| 155 | >2.0 | 85 | 90 |
| 156 | >0.5 | 85 | 90 |
| 157 | >2.3 | 75 | 90 |
| 158 | >2.7 | 85 | 85 |
| 159 | >3.2 | 85 | 90 |
| 160 | >2.3 | 80 | 90 |
| 161 | >2.3 | 85 | 85 |
| 162 | >4.3 | 90 | 90 |
| 163 | >2.1 | 90 | 80 |
| 164 | >2.4 | 80 | 85 |
| 165 | >1.2 | 85 | 90 |
| 166 | >2.2 | 90 | 85 |
| 167 | >2.7 | 90 | 85 |
| 168 | >2.1 | 80 | 90 |
| 169 | >2.7 | 80 | 90 |
| 170 | >1.2 | 75 | 95 |
| 171 | >4.3 | 80 | 90 |
| 172 | >3.6 | 80 | 95 |
| 173 | >2.4 | 80 | 90 |
| 174 | >0.7 | 85 | 90 |
| 175 | >1.2 | 85 | 95 |
| 176 | >2.7 | 85 | 90 |
| 177 | >2.1 | 85 | 90 |
| 178 | >2.7 | 80 | 90 |
| 179 | >5.7 | 90 | 80 |
| 180 | >3.5 | 85 | 85 |
| 181 | >3.3 | 85 | 90 |
| 182 | >2.1 | 85 | 90 |
| 183 | >0.5 | 85 | 90 |
| 184 | >2.2 | 90 | 85 |
| 185 | >2.9 | 75 | 90 |
| 186 | >2.1 | 80 | 90 |
| 187 | >2.3 | 75 | 90 |
| 188 | >1.2 | 90 | 80 |
| 189 | >3.5 | 85 | 85 |
| 190 | >4.5 | 85 | 90 |
| 191 | >2.1 | 75 | 95 |
| 192 | >0.5 | 80 | 90 |
| 193 | >1.2 | 90 | 80 |
| 194 | >4.3 | 85 | 85 |

TABLE 4-continued

Evaluation of ability to diagnose lung cancer using PCDHGA12 gene

| Set of primers and probes | Cut-off (PMR) | Sensitivity (%), n = 20 | Specificity (%), n = 20 |
|---|---|---|---|
| 195 | >3.2 | 80 | 95 |
| 196 | >2.4 | 75 | 90 |
| 197 | >0.4 | 80 | 85 |
| 198 | >4.2 | 75 | 95 |
| 199 | >2.7 | 80 | 90 |
| 200 | >2.0 | 75 | 90 |
| 201 | >0.4 | 85 | 85 |
| 202 | >5.7 | 85 | 90 |
| 203 | >3.0 | 75 | 85 |
| 204 | >3.3 | 85 | 90 |
| 205 | >2.1 | 85 | 90 |
| 206 | >0.4 | 85 | 90 |
| 207 | >2.2 | 80 | 90 |
| 208 | >3.0 | 75 | 85 |
| 209 | >2.0 | 80 | 90 |
| 210 | >2.3 | 75 | 80 |
| 211 | >1.2 | 90 | 85 |
| 212 | >4.3 | 80 | 85 |
| 213 | >2.1 | 75 | 90 |
| 214 | >2.3 | 85 | 90 |
| 215 | >0.4 | 75 | 90 |
| 216 | >4.2 | 90 | 85 |
| 217 | >2.1 | 85 | 90 |
| 218 | >5.7 | 80 | 90 |
| 219 | >3.0 | 75 | 95 |
| 220 | >2.1 | 85 | 90 |
| 221 | >2.7 | 80 | 95 |
| 222 | >5.7 | 75 | 85 |
| 223 | >3.0 | 80 | 90 |
| 224 | >3.3 | 80 | 90 |
| 225 | >2.4 | 75 | 90 |
| 226 | >1.2 | 90 | 85 |
| 227 | >4.2 | 85 | 85 |
| 228 | >3.2 | 90 | 85 |
| 229 | >2.3 | 75 | 90 |
| 230 | >0.5 | 80 | 90 |
| 231 | >1.2 | 90 | 80 |
| 232 | >3.0 | 85 | 85 |
| 233 | >2.0 | 75 | 90 |
| 234 | >2.4 | 75 | 90 |
| 235 | >0.4 | 75 | 95 |
| 236 | >4.2 | 75 | 90 |
| 237 | >4.5 | 80 | 95 |
| 238 | >2.3 | 85 | 90 |
| 239 | >0.4 | 80 | 90 |
| 240 | >5.7 | 85 | 90 |
| 241 | >3.0 | 80 | 85 |
| 242 | >3.2 | 80 | 85 |
| 243 | >2.3 | 85 | 90 |
| 244 | >0.4 | 90 | 85 |
| 245 | >2.2 | 75 | 95 |
| 246 | >4.5 | 75 | 95 |
| 247 | >2.1 | 80 | 90 |
| 248 | >2.3 | 85 | 90 |
| 249 | >2.3 | 80 | 90 |
| 250 | >4.3 | 80 | 90 |
| 251 | >3.3 | 75 | 95 |
| 252 | >2.4 | 85 | 85 |
| 253 | >0.5 | 85 | 90 |
| 254 | >2.2 | 80 | 85 |
| 255 | >2.7 | 85 | 90 |
| 256 | >2.0 | 85 | 90 |
| 257 | >2.7 | 90 | 85 |
| 258 | >1.2 | 75 | 95 |
| 259 | >4.2 | 90 | 85 |
| 260 | >3.3 | 75 | 90 |
| 261 | >2.3 | 80 | 90 |
| 262 | >0.4 | 85 | 85 |
| 263 | >1.2 | 85 | 90 |
| 264 | >3.0 | 80 | 95 |
| 265 | >2.1 | 85 | 95 |
| 266 | >2.7 | 80 | 85 |
| 267 | >0.4 | 90 | 85 |
| 268 | >3.5 | 75 | 90 |
| 269 | >3.6 | 75 | 85 |
| 270 | >2.1 | 90 | 80 |
| 271 | >0.7 | 80 | 90 |
| 272 | >2.3 | 80 | 90 |
| 273 | >4.3 | 85 | 90 |
| 274 | >2.1 | 80 | 90 |
| 275 | >2.4 | 80 | 90 |
| 276 | >2.9 | 80 | 90 |
| 277 | >2.2 | 80 | 90 |
| 278 | >2.1 | 85 | 85 |
| 279 | >2.1 | 75 | 90 |
| 280 | >0.7 | 85 | 90 |
| 281 | >2.3 | 85 | 85 |
| 282 | >0.7 | 90 | 85 |
| 283 | >2.3 | 80 | 90 |
| 284 | >5.7 | 80 | 90 |
| 285 | >2.3 | 85 | 90 |
| 286 | >0.7 | 75 | 95 |
| 287 | >2.3 | 75 | 90 |
| 288 | >0.4 | 80 | 90 |
| 289 | >2.1 | 80 | 90 |
| 290 | >0.7 | 85 | 85 |
| 291 | >2.3 | 85 | 90 |
| 292 | >0.4 | 90 | 85 |
| 293 | >2.3 | 80 | 85 |
| 294 | >0.4 | 90 | 85 |
| 295 | >2.1 | 75 | 90 |
| 296 | >0.7 | 80 | 90 |
| 297 | >2.1 | 85 | 85 |
| 298 | >2.7 | 85 | 90 |
| 299 | >2.1 | 85 | 90 |
| 300 | >0.5 | 90 | 85 |
| 301 | >2.0 | 75 | 90 |
| 302 | >2.3 | 75 | 95 |
| 303 | >2.1 | 85 | 90 |
| 304 | >2.7 | 75 | 80 |
| 305 | >1.2 | 85 | 90 |
| 306 | >0.4 | 75 | 95 |
| 307 | >1.2 | 80 | 90 |
| 308 | >1.2 | 85 | 90 |
| 309 | >3.2 | 80 | 90 |
| 310 | >4.5 | 85 | 90 |
| 311 | >2.1 | 80 | 85 |
| 312 | >3.3 | 85 | 85 |
| 313 | >2.1 | 90 | 80 |
| 314 | >3.6 | 75 | 90 |
| 315 | >2.1 | 80 | 90 |
| 316 | >2.7 | 75 | 90 |
| 317 | >2.1 | 80 | 90 |
| 318 | >4.5 | 90 | 85 |
| 319 | >2.0 | 80 | 90 |
| 320 | >2.7 | 75 | 90 |
| 321 | >2.0 | 80 | 95 |
| 322 | >3.0 | 85 | 85 |
| 323 | >2.0 | 75 | 90 |
| 324 | >3.0 | 80 | 90 |
| 325 | >2.1 | 75 | 95 |
| 326 | >2.7 | 85 | 90 |
| 327 | >2.1 | 85 | 90 |
| 328 | >2.9 | 85 | 90 |
| 329 | >3.3 | 80 | 90 |
| 330 | >2.7 | 75 | 95 |
| 331 | >3.2 | 85 | 85 |
| 332 | >4.2 | 80 | 90 |
| 333 | >3.2 | 80 | 90 |
| 334 | >0.7 | 75 | 90 |
| 335 | >0.7 | 75 | 90 |
| 336 | >2.3 | 85 | 90 |
| 337 | >0.4 | 85 | 95 |
| 338 | >3.5 | 85 | 90 |
| 339 | >3.0 | 85 | 85 |
| 340 | >0.4 | 80 | 95 |
| 341 | >0.4 | 85 | 90 |
| 342 | >3.5 | 75 | 95 |
| 343 | >4.2 | 80 | 90 |
| 344 | >3.3 | 80 | 90 |

TABLE 4-continued

Evaluation of ability to diagnose lung cancer using PCDHGA12 gene

| Set of primers and probes | Cut-off (PMR) | Sensitivity (%), n = 20 | Specificity (%), n = 20 |
|---|---|---|---|
| 345 | >3.2 | 80 | 90 |
| 346 | >1.2 | 90 | 80 |
| 347 | >5.7 | 90 | 80 |
| 348 | >2.9 | 85 | 90 |
| 349 | >3.5 | 85 | 90 |
| 350 | >2.3 | 75 | 90 |
| 351 | >2.3 | 90 | 85 |
| 352 | >2.3 | 80 | 90 |
| 353 | >5.7 | 80 | 95 |
| 354 | >3.6 | 90 | 85 |
| 355 | >2.0 | 80 | 90 |
| 356 | >0.4 | 75 | 95 |
| 357 | >3.3 | 75 | 90 |
| 358 | >3.6 | 75 | 90 |
| 359 | >2.2 | 90 | 85 |
| 360 | >2.3 | 85 | 90 |
| 361 | >4.3 | 80 | 85 |
| 362 | >2.9 | 85 | 90 |
| 363 | >2.7 | 75 | 85 |
| 364 | >0.5 | 90 | 85 |
| 365 | >1.2 | 75 | 95 |
| 366 | >3.5 | 85 | 90 |
| 367 | >3.6 | 85 | 90 |
| 368 | >3.6 | 80 | 90 |
| 369 | >0.4 | 85 | 85 |
| 370 | >1.2 | 75 | 90 |
| 371 | >4.3 | 80 | 90 |
| 372 | >2.2 | 80 | 90 |
| 373 | >2.4 | 80 | 90 |
| 374 | >2.3 | 80 | 85 |
| 375 | >0.5 | 90 | 85 |
| 376 | >2.1 | 85 | 90 |
| 377 | >2.3 | 80 | 90 |
| 378 | >1.2 | 80 | 95 |
| 379 | >3.5 | 90 | 85 |
| 380 | >3.5 | 85 | 85 |
| 381 | >2.1 | 85 | 90 |
| 382 | >2.4 | 75 | 90 |
| 383 | >2.7 | 80 | 90 |
| 384 | >2.4 | 85 | 85 |
| 385 | >4.5 | 75 | 95 |
| 386 | >0.7 | 85 | 85 |
| 387 | >4.5 | 80 | 90 |
| 388 | >4.5 | 75 | 95 |
| 389 | >3.5 | 85 | 90 |
| 390 | >0.4 | 80 | 90 |
| 391 | >1.2 | 80 | 90 |
| 392 | >2.3 | 85 | 90 |
| 393 | >2.2 | 75 | 95 |
| 394 | >2.3 | 90 | 85 |
| 395 | >4.2 | 85 | 85 |
| 396 | >4.2 | 75 | 90 |
| 397 | >2.3 | 85 | 90 |
| 398 | >1.2 | 80 | 90 |
| 399 | >3.2 | 75 | 90 |
| 400 | >2.2 | 75 | 95 |
| 401 | >2.2 | 85 | 90 |
| 402 | >3.0 | 80 | 90 |
| 403 | >4.5 | 90 | 85 |
| 404 | >2.1 | 80 | 95 |
| 405 | >0.5 | 85 | 90 |
| 406 | >2.0 | 90 | 80 |
| 407 | >2.9 | 80 | 90 |

INDUSTRIAL APPLICABILITY

As described in detail above, the present invention provides the kit for lung cancer diagnosis which can determine the methylation status of CpG in the 5' UTR and exon 1 regions of the lung cancer-specific marker gene. The diagnostic kit according to the present invention makes it possible to diagnose lung cancer at an early stage in an accurate and rapid manner compared to conventional methods and can be used for prognosis and monitoring of lung cancer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for detecting CpG methylation of PCDHGA12 (protocadherin gamma subfamily A, 12), the method comprising the steps of:
    (a) isolating a genomic DNA from a clinical sample;
    (b) treating the genomic DNA from step (a) with bisulfite;
    (c) amplifying the bisulfite treated genomic DNA using a primer pair comprising the sequence of SEQ ID NO 433 and SEQ ID NO 434; and
    (d) determining hypermethylation in the PCDHGA12 gene.

2. The method according to claim 1, wherein step (c) is performed by one selected from the group consisting of PCR, methylation specific PCR, real-time methylation specific PCR, PCR using a methylated DNA-specific binding protein, quantitative PCR, pyrosequencing, and bisulfite sequencing.

3. The method according to claim 1, further comprising probe(s) capable of hybridizing with a methylated CpG of PCDHGA12 comprising at least one or more CpG dinucleotide in a region which hybridizes to the methylated CpG of PCDHGA12.

4. The method according to claim 3, wherein the probe(s) comprise a probe capable of hybridizing with a methylated CpG of PCDHGA12 comprising the sequence of SEQ ID NO: 435.

5. The method according to claim 1, wherein said clinical sample is a lung tissue sample.

* * * * *

UNITED STATES PATENT AND TRADEMARK OFFICE
CERTIFICATE OF CORRECTION

PATENT NO. : 10,767,231 B2  
APPLICATION NO. : 15/814354  
DATED : September 8, 2020  
INVENTOR(S) : An et al.

Page 1 of 1

It is certified that error appears in the above-identified patent and that said Letters Patent is hereby corrected as shown below:

In the Claims

Column 205, Line 48:
"(b) treating the genomic DNA from step (a with bisulfite;"

Should be:
-- (b) treating the genomic DNA from step (a) with bisulfite;

Signed and Sealed this
Twentieth Day of October, 2020

Andrei Iancu
*Director of the United States Patent and Trademark Office*

SEQUENCE LISTING

<160> NUMBER OF SEQ ID NOS: 439

<210> SEQ ID NO 1
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1
aaaggttgtt tatt                                                       14

<210> SEQ ID NO 2
<211> LENGTH: 14
<212> TYPE: DNA
<213> ORGANISM: Artificial Sequence
<220> FEATURE:
<223> OTHER INFORMATION: Synthetic Construct

<400> SEQUENCE: 2
cgctcgcgcg atac                                                       14

```
<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
acgtattagc gtttgtttag ttcga                                          25

<210> SEQ ID NO 4
<211> LENGTH: 14
<212> TYPE: DNA
<213> ORGANISM: Artificial Sequence
<220> FEATURE:
<223> OTHER INFORMATION: Synthetic Construct

<400> SEQUENCE: 4
aaggttgttt atta                                                      14

<210> SEQ ID NO 5
<211> LENGTH: 14
<212> TYPE: DNA
<213> ORGANISM: Artificial Sequence
<220> FEATURE:
<223> OTHER INFORMATION: Synthetic Construct

<400> SEQUENCE: 5
aggttgttta ttat                                                      14

<210> SEQ ID NO 6
<211> LENGTH: 14
<212> TYPE: DNA
<213> ORGANISM: Artificial Sequence
<220> FEATURE:
<223> OTHER INFORMATION: Synthetic Construct

<400> SEQUENCE: 6
ggttgtttat tatt                                                      14

<210> SEQ ID NO 7
<211> LENGTH: 14
<212> TYPE: DNA
<213> ORGANISM: Artificial Sequence
<220> FEATURE:
<223> OTHER INFORMATION: Synthetic Construct

<400> SEQUENCE: 7
gttgtttatt attt                                                      14

<210> SEQ ID NO 8
<211> LENGTH: 14
<212> TYPE: DNA
<213> ORGANISM: Artificial Sequence
<220> FEATURE:
<223> OTHER INFORMATION: Synthetic Construct

<400> SEQUENCE: 8
ttgtttatta tttg                                                      14

<210> SEQ ID NO 9
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 9
tgtttattat ttgg                                                        14

<210> SEQ ID NO 10
<211> LENGTH: 14
<212> TYPE: DNA
<213> ORGANISM: Artificial Sequence
<220> FEATURE:
<223> OTHER INFORMATION: Synthetic Construct

<400> SEQUENCE: 10
gtttattatt tggt                                                        14

<210> SEQ ID NO 11
<211> LENGTH: 14
<212> TYPE: DNA
<213> ORGANISM: Artificial Sequence
<220> FEATURE:
<223> OTHER INFORMATION: Synthetic Construct

<400> SEQUENCE: 11
tttattattt ggtt                                                        14

<210> SEQ ID NO 12
<211> LENGTH: 14
<212> TYPE: DNA
<213> ORGANISM: Artificial Sequence
<220> FEATURE:
<223> OTHER INFORMATION: Synthetic Construct

<400> SEQUENCE: 12
ttattatttg gttt                                                        14

<210> SEQ ID NO 13
<211> LENGTH: 14
<212> TYPE: DNA
<213> ORGANISM: Artificial Sequence
<220> FEATURE:
<223> OTHER INFORMATION: Synthetic Construct

<400> SEQUENCE: 13
tattatttgg tttt                                                        14

<210> SEQ ID NO 14
<211> LENGTH: 14
<212> TYPE: DNA
<213> ORGANISM: Artificial Sequence
<220> FEATURE:
<223> OTHER INFORMATION: Synthetic Construct

<400> SEQUENCE: 14
attatttggt tttt                                                        14

<210> SEQ ID NO 15
<211> LENGTH: 14
<212> TYPE: DNA
<213> ORGANISM: Artificial Sequence
<220> FEATURE:
<223> OTHER INFORMATION: Synthetic Construct

<400> SEQUENCE: 15
ttatttggtt ttta                                                        14

<210> SEQ ID NO 16
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 16
tatttggttt ttac                                                         14

<210> SEQ ID NO 17
<211> LENGTH: 14
<212> TYPE: DNA
<213> ORGANISM: Artificial Sequence
<220> FEATURE:
<223> OTHER INFORMATION: Synthetic Construct

<400> SEQUENCE: 17
atttggtttt tacg                                                         14

<210> SEQ ID NO 18
<211> LENGTH: 14
<212> TYPE: DNA
<213> ORGANISM: Artificial Sequence
<220> FEATURE:
<223> OTHER INFORMATION: Synthetic Construct

<400> SEQUENCE: 18
tttggttttt acgg                                                         14

<210> SEQ ID NO 19
<211> LENGTH: 14
<212> TYPE: DNA
<213> ORGANISM: Artificial Sequence
<220> FEATURE:
<223> OTHER INFORMATION: Synthetic Construct

<400> SEQUENCE: 19
ttggttttta cggt                                                         14

<210> SEQ ID NO 20
<211> LENGTH: 14
<212> TYPE: DNA
<213> ORGANISM: Artificial Sequence
<220> FEATURE:
<223> OTHER INFORMATION: Synthetic Construct

<400> SEQUENCE: 20 tggttttac ggtt                                                          14

<210> SEQ ID NO 21
<211> LENGTH: 14
<212> TYPE: DNA
<213> ORGANISM: Artificial Sequence
<220> FEATURE:
<223> OTHER INFORMATION: Synthetic Construct

<400> SEQUENCE: 21 ggttttacg gttt                                                          14

<210> SEQ ID NO 22
<211> LENGTH: 14
<212> TYPE: DNA
<213> ORGANISM: Artificial Sequence
<220> FEATURE:
<223> OTHER INFORMATION: Synthetic Construct

<400> SEQUENCE: 22
```
gtttttacgg tttt                                                        14

<210> SEQ ID NO 23
<211> LENGTH: 14
<212> TYPE: DNA
<213> ORGANISM: Artificial Sequence
<220> FEATURE:
<223> OTHER INFORMATION: Synthetic Construct

<400> SEQUENCE: 23
tttttacggt tttc                                                        14

<210> SEQ ID NO 24
<211> LENGTH: 14
<212> TYPE: DNA
<213> ORGANISM: Artificial Sequence
<220> FEATURE:
<223> OTHER INFORMATION: Synthetic Construct

<400> SEQUENCE: 24
ttttacggtt ttcg                                                        14

<210> SEQ ID NO 25
<211> LENGTH: 14
<212> TYPE: DNA
<213> ORGANISM: Artificial Sequence
<220> FEATURE:
<223> OTHER INFORMATION: Synthetic Construct

<400> SEQUENCE: 25
tttacggttt tcga                                                        14

<210> SEQ ID NO 26
<211> LENGTH: 14
<212> TYPE: DNA
<213> ORGANISM: Artificial Sequence
<220> FEATURE:
<223> OTHER INFORMATION: Synthetic Construct

<400> SEQUENCE: 26
ttacggtttt cgac                                                        14

<210> SEQ ID NO 27
<211> LENGTH: 14
<212> TYPE: DNA
<213> ORGANISM: Artificial Sequence
<220> FEATURE:
<223> OTHER INFORMATION: Synthetic Construct

<400> SEQUENCE: 27
tacggttttc gacg                                                        14

<210> SEQ ID NO 28
<211> LENGTH: 14
<212> TYPE: DNA
<213> ORGANISM: Artificial Sequence
<220> FEATURE:
<223> OTHER INFORMATION: Synthetic Construct

<400> SEQUENCE: 28
acggttttcg acgg                                                        14

<210> SEQ ID NO 29
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 29
cggttttcga cggg                                                           14

<210> SEQ ID NO 30
<211> LENGTH: 14
<212> TYPE: DNA
<213> ORGANISM: Artificial Sequence
<220> FEATURE:
<223> OTHER INFORMATION: Synthetic Construct

<400> SEQUENCE: 30
ggttttcgac gggg                                                           14

<210> SEQ ID NO 31
<211> LENGTH: 14
<212> TYPE: DNA
<213> ORGANISM: Artificial Sequence
<220> FEATURE:
<223> OTHER INFORMATION: Synthetic Construct

<400> SEQUENCE: 31
gttttcgacg gggg                                                           14

<210> SEQ ID NO 32
<211> LENGTH: 14
<212> TYPE: DNA
<213> ORGANISM: Artificial Sequence
<220> FEATURE:
<223> OTHER INFORMATION: Synthetic Construct

<400> SEQUENCE: 32
ttttcgacgg gggc                                                           14

<210> SEQ ID NO 33
<211> LENGTH: 14
<212> TYPE: DNA
<213> ORGANISM: Artificial Sequence
<220> FEATURE:
<223> OTHER INFORMATION: Synthetic Construct

<400> SEQUENCE: 33
tttcgacggg ggcg                                                           14

<210> SEQ ID NO 34
<211> LENGTH: 14
<212> TYPE: DNA
<213> ORGANISM: Artificial Sequence
<220> FEATURE:
<223> OTHER INFORMATION: Synthetic Construct

<400> SEQUENCE: 34
ttcgacgggg gcga                                                           14

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct

<400> SEQUENCE: 35
tcgacggggg cgat                                                           14
```

<210> SEQ ID NO 36
<211> LENGTH: 14
<212> TYPE: DNA
<213> ORGANISM: Artificial Sequence
<220> FEATURE:
<223> OTHER INFORMATION: Synthetic Construct

<400> SEQUENCE: 36
cgacgggggc gatt                                                        14

<210> SEQ ID NO 37
<211> LENGTH: 14
<212> TYPE: DNA
<213> ORGANISM: Artificial Sequence
<220> FEATURE:
<223> OTHER INFORMATION: Synthetic Construct

<400> SEQUENCE: 37 gacggggcg attc                                                         14

<210> SEQ ID NO 38
<211> LENGTH: 14
<212> TYPE: DNA
<213> ORGANISM: Artificial Sequence
<220> FEATURE:
<223> OTHER INFORMATION: Synthetic Construct

<400> SEQUENCE: 38 acggggcga ttcg                                                         14

<210> SEQ ID NO 39
<211> LENGTH: 14
<212> TYPE: DNA
<213> ORGANISM: Artificial Sequence
<220> FEATURE:
<223> OTHER INFORMATION: Synthetic Construct

<400> SEQUENCE: 39 cggggcgat tcgg                                                         14

<210> SEQ ID NO 40
<211> LENGTH: 14
<212> TYPE: DNA
<213> ORGANISM: Artificial Sequence
<220> FEATURE:
<223> OTHER INFORMATION: Synthetic Construct

<400> SEQUENCE: 40 ggggcgatt cggt                                                         14

<210> SEQ ID NO 41
<211> LENGTH: 14
<212> TYPE: DNA
<213> ORGANISM: Artificial Sequence
<220> FEATURE:
<223> OTHER INFORMATION: Synthetic Construct

<400> SEQUENCE: 41
ggggcgattc ggtg                                                        14

<210> SEQ ID NO 42
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 42
gggcgattcg gtgc                                                         14

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
ggcgattcgg tgcg                                                         14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
gcgattcggt gcgt                                                         14

<210> SEQ ID NO 45
<211> LENGTH: 14
<212> TYPE: DNA
<213> ORGANISM: Artificial Sequence
<220> FEATURE:
<223> OTHER INFORMATION: Synthetic Construct

<400> SEQUENCE: 45
cgattcggtg cgta                                                         14

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
gattcggtgc gtat                                                         14

<210> SEQ ID NO 47
<211> LENGTH: 14
<212> TYPE: DNA
<213> ORGANISM: Artificial Sequence
<220> FEATURE:
<223> OTHER INFORMATION: Synthetic Construct

<400> SEQUENCE: 47
attcggtgcg tata                                                         14

<210> SEQ ID NO 48
<211> LENGTH: 14
<212> TYPE: DNA
<213> ORGANISM: Artificial Sequence
<220> FEATURE:
<223> OTHER INFORMATION: Synthetic Construct

<400> SEQUENCE: 48
ttcggtgcgt atag                                                         14

<210> SEQ ID NO 49
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
tcggtgcgta tagg                                                    14

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
cggtgcgtat aggt                                                    14

<210> SEQ ID NO 51
<211> LENGTH: 14
<212> TYPE: DNA
<213> ORGANISM: Artificial Sequence
<220> FEATURE:
<223> OTHER INFORMATION: Synthetic Construct

<400> SEQUENCE: 51
ggtgcgtata ggta                                                    14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
gtgcgtatag gtat                                                    14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
tgcgtatagg tatc                                                    14

<210> SEQ ID NO 54
<211> LENGTH: 14
<212> TYPE: DNA
<213> ORGANISM: Artificial Sequence
<220> FEATURE:
<223> OTHER INFORMATION: Synthetic Construct

<400> SEQUENCE: 54
gcgtataggt atcg                                                    14

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
```
cgtataggta tcgc                                           14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
gtataggtat cgcg                                           14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
tataggtatc gcgc                                           14

<210> SEQ ID NO 58
<211> LENGTH: 14
<212> TYPE: DNA
<213> ORGANISM: Artificial Sequence
<220> FEATURE:
<223> OTHER INFORMATION: Synthetic Construct

<400> SEQUENCE: 58
ataggtatcg cgcg                                           14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
taggtatcgc gcgt                                           14

<210> SEQ ID NO 60
<211> LENGTH: 14
<212> TYPE: DNA
<213> ORGANISM: Artificial Sequence
<220> FEATURE:
<223> OTHER INFORMATION: Synthetic Construct

<400> SEQUENCE: 60
attcgcgtga tggt                                           14

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

<400> SEQUENCE: 61
ttaactcctt cgtc                                           14

<210> SEQ ID NO 62
<211> LENGTH: 25
<212> TYPE: DNA

```
<213> ORGANISM: Artificial Sequence
<220> FEATURE:
<223> OTHER INFORMATION: Synthetic Construct

<400> SEQUENCE: 62
gtttgtagtt aacgttatcg atttt                                    25

<210> SEQ ID NO 63
<211> LENGTH: 14
<212> TYPE: DNA
<213> ORGANISM: Artificial Sequence
<220> FEATURE:
<223> OTHER INFORMATION: Synthetic Construct

<400> SEQUENCE: 63
ttcgcgtgat ggtt                                                14

<210> SEQ ID NO 64
<211> LENGTH: 14
<212> TYPE: DNA
<213> ORGANISM: Artificial Sequence
<220> FEATURE:
<223> OTHER INFORMATION: Synthetic Construct

<400> SEQUENCE: 64
tcgcgtgatg gttt                                                14

<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
cgcgtgatgg tttt                                                14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
gcgtgatggt tttg                                                14

<210> SEQ ID NO 67
<211> LENGTH: 18
<212> TYPE: DNA
<213> ORGANISM: Artificial Sequence
<220> FEATURE:
<223> OTHER INFORMATION: Synthetic Construct

<400> SEQUENCE: 67
cgtgatggtt ttggatgc                                            18

<210> SEQ ID NO 68
<211> LENGTH: 17
<212> TYPE: DNA
<213> ORGANISM: Artificial Sequence
<220> FEATURE:
<223> OTHER INFORMATION: Synthetic Construct

<400> SEQUENCE: 68
gtgatggttt tggatgc                                             17
```

<210> SEQ ID NO 69
<211> LENGTH: 14
<212> TYPE: DNA
<213> ORGANISM: Artificial Sequence
<220> FEATURE:
<223> OTHER INFORMATION: Synthetic Construct

<400> SEQUENCE: 69
ttttggatgc gaac                                                    14

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
tttggatgcg aacg                                                    14

<210> SEQ ID NO 71
<211> LENGTH: 14
<212> TYPE: DNA
<213> ORGANISM: Artificial Sequence
<220> FEATURE:
<223> OTHER INFORMATION: Synthetic Construct

<400> SEQUENCE: 71
ttggatgcga acga                                                    14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
tggatgcgaa cgat                                                    14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
ggatgcgaac gata                                                    14

<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
gatgcgaacg ataa                                                    14

<210> SEQ ID NO 75
<211> LENGTH: 14
<212> TYPE: DNA
<213> ORGANISM: Artificial Sequence
<220> FEATURE:

<223> OTHER INFORMATION: Synthetic Construct

<400> SEQUENCE: 75
atgcgaacga taac					14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76
tgcgaacgat aacg					14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct

<400> SEQUENCE: 77
gcgaacgata acgt					14

<210> SEQ ID NO 78
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
cgaacgataa cgta					14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
gaacgataac gtat					14

<210> SEQ ID NO 80
<211> LENGTH: 14
<212> TYPE: DNA
<213> ORGANISM: Artificial Sequence
<220> FEATURE:
<223> OTHER INFORMATION: Synthetic Construct

<400> SEQUENCE: 80
aacgataacg tatt					14

<210> SEQ ID NO 81
<211> LENGTH: 14
<212> TYPE: DNA
<213> ORGANISM: Artificial Sequence
<220> FEATURE:
<223> OTHER INFORMATION: Synthetic Construct

<400> SEQUENCE: 81
acgataacgt atta					14

```
<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
cgataacgta ttag                                                        14

<210> SEQ ID NO 83
<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
gataacgtat tagc                                                        14

<210> SEQ ID NO 84
<211> LENGTH: 14
<212> TYPE: DNA
<213> ORGANISM: Artificial Sequence
<220> FEATURE:
<223> OTHER INFORMATION: Synthetic Construct

<400> SEQUENCE: 84
ataacgtatt agcg                                                        14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
taacgtatta gcgt                                                        14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
aacgtattag cgtt                                                        14

<210> SEQ ID NO 87
<211> LENGTH: 14
<212> TYPE: DNA
<213> ORGANISM: Artificial Sequence
<220> FEATURE:
<223> OTHER INFORMATION: Synthetic Construct

<400> SEQUENCE: 87
acgtattagc gttt                                                        14

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 88
cgtattagcg tttg                                                        14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
gtattagcgt ttgt                                                        14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
cgtttgttta gttc                                                        14

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
gtttgtttag ttcg                                                        14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
ttagttcgag tatc                                                        14

<210> SEQ ID NO 93
<211> LENGTH: 14
<212> TYPE: DNA
<213> ORGANISM: Artificial Sequence
<220> FEATURE:
<223> OTHER INFORMATION: Synthetic Construct

<400> SEQUENCE: 93
tagttcgagt atcg                                                        14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

<400> SEQUENCE: 94
agttcgagta tcgc                                                        14

<210> SEQ ID NO 95
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 95
gttcgagtat cgcg                                                          14

<210> SEQ ID NO 96
<211> LENGTH: 14
<212> TYPE: DNA
<213> ORGANISM: Artificial Sequence
<220> FEATURE:
<223> OTHER INFORMATION: Synthetic Construct

<400> SEQUENCE: 96
ttcgagtatc gcgc                                                          14

<210> SEQ ID NO 97
<211> LENGTH: 14
<212> TYPE: DNA
<213> ORGANISM: Artificial Sequence
<220> FEATURE:
<223> OTHER INFORMATION: Synthetic Construct

<400> SEQUENCE: 97
tcgagtatcg cgcg                                                          14

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
cgagtatcgc gcga                                                          14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
gagtatcgcg cgag                                                          14

<210> SEQ ID NO 100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 100
agtatcgcgc gagc                                                          14

<210> SEQ ID NO 101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 101
```

```
gtatcgcgcg agcg                                                        14

<210> SEQ ID NO 102
<211> LENGTH: 22
<212> TYPE: DNA
<213> ORGANISM: Artificial Sequence
<220> FEATURE:
<223> OTHER INFORMATION: Synthetic Construct

<400> SEQUENCE: 102
cggagaattt ggttttgggt ac                                               22

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103
aaaaacttaa accg                                                        14

<210> SEQ ID NO 104
<211> LENGTH: 25
<212> TYPE: DNA
<213> ORGANISM: Artificial Sequence
<220> FEATURE:
<223> OTHER INFORMATION: Synthetic Construct

<400> SEQUENCE: 104 tttttcggt atgtggacga taagg                                             25

<210> SEQ ID NO 105
<211> LENGTH: 21
<212> TYPE: DNA
<213> ORGANISM: Artificial Sequence
<220> FEATURE:
<223> OTHER INFORMATION: Synthetic Construct

<400> SEQUENCE: 105
ggagaatttg gttttgggta c                                                21

<210> SEQ ID NO 106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 106
tagttaacgt tatc                                                        14

<210> SEQ ID NO 107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 107
agttaacgtt atcg                                                        14

<210> SEQ ID NO 108
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 108
gttaacgtta tcga                                                      14

<210> SEQ ID NO 109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 109
ttaacgttat cgat                                                      14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 110
taacgttatc gatt                                                      14

<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
aacgttatcg attt                                                      14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
acgttatcga tttt                                                      14

<210> SEQ ID NO 113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 113
cgttatcgat tttg                                                      14

<210> SEQ ID NO 114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 114
gttatcgatt ttga                                                      14
```

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
ttatcgattt tgac                                                        14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
tatcgatttt gacg                                                        14

<210> SEQ ID NO 117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 117
atcgattttg acga                                                        14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
tcgattttga cgaa                                                        14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 119
cgattttgac gaag                                                        14

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
gattttgacg aagg                                                        14

<210> SEQ ID NO 121
<211> LENGTH: 24
<212> TYPE: DNA
<213> ORGANISM: Artificial Sequence
<220> FEATURE:
<223> OTHER INFORMATION: Synthetic Construct

```
<400> SEQUENCE: 121
cgattttgac gaaggagtta atgc                                    24

<210> SEQ ID NO 122
<211> LENGTH: 23
<212> TYPE: DNA
<213> ORGANISM: Artificial Sequence
<220> FEATURE:
<223> OTHER INFORMATION: Synthetic Construct

<400> SEQUENCE: 122
gattttgacg aaggagttaa tgc                                     23

<210> SEQ ID NO 123
<211> LENGTH: 21
<212> TYPE: DNA
<213> ORGANISM: Artificial Sequence
<220> FEATURE:
<223> OTHER INFORMATION: Synthetic Construct

<400> SEQUENCE: 123
cggaagtgag gtatttttttt c                                      21

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 124
attacaatct aatt                                               14

<210> SEQ ID NO 125
<211> LENGTH: 25
<212> TYPE: DNA
<213> ORGANISM: Artificial Sequence
<220> FEATURE:
<223> OTHER INFORMATION: Synthetic Construct

<400> SEQUENCE: 125
attacgagga gttaggattt tatta                                   25

<210> SEQ ID NO 126
<211> LENGTH: 20
<212> TYPE: DNA
<213> ORGANISM: Artificial Sequence
<220> FEATURE:
<223> OTHER INFORMATION: Synthetic Construct

<400> SEQUENCE: 126
ggaagtgagg tattttttttc                                        20

<210> SEQ ID NO 127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 127
ttcggtatgt ggac                                               14

<210> SEQ ID NO 128
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
tcggtatgtg gacg                                                    14

<210> SEQ ID NO 129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 129
cggtatgtgg acga                                                    14

<210> SEQ ID NO 130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 130
ggtatgtgga cgat                                                    14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
gtggacgata aggc                                                    14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
tggacgataa ggcg                                                    14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 133
ggacgataag gcgg                                                    14

<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
```

```
gacgataagg cggt                                                    14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
acgataaggc ggtt                                                    14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
cgataaggcg gttt                                                    14

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
gataaggcgg ttta                                                    14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
ttagggataa tatt                                                    14

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 139
cattatcgtt cacg                                                    14

<210> SEQ ID NO 140
<211> LENGTH: 25
<212> TYPE: DNA
<213> ORGANISM: Artificial Sequence
<220> FEATURE:
<223> OTHER INFORMATION: Synthetic Construct

<400> SEQUENCE: 140
cgcgagttaa agttttgatt attgt                                        25

<210> SEQ ID NO 141
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 141
tagggataat atta                                                        14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
agggataata ttaa                                                        14

<210> SEQ ID NO 143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 143
gggataatat taat                                                        14

<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
ggataatatt aata                                                        14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
gataatatta ataa                                                        14

<210> SEQ ID NO 146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 146
ataatattaa taat                                                        14

<210> SEQ ID NO 147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 147
taatattaat aata                                                        14
```

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
aatattaata atag                                                        14

<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149
atattaataa tagg                                                        14

<210> SEQ ID NO 150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 150
tattaataat aggg                                                        14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151
attaataata gggg                                                        14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 152
ttaataatag ggga                                                        14

<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153
taataatagg ggag                                                        14

<210> SEQ ID NO 154
<211> LENGTH: 14
<212> TYPE: DNA
<213> ORGANISM: Artificial Sequence
<220> FEATURE:

<223> OTHER INFORMATION: Synthetic Construct

<400> SEQUENCE: 154
aataataggg gagt                                                    14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 155
ataatagggg agtt                                                    14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 156
taatagggga gttg                                                    14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157 aatagggag ttgg                                                     14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158 atagggagt tgga                                                     14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 159
taggggagtt ggat                                                    14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 160
aggggagttg gatt                                                    14

```
<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161
ggggagttgg atta                                                    14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 162
gggagttgga ttac                                                    14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 163
ggagttggat tacg                                                    14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164
gagttggatt acga                                                    14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165
agttggatta cgag                                                    14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 166
gttggattac gagg                                                    14

<210> SEQ ID NO 167
<211> LENGTH: 14
<212> TYPE: DNA
<213> ORGANISM: Artificial Sequence
<220> FEATURE:
<223> OTHER INFORMATION: Synthetic Construct
```

-continued

<400> SEQUENCE: 167
ttggattacg agga                                                         14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
tggattacga ggag                                                         14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
ggattacgag gagt                                                         14

<210> SEQ ID NO 170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 170
gattacgagg agtt                                                         14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
attacgagga gtta                                                         14

<210> SEQ ID NO 172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 172
ttacgaggag ttag                                                         14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 173
tacgaggagt tagg                                                         14

<210> SEQ ID NO 174
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 174
acgaggagtt agga                                                      14

<210> SEQ ID NO 175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 175
cgaggagtta ggat                                                      14

<210> SEQ ID NO 176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 176
gaggagttag gatt                                                      14

<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
aggagttagg attt                                                      14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
ggagttagga tttt                                                      14

<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
gagttaggat ttta                                                      14

<210> SEQ ID NO 180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180
```
agttaggatt ttat                                               14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181
gttaggattt tatt                                               14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182
ttaggatttt atta                                               14

<210> SEQ ID NO 183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 183
taggatttta ttag                                               14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184
aggattttat taga                                               14

<210> SEQ ID NO 185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 185
ggattttatt agat                                               14

<210> SEQ ID NO 186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 186
gattttatta gatg                                               14

<210> SEQ ID NO 187
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 187
attttattag atgg                                                         14

<210> SEQ ID NO 188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 188
ttttattaga tgga                                                         14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189
tttattagat ggaa                                                         14

<210> SEQ ID NO 190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 190
ttattagatg gaag                                                         14

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191
tattagatgg aagt                                                         14

<210> SEQ ID NO 192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 192
attagatgga agtg                                                         14

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
ttagatggaa gtgt                                                         14
```

```
<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
tagatggaag tgta                                                           14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
agatggaagt gtaa                                                           14

<210> SEQ ID NO 196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 196
gatggaagtg taag                                                           14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
aggatatttt gcgc                                                           14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 198
aacaattaat atcc                                                           14

<210> SEQ ID NO 199
<211> LENGTH: 24
<212> TYPE: DNA
<213> ORGANISM: Artificial Sequence
<220> FEATURE:
<223> OTHER INFORMATION: Synthetic Construct

<400> SEQUENCE: 199
agaagtggtt tttatttttt tcgt                                                24

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 200
ggatattttg cgcg                                                        14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201
gatattttgc gcga                                                        14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
atattttgcg cgag                                                        14

<210> SEQ ID NO 203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 203
tattttgcgc gagt                                                        14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
attttgcgcg agtt                                                        14

<210> SEQ ID NO 205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 205
ttttgcgcga gtta                                                        14

<210> SEQ ID NO 206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 206
tttgcgcgag ttaa                                                        14

<210> SEQ ID NO 207
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207
ttgcgcgagt taaa                                                   14

<210> SEQ ID NO 208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 208
tgcgcgagtt aaag                                                   14

<210> SEQ ID NO 209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 209
gcgcgagtta aagt                                                   14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210
cgcgagttaa agtt                                                   14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
gcgagttaaa gttt                                                   14

<210> SEQ ID NO 212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 212
ttttggacgt gaac                                                   14

<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
```

```
tttggacgtg aacg                                                14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214
ttggacgtga acga                                                14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
tggacgtgaa cgat                                                14

<210> SEQ ID NO 216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 216
ggacgtgaac gata                                                14

<210> SEQ ID NO 217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 217
gacgtgaacg ataa                                                14

<210> SEQ ID NO 218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 218
acgtgaacga taat                                                14

<210> SEQ ID NO 219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 219
cgtgaacgat aatg                                                14

<210> SEQ ID NO 220
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 220
gtgaacgata atgt                                                       14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
tttttcgtta gttc                                                       14

<210> SEQ ID NO 222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 222
aaatcaccta tccg                                                       14

<210> SEQ ID NO 223
<211> LENGTH: 25
<212> TYPE: DNA
<213> ORGANISM: Artificial Sequence
<220> FEATURE:
<223> OTHER INFORMATION: Synthetic Construct

<400> SEQUENCE: 223
taaatgatta agattttgag gaaaa                                           25

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
ttttcgttag ttcg                                                       14

<210> SEQ ID NO 225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 225
tttcgttagt tcgg                                                       14

<210> SEQ ID NO 226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 226
ttcgttagtt cggt                                                       14
```

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
tcgttagttc ggtt                                                     14

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
cgttagttcg gttt                                                     14

<210> SEQ ID NO 229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 229
gttagttcgg tttt                                                     14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
ttagttcggt tttc                                                     14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 231
tagttcggtt ttcg                                                     14

<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
agttcggttt tcga                                                     14

<210> SEQ ID NO 233
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 233
gttcggtttt cgaa                                                          14

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
ttcggttttc gaaa                                                          14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 235
tcggttttcg aaaa                                                          14

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
cggttttcga aaat                                                          14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237
ggttttcgaa aatt                                                          14

<210> SEQ ID NO 238
<211> LENGTH: 19
<212> TYPE: DNA
<213> ORGANISM: Artificial Sequence
<220> FEATURE:
<223> OTHER INFORMATION: Synthetic Construct

<400> SEQUENCE: 238
cggttttttt tattttacg                                                     19

<210> SEQ ID NO 239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 239
taaaaaaaaa ataa                                                          14
```

```
<210> SEQ ID NO 240
<211> LENGTH: 25
<212> TYPE: DNA
<213> ORGANISM: Artificial Sequence
<220> FEATURE:
<223> OTHER INFORMATION: Synthetic Construct

<400> SEQUENCE: 240
agagttacga gtttagttcg aatat                                              25

<210> SEQ ID NO 241
<211> LENGTH: 18
<212> TYPE: DNA
<213> ORGANISM: Artificial Sequence
<220> FEATURE:
<223> OTHER INFORMATION: Synthetic Construct

<400> SEQUENCE: 241
ggtttttttt attttacg                                                      18

<210> SEQ ID NO 242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 242
tgggattcgg atat                                                          14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
tcttcgcgat ccaa                                                          14

<210> SEQ ID NO 244
<211> LENGTH: 25
<212> TYPE: DNA
<213> ORGANISM: Artificial Sequence
<220> FEATURE:
<223> OTHER INFORMATION: Synthetic Construct

<400> SEQUENCE: 244
tttcgaattg gtgttgaaac gcgtt                                              25

<210> SEQ ID NO 245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 245
gggattcgga tatc                                                          14

<210> SEQ ID NO 246
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 246
ggattcggat atcg                                                         14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247
gattcggata tcgg                                                         14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248
attcggatat cggg                                                         14

<210> SEQ ID NO 249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 249
ttcggatatc ggga                                                         14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250
tcggatatcg ggaa                                                         14

<210> SEQ ID NO 251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 251
cggatatcgg gaag                                                         14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 252
ggatatcggg aaga                                                         14

<210> SEQ ID NO 253
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 253
gatatcggga agaa                                                         14

<210> SEQ ID NO 254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 254
atatcgggaa gaat                                                         14

<210> SEQ ID NO 255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 255
tatcgggaag aatt                                                         14

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
atcgggaaga attt                                                         14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257
tcgggaagaa tttt                                                         14

<210> SEQ ID NO 258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 258
cgggaagaat tttt                                                         14

<210> SEQ ID NO 259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
```
gggaagaatt tttt                                                         14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
ggaagaattt tttg                                                         14

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
gaagaatttt ttgt                                                         14

<210> SEQ ID NO 262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 262
aagaattttt tgta                                                         14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263
agaatttttt gtag                                                         14

<210> SEQ ID NO 264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 264 gaatttttttg taga                                                        14

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
aattttttgt agag                                                         14

<210> SEQ ID NO 266
<211> LENGTH: 14
<212> TYPE: DNA
<213> ORGANISM: Artificial Sequence -continued
<220> FEATURE:
<223> OTHER INFORMATION: Synthetic Construct

<400> SEQUENCE: 266
attttttgta gagt                                                         14

<210> SEQ ID NO 267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 267 tttttttgtag agtt                                                        14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 268
tttttgtaga gtta                                                         14

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
ttttgtagag ttac                                                         14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
tttgtagagt tacg                                                         14

<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 271
ttgtagagtt acga                                                         14

<210> SEQ ID NO 272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 272
tgtagagtta cgag                                                         14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
gtagagttac gagt                                                        14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
tagagttacg agtt                                                        14

<210> SEQ ID NO 275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 275
agagttacga gttt                                                        14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
gagttacgag ttta                                                        14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 277
agttacgagt ttag                                                        14

<210> SEQ ID NO 278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
gttacgagtt tagt                                                        14

<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 279
ttacgagttt agtt                                                        14

<210> SEQ ID NO 280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 280
tacgagttta gttc                                                        14

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281
acgagtttag ttcg                                                        14

<210> SEQ ID NO 282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 282
cgagtttagt tcga                                                        14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
gagtttagtt cgaa                                                        14

<210> SEQ ID NO 284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 284
agtttagttc gaat                                                        14

<210> SEQ ID NO 285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 285
gtttagttcg aata                                                        14

<210> SEQ ID NO 286
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286
tttagttcga atat                                                        14

<210> SEQ ID NO 287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 287
ttagttcgaa tatt                                                        14

<210> SEQ ID NO 288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 288
tagttcgaat attt                                                        14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
agttcgaata ttta                                                        14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
gttcgaatat ttat                                                        14

<210> SEQ ID NO 291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 291
ttcgaatatt tatt                                                        14

<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
```

```
tcgaatattt attt                                                  14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
cgaatattta tttt                                                  14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
gaatatttat tttt                                                  14

<210> SEQ ID NO 295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 295
aatatttatt tttt                                                  14

<210> SEQ ID NO 296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 296
atatttattt tttt                                                  14

<210> SEQ ID NO 297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 297
tatttatttt tttt                                                  14

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 298
atttattttt tttt                                                  14

<210> SEQ ID NO 299
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 299
tttatttttt tttt                                                        14

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300 ttatttttt ttta                                                         14

<210> SEQ ID NO 301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 301
tcgtgtaaaa tgga                                                        14

<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
acgcgcgata ccta                                                        14

<210> SEQ ID NO 303
<211> LENGTH: 25
<212> TYPE: DNA
<213> ORGANISM: Artificial Sequence
<220> FEATURE:
<223> OTHER INFORMATION: Synthetic Construct

<400> SEQUENCE: 303
ttcgacgggg gcgattcggt gcgta                                            25

<210> SEQ ID NO 304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 304
cgtgtaaaat ggag                                                        14

<210> SEQ ID NO 305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 305
gtgtaaaatg gagt                                                        14
```

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
tgtaaaatgg agtc                                                    14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
gtaaaatgga gtcg                                                    14

<210> SEQ ID NO 308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 308
taaaatggag tcga                                                    14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
aaaatggagt cgac                                                    14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 310
aaatggagtc gacg                                                    14

<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
aatggagtcg acgg                                                    14

<210> SEQ ID NO 312
<211> LENGTH: 14
<212> TYPE: DNA
<213> ORGANISM: Artificial Sequence
<220> FEATURE:

<223> OTHER INFORMATION: Synthetic Construct

<400> SEQUENCE: 312
atggagtcga cggt					14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
tggagtcgac ggta					14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 314
ggagtcgacg gtag					14

<210> SEQ ID NO 315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 315
gagtcgacgg tagt					14

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
agtcgacggt agta					14

<210> SEQ ID NO 317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 317
gtcgacggta gtaa					14

<210> SEQ ID NO 318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 318
tcgacggtag taag					14

```
<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
cgacggtagt aagt                                                       14

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
gacggtagta agta                                                       14

<210> SEQ ID NO 321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 321
acggtagtaa gtat                                                       14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
cggtagtaag tatt                                                       14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
ggtagtaagt attt                                                       14

<210> SEQ ID NO 324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 324
gtagtaagta tttc                                                       14

<210> SEQ ID NO 325
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 325
tagtaagtat ttcg                                                      14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
agtaagtatt tcga                                                      14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
gtaagtattt cgaa                                                      14

<210> SEQ ID NO 328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 328
taagtatttc gaat                                                      14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
aagtatttcg aatt                                                      14

<210> SEQ ID NO 330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 330
agtatttcga attg                                                      14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 331
gtatttcgaa ttgg                                                      14

<210> SEQ ID NO 332
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 332
tatttcgaat tggt                                                       14

<210> SEQ ID NO 333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 333
atttcgaatt ggtg                                                       14

<210> SEQ ID NO 334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 334
tttcgaattg gtgt                                                       14

<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
ttcgaattgg tgtt                                                       14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336
tcgaattggt gttg                                                       14

<210> SEQ ID NO 337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 337
cgaattggtg ttga                                                       14

<210> SEQ ID NO 338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338
```
gaattggtgt tgaa                                                        14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339
aattggtgtt gaaa                                                        14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
attggtgttg aaac                                                        14

<210> SEQ ID NO 341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 341
ttggtgttga aacg                                                        14

<210> SEQ ID NO 342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 342
tggtgttgaa acgc                                                        14

<210> SEQ ID NO 343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 343
ggtgttgaaa cgcg                                                        14

<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
gtgttgaaac gcgt                                                        14

<210> SEQ ID NO 345
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 345
tgttgaaacg cgtt                                                        14

<210> SEQ ID NO 346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 346
gttgaaacgc gttt                                                        14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 347
ttgaaacgcg tttt                                                        14

<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
tgaaacgcgt tttg                                                        14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349
gaaacgcgtt ttgg                                                        14

<210> SEQ ID NO 350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 350
aaacgcgttt tgga                                                        14

<210> SEQ ID NO 351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 351
aacgcgtttt ggat                                                        14
```

```
<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
acgcgttttg gatc                                                        14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
cgcgttttgg atcg                                                        14

<210> SEQ ID NO 354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 354
gcgttttgga tcgc                                                        14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
cgttttggat cgcg                                                        14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 356
gttttggatc gcga                                                        14

<210> SEQ ID NO 357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357
ttttggatcg cgaa                                                        14

<210> SEQ ID NO 358
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 358
tttggatcgc gaag                                                                14

<210> SEQ ID NO 359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 359
ttggatcgcg aaga                                                                14

<210> SEQ ID NO 360
<211> LENGTH: 17
<212> TYPE: DNA
<213> ORGANISM: Artificial Sequence
<220> FEATURE:
<223> OTHER INFORMATION: Synthetic Construct

<400> SEQUENCE: 360
cggatgtatt tagatac                                                             17

<210> SEQ ID NO 361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 361
tacctctaaa aata                                                                14

<210> SEQ ID NO 362
<211> LENGTH: 20
<212> TYPE: DNA
<213> ORGANISM: Artificial Sequence
<220> FEATURE:
<223> OTHER INFORMATION: Synthetic Construct

<400> SEQUENCE: 362
cgcggagcgc ggagttcgta                                                          20

<210> SEQ ID NO 363
<211> LENGTH: 16
<212> TYPE: DNA
<213> ORGANISM: Artificial Sequence
<220> FEATURE:
<223> OTHER INFORMATION: Synthetic Construct

<400> SEQUENCE: 363
ggatgtattt agatac                                                              16

<210> SEQ ID NO 364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 364
cgttatttag tttc                                                                14

<210> SEQ ID NO 365

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365
gttatttagt ttcg                                                       14

<210> SEQ ID NO 366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 366
agtttcggga gttc                                                       14

<210> SEQ ID NO 367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 367
tcctcccgat ctat                                                       14

<210> SEQ ID NO 368
<211> LENGTH: 25
<212> TYPE: DNA
<213> ORGANISM: Artificial Sequence
<220> FEATURE:
<223> OTHER INFORMATION: Synthetic Construct

<400> SEQUENCE: 368
cggtagtttg gttacggcgg gtagg                                           25

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
gtttcgggag ttcg                                                       14

<210> SEQ ID NO 370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 370
tttcgggagt tcgc                                                       14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371
```
ttcgggagtt cgcg                                                    14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
tcgggagttc gcgg                                                    14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
cgggagttcg cgga                                                    14

<210> SEQ ID NO 374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 374
gggagttcgc ggag                                                    14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
ggagttcgcg gagc                                                    14

<210> SEQ ID NO 376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 376
gagttcgcgg agcg                                                    14

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
agttcgcgga gcgc                                                    14

<210> SEQ ID NO 378
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 378
gttcgcggag cgcg                                                         14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
ttcgcggagc gcgg                                                         14

<210> SEQ ID NO 380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 380
tcgcggagcg cgga                                                         14

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
cgcggagcgc ggag                                                         14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
gcggagcgcg gagt                                                         14

<210> SEQ ID NO 383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 383
cggagcgcgg agtt                                                         14

<210> SEQ ID NO 384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 384
ggagcgcgga gttc                                                         14
```

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
gagcgcggag ttcg                                                        14

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
agcgcggagt tcgt                                                        14

<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 387
gcgcggagtt cgta                                                        14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
cgcggagttc gtat                                                        14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
gcggagttcg tatt                                                        14

<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390
cggagttcgt atta                                                        14

<210> SEQ ID NO 391
<211> LENGTH: 14
<212> TYPE: DNA
<213> ORGANISM: Artificial Sequence
<220> FEATURE:

<223> OTHER INFORMATION: Synthetic Construct

<400> SEQUENCE: 391
ggagttcgta ttat                                              14

<210> SEQ ID NO 392
<211> LENGTH: 23
<212> TYPE: DNA
<213> ORGANISM: Artificial Sequence
<220> FEATURE:
<223> OTHER INFORMATION: Synthetic Construct

<400> SEQUENCE: 392
cgtattattt ttagaggtag gac                                    23

<210> SEQ ID NO 393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 393
ggacgtagtt tttc                                              14

<210> SEQ ID NO 394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394
atatattttc actt                                              14

<210> SEQ ID NO 395
<211> LENGTH: 25
<212> TYPE: DNA
<213> ORGANISM: Artificial Sequence
<220> FEATURE:
<223> OTHER INFORMATION: Synthetic Construct

<400> SEQUENCE: 395
aatttagata ttttgatgga ggata                                  25

<210> SEQ ID NO 396
<211> LENGTH: 14
<212> TYPE: DNA
<213> ORGANISM: Artificial Sequence
<220> FEATURE:
<223> OTHER INFORMATION: Synthetic Construct

<400> SEQUENCE: 396
gacgtagttt ttcg                                              14

<210> SEQ ID NO 397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 397
acgtagtttt tcgt                                              14

-continued

```
<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
cgtagttttt cgtt                                                       14

<210> SEQ ID NO 399
<211> LENGTH: 22
<212> TYPE: DNA
<213> ORGANISM: Artificial Sequence
<220> FEATURE:
<223> OTHER INFORMATION: Synthetic Construct

<400> SEQUENCE: 399
cgtagttttt cgttttgaat tc                                              22

<210> SEQ ID NO 400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 400
ttcgttttga attc                                                       14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
tcgttttgaa ttcg                                                       14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
cgttttgaat tcgc                                                       14

<210> SEQ ID NO 403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 403
gttttgaatt cgcg                                                       14

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 404
ttttgaattc gcgt                                                         14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
tttgaattcg cgta                                                         14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
ttgaattcgc gtag                                                         14

<210> SEQ ID NO 407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 407
tgaattcgcg tagc                                                         14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
gaattcgcgt agcg                                                         14

<210> SEQ ID NO 409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 409
aattcgcgta gcgg                                                         14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
attcgcgtag cggt                                                         14

<210> SEQ ID NO 411
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 411
ttcgcgtagc ggta                                                      14

<210> SEQ ID NO 412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 412
tcgcgtagcg gtag                                                      14

<210> SEQ ID NO 413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 413
cgcgtagcgg tagt                                                      14

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
gcgtagcggt agtt                                                      14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
cgtagcggta gttt                                                      14

<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416
gtagcggtag tttg                                                      14

<210> SEQ ID NO 417
<211> LENGTH: 15
<212> TYPE: DNA
<213> ORGANISM: Artificial Sequence
<220> FEATURE:
<223> OTHER INFORMATION: Synthetic Construct

<400> SEQUENCE: 417
```
cggtagtttg gttac                                                         15

<210> SEQ ID NO 418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 418
ggtagtttgg ttac                                                          14

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
agtttggtta cggc                                                          14

<210> SEQ ID NO 420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 420
gtttggttac ggcg                                                          14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421
tttggttacg gcgg                                                          14

<210> SEQ ID NO 422
<211> LENGTH: 14
<212> TYPE: DNA
<213> ORGANISM: Artificial Sequence
<220> FEATURE:
<223> OTHER INFORMATION: Synthetic Construct

<400> SEQUENCE: 422
ttggttacgg cggg                                                          14

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
tggttacggc gggt                                                          14

<210> SEQ ID NO 424
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 424
ggttacggcg ggta                                                   14

<210> SEQ ID NO 425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 425
gttacggcgg gtag                                                   14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 426
ttacggcggg tagg                                                   14

<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427
tacggcgggt agga                                                   14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
acggcgggta ggat                                                   14

<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
cggcgggtag gata                                                   14

<210> SEQ ID NO 430
<211> LENGTH: 14
<212> TYPE: DNA
<213> ORGANISM: Artificial Sequence
<220> FEATURE:
<223> OTHER INFORMATION: Synthetic Construct

<400> SEQUENCE: 430
ggcgggtagg atag                                                   14
```

<210> SEQ ID NO 431
<211> LENGTH: 15
<212> TYPE: DNA
<213> ORGANISM: Artificial Sequence
<220> FEATURE:
<223> OTHER INFORMATION: Synthetic Construct

<400> SEQUENCE: 431
cgggtaggat agatc                                                        15

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
gggtaggata gatc                                                         14

<210> SEQ ID NO 433
<211> LENGTH: 21
<212> TYPE: DNA
<213> ORGANISM: Artificial Sequence
<220> FEATURE:
<223> OTHER INFORMATION: Synthetic Construct

<400> SEQUENCE: 433
attcggtcgt ataggtatcg c                                                 21

<210> SEQ ID NO 434
<211> LENGTH: 21
<212> TYPE: DNA
<213> ORGANISM: Artificial Sequence
<220> FEATURE:
<223> OTHER INFORMATION: Synthetic Construct

<400> SEQUENCE: 434
caaattctcc gaaacgtcgc g                                                 21

<210> SEQ ID NO 435
<211> LENGTH: 26
<212> TYPE: DNA
<213> ORGANISM: Artificial Sequence
<220> FEATURE:
<223> OTHER INFORMATION: Synthetic Construct

<400> SEQUENCE: 435
cgtattcgcg tgatggtttt ggatgc                                            26

<210> SEQ ID NO 436
<211> LENGTH: 1620
<212> TYPE: DNA
<213> ORGANISM: Homo sapiens

<400> SEQUENCE: 436
ctattaaagc gaatacggta gatttccatc ccctttttgaa gaacagtagg tggagctatt      60
taagatataa aaacgaaata tcctttctgg gagttcaaga ttgtgcagta attggttagg     120
actctgagcg ccgctgttca ccaatcgggg agagaaaagc ggagatcctg ctcgccttgc     180
acgcgcctga agcacaaagc agatagctag gaatgaacca tccctgggag tatgtggaaa     240
caacggagga gctctgactt cccaactgtc ccattctatg ggcgaaggaa ctgctcctga     300
cttcagtggt taagggcaga attgaaaata attctggagg aagataagaa tgattcctgc     360

```
gcgactgcac cgggactaca aagggcttgt cctgctggga atcctcctgg ggactctgtg      420
ggagaccgga tgcacccaga tacgctattc agttccggaa gagctggaga aaggctctag      480
ggtgggcgac atctccaggg acctggggct ggagccccgg gagctcgcgg agcgcggagt      540
ccgcatcatc cccagaggta ggacgcagct tttcgccctg aatccgcgca gcggcagctt      600
ggtcacggcg ggcaggatag accgggagga gctctgtatg ggggccatca agtgtcaatt      660
aaatctagac attctgatgg aggataaagt gaaaatatat ggagtagaag tagaagtaag      720
ggacattaac gacaatgcgc cttactttcg tgaaagtgaa ttagaaataa aaattagtga      780
aaatgcagcc actgagatgc ggttccctct accccacgcc tgggatccgg atatcgggaa      840
gaactctctg cagagctacg agctcagccc gaacactcac ttctccctca tcgtgcaaaa      900
tggagccgac ggtagtaagt accccgaatt ggtgctgaaa cgcgccctgg accgcgaaga      960
aaaggctgct caccacctgg tccttacggc ctccgacggg ggcgacccgg tgcgcacagg     1020
caccgcgcgc atccgcgtga tggttctgga tgcgaacgac aacgcaccag cgtttgctca     1080
gcccgagtac cgcgcgagcg ttccggagaa tctggccttg ggcacgcagc tgcttgtagt     1140
caacgctacc gaccctgacg aaggagtcaa tgcggaagtg aggtattcct tccggtatgt     1200
ggacgacaag gcggcccaag ttttcaaact agattgtaat tcagggacaa tatcaacaat     1260
aggggagttg gaccacgagg agtcaggatt ctaccagatg gaagtgcaag caatggataa     1320
tgcaggatat tctgcgcgag ccaaagtcct gatcactgtt ctggacgtga acgacaatgc     1380
cccagaagtg gtcctcacct ctctcgccag ctcggttccc gaaaactctc cagagggac     1440 attaattgcc cttttaaatg taaatgacca agattctgag gaaaacggac aggtgatctg     1500
tttcatccaa ggaaatctgc cctttaaatt agaaaaatct tacggaaatt actatagttt     1560
agtcacagac atagtcttgg atagggaaca ggttcctagc tacaacatca cagtgaccgc     1620
```

<210> SEQ ID NO 437
<211> LENGTH: 482
<212> TYPE: DNA
<213> ORGANISM: Homo sapiens

<400> SEQUENCE: 437

```
cccctttgga agaacagtag gtggagctat ttaagatata aaaacgaaat atcctttctg       60
ggagttcaag attgtgcagt aattggttag gactctgagc gccgctgttc accaatcggg      120
gagagaaaag cggagatcct gctcgccttg cacgcgcctg aagcacaaag cagatagcta      180
ggaatgaacc atccctggga gtatgtggaa acaacgagg agctctgact tcccaactgt       240
cccattctat gggcgaagga actgctcctg acttcagtgg ttaagggcag aattgaaaat      300
aattctggag gaagataaga atgattcctg cgcgactgca ccgggactac aaagggcttg      360
tcctgctggg aatcctcctg gggactctgt gggagaccgg atgcacccag atacgctatt      420
cagttccgga gagctggag aaaggctcta gggtgggcga catctccagg gacctggggc      480
tg                                                                     482
```

<210> SEQ ID NO 438
<211> LENGTH: 598
<212> TYPE: DNA
<213> ORGANISM: Homo sapiens

<400> SEQUENCE: 438

```
gcttgtcctg ctgggaatcc tcctggggac tctgtgggag accggatgca cccagatacg       60
```

```
ctattcagtt ccggaagagc tggagaaagg ctctagggtg ggcgacatct ccagggacct      120
ggggctggag ccccgggagc tcgcggagcg cggagtccgc atcatcccca gaggtaggac      180
gcagcttttc gccctgaatc cgcgcagcgg cagcttggtc acggcgggca ggatagaccg      240
ggaggagctc tgtatggggg ccatcaagtg tcaattaaat ctagacattc tgatggagga      300
taaagtgaaa atatatggag tagaagtaga agtaagggac attaacgaca atgcgcctta      360
ctttcgtgaa agtgaattag aaataaaaat tagtgaaaat gcagccactg agatgcggtt      420
ccctctaccc cacgcctggg atccggatat cgggaagaac tctctgcaga gctacgagct      480
cagcccgaac actcacttct ccctcatcgt gcaaaatgga gccgacggta gtaagtaccc      540
cgaattggtg ctgaaacgcg ccctggaccg cgaagaaaag gctgctcacc acctggtc       598

<210> SEQ ID NO 439
<211> LENGTH: 638
<212> TYPE: DNA
<213> ORGANISM: Homo sapiens

<400> SEQUENCE: 439
gaaaaggctg ctcaccacct ggtccttacg gcctccgacg ggggcgaccc ggtgcgcaca       60
ggcaccgcgc gcatccgcgt gatggttctg gatgcgaacg acaacgcacc agcgtttgct      120
cagcccgagt accgcgcgag cgttccggag aatctggcct tgggcacgca gctgcttgta      180
gtcaacgcta ccgaccctga cgaaggagtc aatgcggaag tgaggtattc cttccggtat      240
gtggacgaca aggcggccca agttttcaaa ctagattgta attcagggac aatatcaaca      300 atagggagt tggaccacga ggagtcagga ttctaccaga tggaagtgca agcaatggat      360
aatgcaggat attctgcgcg agccaaagtc ctgatcactg ttctggacgt gaacgacaat      420
gccccagaag tggtcctcac ctctctcgcc agctcggttc ccgaaaactc tcccagaggg      480
acattaattg cccttttaaa tgtaaatgac caagattctg aggaaaacgg acaggtgatc      540
tgtttcatcc aaggaaatct gcccttttaa ttagaaaaat cttacggaaa ttactatagt      600
ttagtcacag acatagtctt ggatagggaa caggttcc                             638
```